US007977067B2

(12) United States Patent
Power et al.

(10) Patent No.: US 7,977,067 B2
(45) Date of Patent: Jul. 12, 2011

(54) PRODUCTION OF FUNCTIONAL ANTIBODIES IN FILAMENTOUS FUNGI

(75) Inventors: Scott D. Power, San Bruno, CA (US); Huaming Wang, Fremont, CA (US); Michael Ward, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 965 days.

(21) Appl. No.: 11/007,886

(22) Filed: Dec. 9, 2004

(65) Prior Publication Data

US 2005/0158825 A1 Jul. 21, 2005

Related U.S. Application Data

(62) Division of application No. 10/418,836, filed on Apr. 17, 2003, now abandoned.

(60) Provisional application No. 60/373,889, filed on Apr. 18, 2002, provisional application No. 60/411,540, filed on Sep. 18, 2002, provisional application No. 60/411,537, filed on Sep. 18, 2002, provisional application No. 60/452,134, filed on Mar. 4, 2003.

(51) Int. Cl.
*C07K 16/46* (2006.01)

(52) U.S. Cl. .................. 435/69.1; 435/254.3; 530/387.3

(58) Field of Classification Search ........................ None
See application file for complete search history.

(56) References Cited

U.S. PATENT DOCUMENTS 4,486,553 A 12/1984 Wesch
5,166,058 A * 11/1992 Wang et al. .................. 435/69.1
5,218,093 A 6/1993 Guo et al.
5,364,770 A 11/1994 Berka et al.
5,578,463 A * 11/1996 Berka et al. .................. 435/69.1
5,610,034 A * 3/1997 Nyyssonen et al. ......... 435/69.6
5,643,745 A * 7/1997 Stuart .......................... 435/69.1
5,665,866 A * 9/1997 Weir et al. .................. 530/390.5
5,679,543 A * 10/1997 Lawlis .......................... 435/69.1
5,683,899 A * 11/1997 Stuart .......................... 435/69.6
6,066,493 A * 5/2000 Shuster et al. ............. 435/254.3
6,140,113 A * 10/2000 Schneck et al. ............ 435/320.1
6,204,023 B1 * 3/2001 Robinson et al. ............ 435/71.3
6,232,112 B1 * 5/2001 Catcheside ................ 435/254.4
6,265,204 B1 7/2001 Ward et al.
6,361,969 B1 * 3/2002 Galeotti ....................... 435/69.1
6,506,593 B2 * 1/2003 Mantyla et al. ............... 435/267
6,682,735 B2 * 1/2004 Lowman et al. ........... 424/133.1

(Continued)

FOREIGN PATENT DOCUMENTS

EP 0 137 280 4/1985

(Continued)

OTHER PUBLICATIONS

Radaev, Journal of Biological Chemistry, vol. 276(19), pp. 16478-16483, May 2001.*

(Continued)

*Primary Examiner* — Mark Navarro
*Assistant Examiner* — Ginny Portner

(57) ABSTRACT

Described herein are methods for the production of monoclonal antibodies in filamentous fungi host cells. The monoclonal antibodies are expressed as full-length fusion proteins that retain functional antigen binding and antibody-dependent cellular cytotoxicity capabilities. Improvements in the cleavage of the glucoamylase-light chain fusion protein to yield a mature antibody are also provided. The antibodies produced in filamentous fungi show equivalent pharmacokinetic disposition to antibodies produced in mammalian cells.

12 Claims, 10 Drawing Sheets

U.S. PATENT DOCUMENTS

| | | | | |
|---|---|---|---|---|
| 6,767,701 | B1 * | 7/2004 | Vind | 506/10 |
| 7,112,439 | B2 * | 9/2006 | Johnson et al. | 435/328 |
| 7,267,944 | B1 * | 9/2007 | Stuart | 435/6 |
| 2002/0061560 | A1 * | 5/2002 | Lawlis | 435/69.7 |
| 2002/0123057 | A1 * | 9/2002 | Zauderer et al. | 435/6 |
| 2003/0092131 | A1 * | 5/2003 | Ward et al. | 435/69.7 |
| 2003/0092164 | A1 * | 5/2003 | Gross et al. | 435/252.3 |
| 2003/0103986 | A1 * | 6/2003 | Rixon et al. | 424/178.1 |
| 2004/0018573 | A1 * | 1/2004 | Power et al. | 435/7.31 |
| 2004/0058403 | A1 * | 3/2004 | Harvey et al. | 435/7.32 |
| 2005/0260736 | A1 * | 11/2005 | Georgiou et al. | 435/252.3 |
| 2006/0024782 | A1 * | 2/2006 | Lehmbeck et al. | 435/69.1 |
| 2006/0029947 | A1 * | 2/2006 | Georgiou et al. | 435/6 |
| 2007/0065913 | A1 * | 3/2007 | Chen et al. | 435/69.1 |
| 2007/0099267 | A1 * | 5/2007 | Harvey et al. | 435/69.1 |
| 2009/0123921 | A1 * | 5/2009 | Georgiou et al. | 435/6 |
| 2009/0136936 | A1 * | 5/2009 | Georgiou et al. | 435/6 |
| 2009/0155257 | A1 * | 6/2009 | Adams et al. | 424/133.1 |

FOREIGN PATENT DOCUMENTS

| | | |
|---|---|---|
| EP | 0 215 594 B1 | 1/1995 |
| WO | WO 98/31821 | 7/1998 |
| WO | WO 00/23579 | 4/2000 |

OTHER PUBLICATIONS

Deshpande, N et al, Glycobiology, vol. 18(8), pp. 626-637, 2008, Protein glycosylation pathways in filamentous fungi.*

Alexopoulos, C.J., *Introductory Mycology*, New York: John Wiley & Sons, 1962.

Ausubel, F.M. et al., *Current Protocols in Molecular Biology*, eds. 1987 and 1993, John Wiley & Sons, New York, NY.

Ballance, D.J. et al., "Transformation of *Aspergillus nidulans* by the Orotidine-5'-Phosphate Decarboxylase Gene of *Neurospora crassa*," Biochemical and Biophysical Research Communications, 112(1): 284-289, 1983.

Barclay, Stephen L. et al., "Efficient Transformation of *Dictyostelium discoideum* Amoebae," Molecular and Cellular Biology, 3(12): 2117-2130, 1983.

Boel, E. et al., "Two different types of intervening sequences in the glucoamylase gene from *Aspergillus niger*," EMBO J., 3(7): 1581-1585, 1984.

Brenner, Charles et al., "Structural and enzymatic characterization of a purified prohormone-processing enzyme: Secreted, soluble Kex2 protease," Proc. Natl. Acad. Sci. USA, 89:922-926, 1992.

Broekhuijsen, M.P. et al., "Secretion of heterologous proteins by *Aspergillus niger*: Production of active human interleukin-6 in a protease-deficient mutant by KEX2-like processing of a glucoamylase-hIL6 fusion protein," J. of Biotechnology, 31:135-145, 1993.

Bull, John H. et al., "Heavily methylated amplified DNA in transformants of *Neurospora crassa*," Nature, 310: 701-704, 1984.

Campbell, Edward I. et al., "Improved transformation efficiency of *Aspergillus niger* using the homologous *nia*D gene for nitrate reductase," Curr. Genet., 16:53-56, 1989.

Carter, Paul et al., "Humanization of an anti-p185$^{HER2}$ antibody for human cancer therapy," Proc. Natl. Acad. Sci. USA, 89:4285-4289, 1992.

Case, Mary E. et al., "Efficient transformation of *Neurospora crassa* by utilizing hybrid plasmid DNA," Proc. Natl. Acad. Sci. USA, 76:5259-5263, 1979.

Coligan, J.E. et al., *Current Protocols in Immunology*, eds., 1991.

Contreras, Roland et al., "Efficient KEX2-Like Processing of a Glucoamylase-Interleukin-6 Fusion Protein by *Aspergillus nidulans* and Secretion of Mature Interleukin-6," Bio/Technology, 9:378-381, 1991.

Corrick, Catherine M. et al., "The nucleotide sequence of the *amd*S gene of *Aspergillus nidulans* and the molecular characterization of 5' mutations," Gene, 53:63-71, 1987.

Fowler, Timothy et al., "Regulation of the *glaA* of *Aspergillus niger*," Curr. Genet., 18:537-545, 1990.

Gems, D.H. et al., "Co-transformation with autonomously-replicating helper plasmids facilitates gene cloning from an *Aspergillus nidulans* gene library," Curr. Genet., 24:520-524, 1993.

Gwynne, David I. et al, "Genetically Engineered Secretion of Active Human Interferon and a Bacterial Endoglucanase from *Aspergillus nidulans*," Bio/Technology, 5:713-719, 1987.

Hale & Marham, *The Harper Collins Dictionary of Biology*, Harper Perennial, NY, 1991.

Hartingsveldt, W. et al., "Development of a homologous transformation system for *Aspergillus niger* based on the *pyrG* gene," Mol. Gen. Genet., 206:71-75, 1987.

Hynes, Michael J. et al., "Isolation of Genomic Clones Containing the *amdS* Gene of *Aspergillus nidulans* and Their Use in the Analysis of Structural and Regulatory Mutations," Molecular and Cellular Biology, 3(8):1430-1439, 1983.

Innis, M.A. et al., "Expression, Glycosylation, and Secretion of an *Aspergillus* Glucamylase by *Saccharomyces cerevisiae*," Science, 228:21-26, 1985.

Jalving, Ruud et al., "Characterization of the Kexin-Like Maturase of *Aspergillus niger*," Applied and Eviron. Microbiol., 66:363-368, 2000.

Jeenes, David J. et al., "A truncated glucoamylase gene fusion for heterologous protein secretion from *Aspergillus niger*," FEMS Microbiol. Letters, 107:267-272, 1993.

John, Marion A. et al., "Transformation of *Aspergillus nidulans* using the *argB* gene," Enzyme Microb. Technol., 6:386-389, 1984.

Johnstone, I.L. et al., "Cloning an *Aspergillus nidulans* developmental gene by transformation," EMBO Journal, 4:1307-1311, 1985.

Kelly, Joan M. et al., "Transformation of *Aspergillus niger* by the *amd*S gene," EMBO Journal, 4:475-479, 1985.

Kinsey, John A. et al., "Transformation of *Neurospora crassa* with the Cloned *am* (Glutamate Dehydrogenase) Gene," Molecular and Cellular Biology, 4:117-122, 1984.

Korman, David R. et al., "Cloning, characterization, and expression of two α-amylase genes from *Aspergillus niger* var. *awamori*," Curr. Genet., 17:203-212, 1990.

Kostelny, Sheri A. et al., "Humanization and Characterization of the Anti-HLA-DR Antibody 1D10," Int. J. Cancer, 93:556-565, 2001.

Libby, Carol Baker et al., "Effect of amino acid deletions in the *O*-glycosylated region of *Aspergillus awamori* glucoamylase," Protein Engineering, 7:1109-1114, 1994.

Lockington, Robin A. et al., "Cloning and characterization of the ethanol utilization regulon in *Aspergillus nidulans*," Gene, 33:137-149, 1985.

Marston, Fiona A.O., "The purification of eukaryotic polypeptides synthesized in *Escherichia coli*," Biochem. J., 240:1-12, 1986.

McKnight, Gary L. et al., "Nucleotide Sequence of the Triosephosphate Isomerase Gene from *Aspergillus nidulans*: Implications for a Differential Loss of Introns," Cell, 46:143-147, 1986.

Mullaney, Edward J. et al., "Primary structure of the *trpC* gene from *Aspergillus nidulans*," Mol. Gen. Genet., 199:37-45, 1985.

Nunberg, Jack H. et al., "Molecular Cloning and Characterization of the Glucoamylase Gene of *Aspergillus awamori*," 4:2306-2315, 1984.

Nyyssönen, Eini et al., "Efficient Production of Antibody Fragments by the Filamentous Fungus *Trichoderma reesei*," Bio/Technology, 11:591-595, 1993.

Nyyssonen, Eini et al., "Protein production by the filamentous fungus *Trichoderma reesei*: secretion of active antibody molecules," Canadian Journal of Botany, vol. 73, suppl. 1, pp. S885-S890, 1995.

Pennel, C.A. et al., "In Vitro production of recombinant antibody fragments in *Pichia pastoris*," Res. Immunol., 149:599-603, 1998.

Roberts, Ian N. et al., "Heterologous gene expression in *Aspergillus niger*: a glucoamylase-porcine pancreatic prophospholipase $A_2$ fusion protein is secreted and processed to yield mature enzyme," Gene, 122:155-161, 1992.

Sambrook et al., *Molecular Cloning: A Laboratory Manual*, 2$^{nd}$ ed., 1989.

Singleton et al., *Dictionary of Microbiology and Molecular Biology*, 2$^{nd}$ ed., John Wiley & Sons, New York, 1994.

Spencer, Andrew J. et al., "Determinants of the fidelity of processing glucoamylase-lysozyme fusions by *Aspergillus niger*," Eur J. Biochem., 258:107-112, 1998.

Tilbum, Joan et al., "Transformation by integration in *Aspergillus nidulans*," Gene, 26:205-221, 1983.
Towbin, Harry et al., "Electrophoretic transfer of proteins from polyacrylamide gels to nitrocellulose sheets: Procedure and some applications," Proc. Natl. Acad. Sci. USA, 76(9): 4350-4354, 1979.
Tsuchiya, Kozo et al., "High Level Secretion of Calf Chymosin Using a Glucoamylase-prochymosin Fusion Gene in *Aspergillus oryzae*," Biosci. Biotech. Biochem., 58(5):895-899, 1994.
Verma, R. et al., "Antibody engineering: Comparison of bacterial, yeast, insect and mammalian expression systems," J. Immunol. Meth., 216:165-181, 1998.
Vermes, István et al., "A novel assay for apoptosis Flow cytometric detection of phosphatidylserine expression on early apoptotic cells using fluorescein labelled Annexin V," J. Immunol. Meth., 184:39-51, 1995.
Ward, Michael et al., "Improved Production of Chymosin in *Aspergillus* by Expression as a Glucoamylase-Chymosin Fusion," Bio/Technology, 8:435-440, 1990.
Ward, Michael et al., "Use of *Aspergillus* overproducing mutants, cured for integrated plasmid, to overproduce heterologous proteins," Appl. Microbiol. Biotechnol., 39:738-743, 1993.
Ward, Pauline P., "A System for Production of Commercial Quantities of Human Lactoferrin: A Broad Spectrum Natural Antibiotic," Bio/Technology, 13:498-502, 1995.
Yelton, M. Melanie et al., "Transformation of *Aspergillus nidulans* by using a *trpC* plasmid," Proc. Natl. Acad. Sci. USA, 81:1470-1474, 1984.
PCT International Search Report for PCT/US03/12246.

* cited by examiner

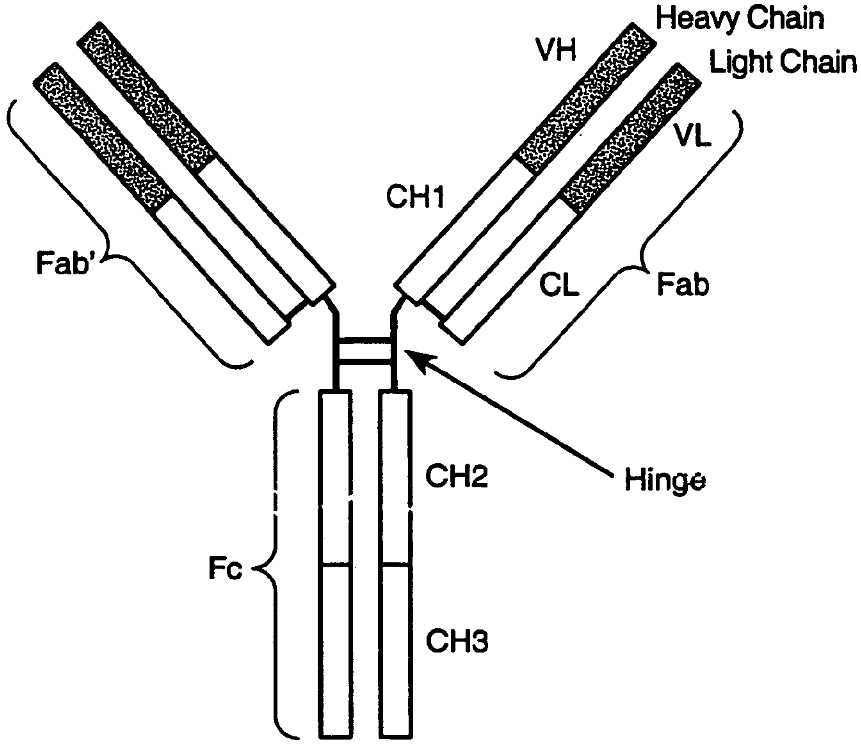
*FIG._1*
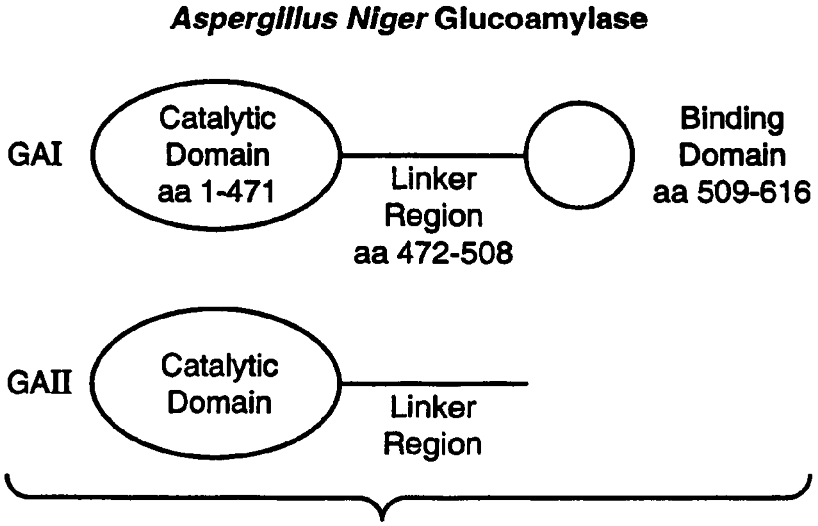
*FIG._2*

FIG._3
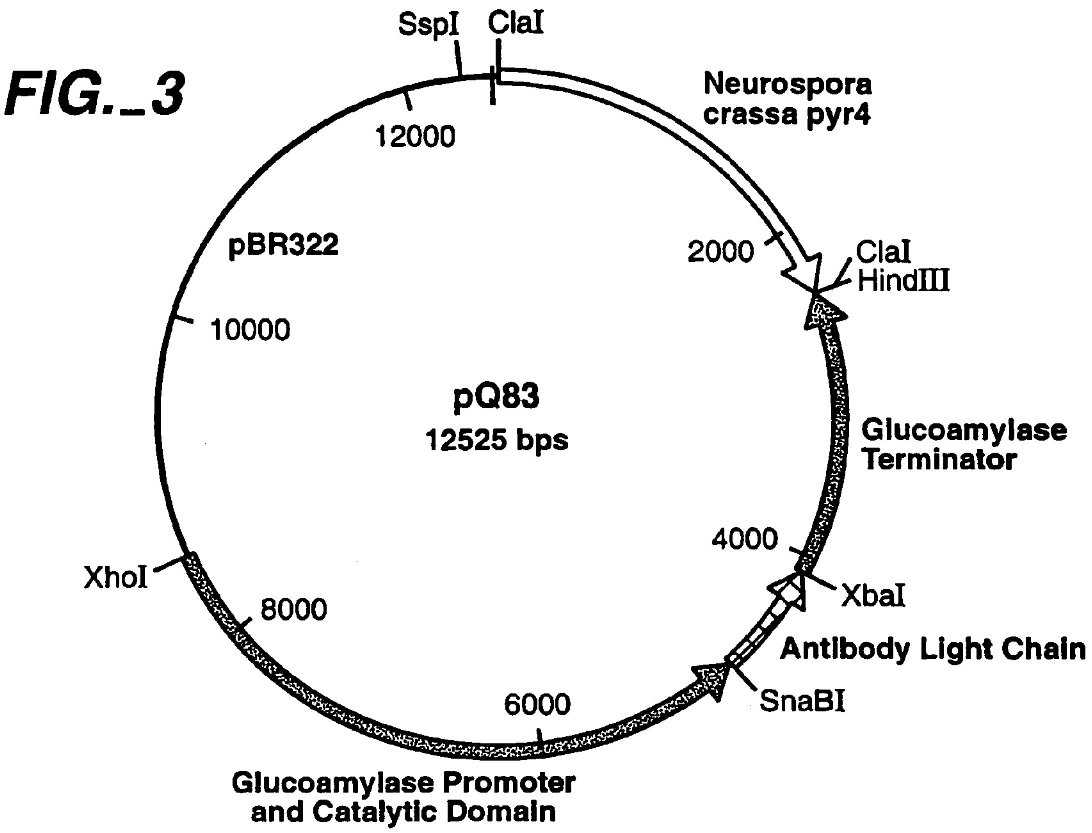
FIG._4
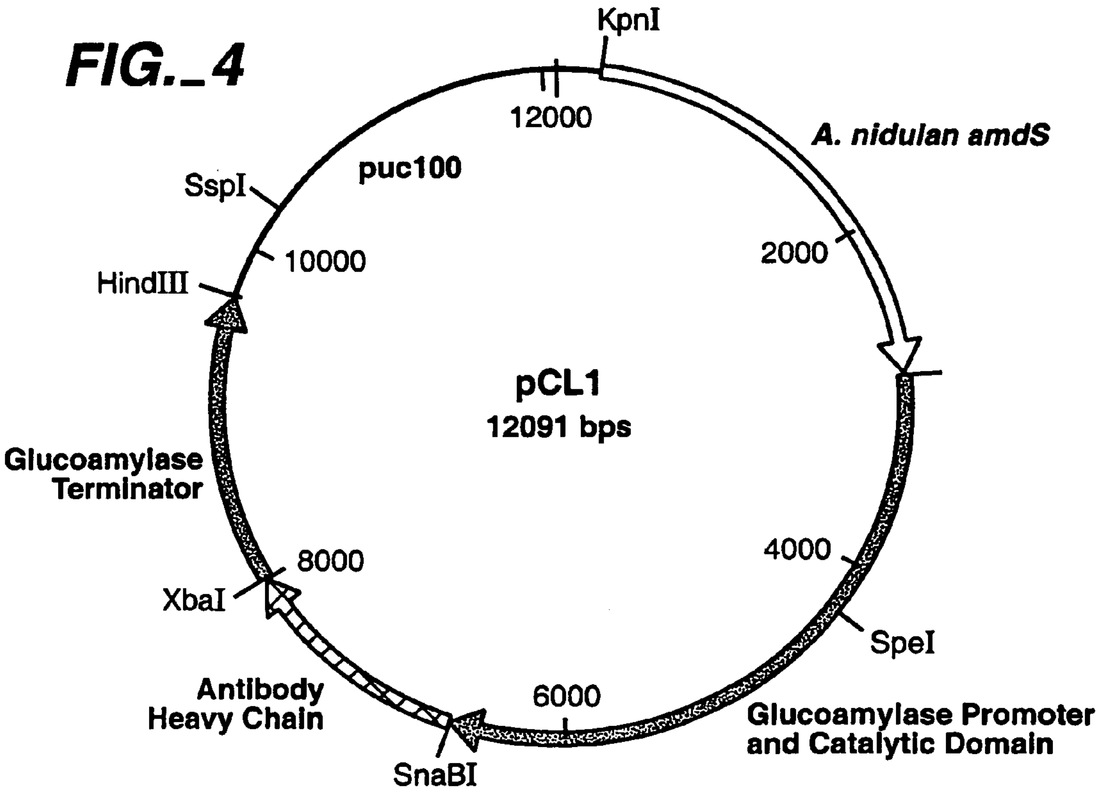

FIG._5
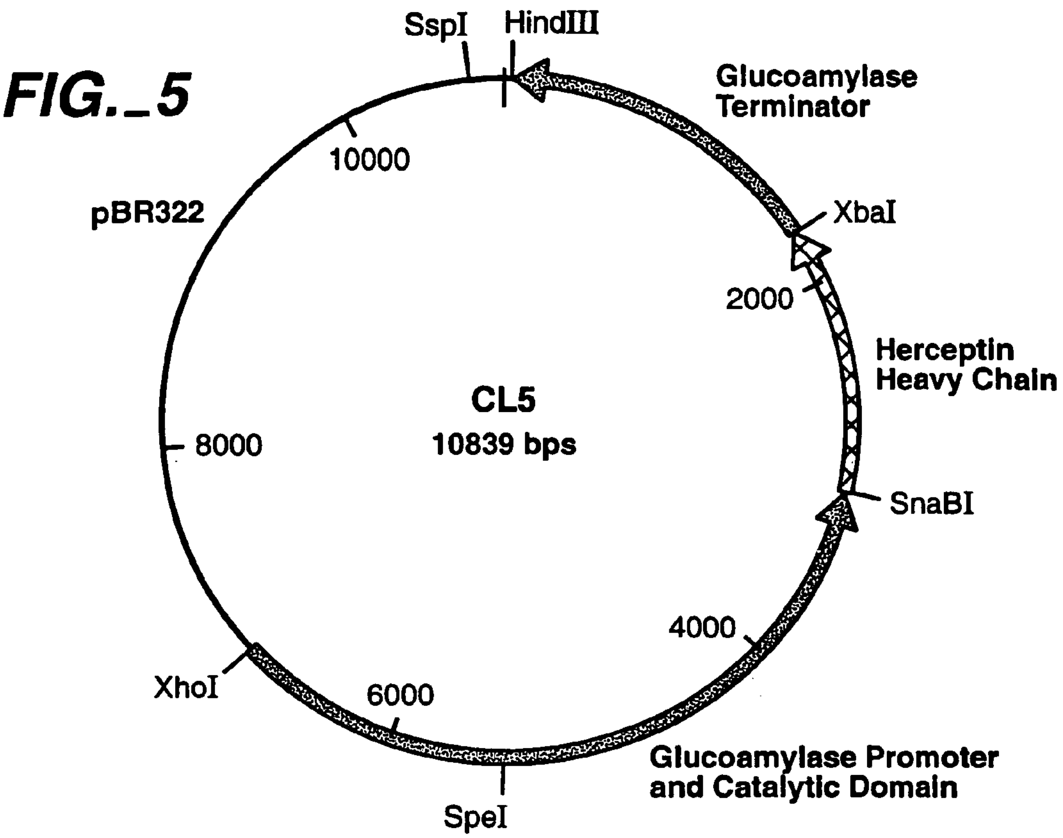
FIG._6
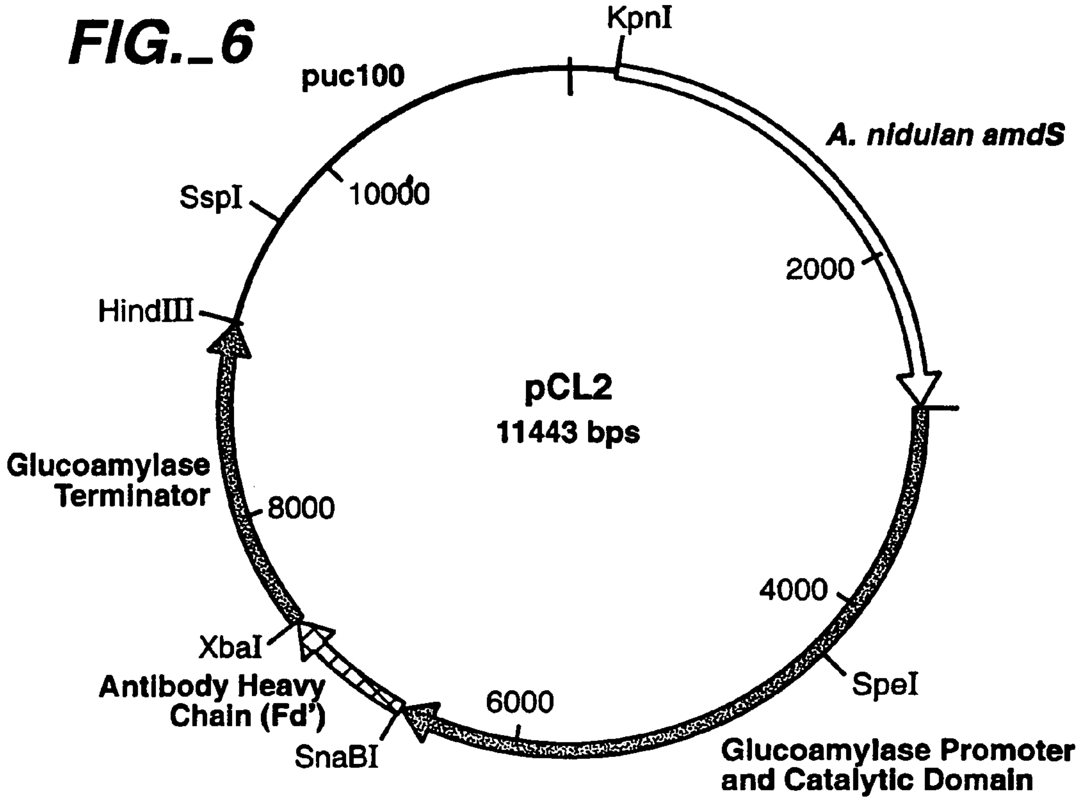

FIG._7
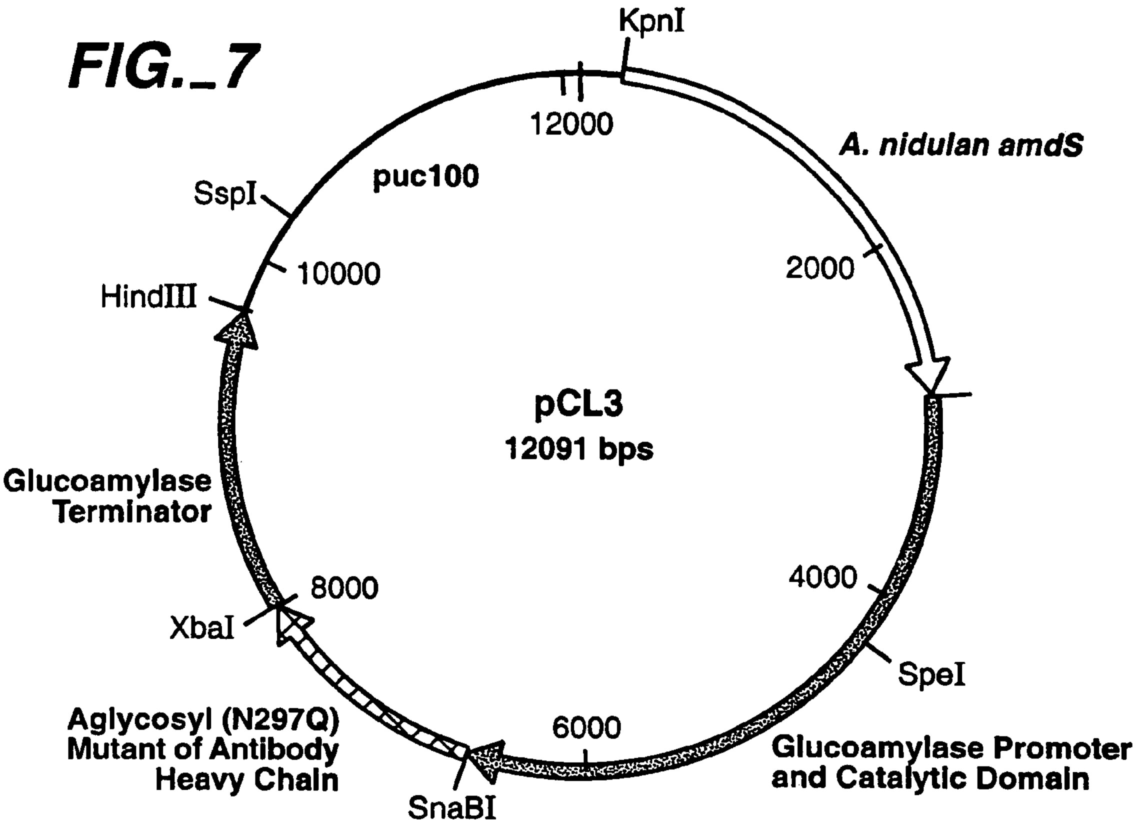

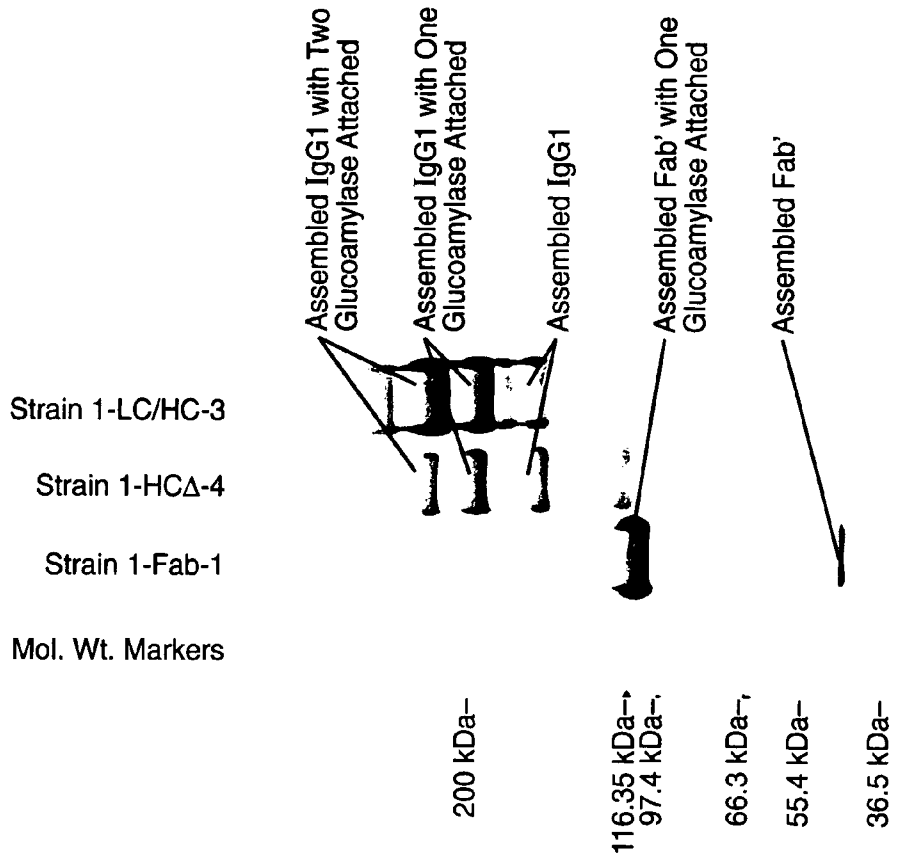
FIG._9
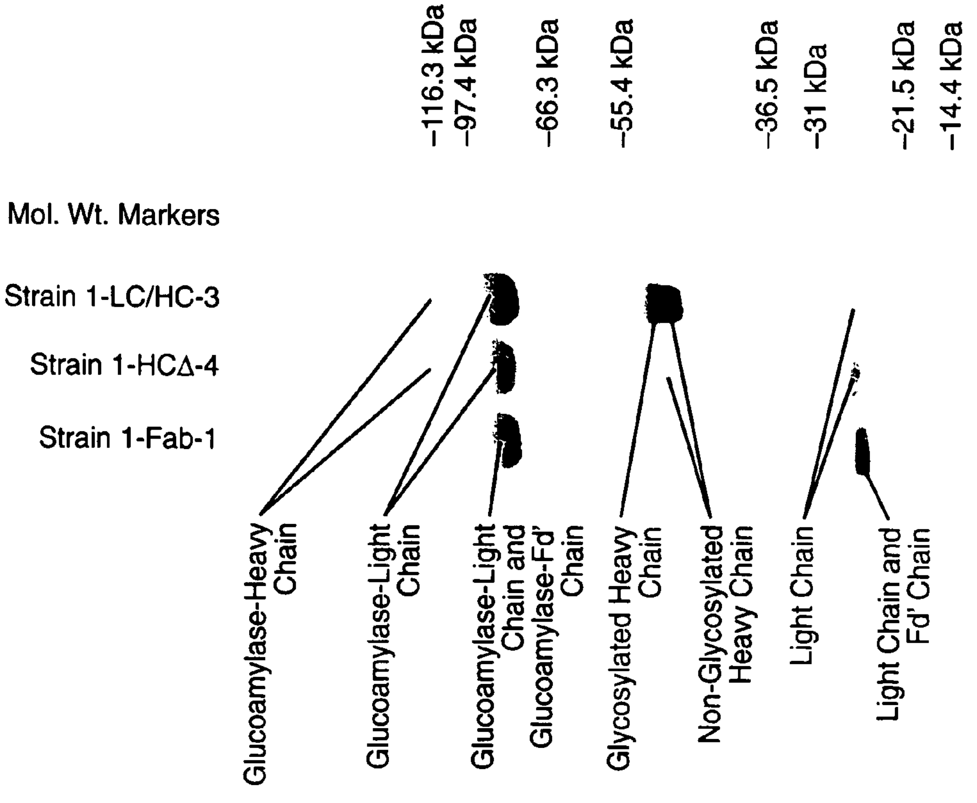
FIG._8

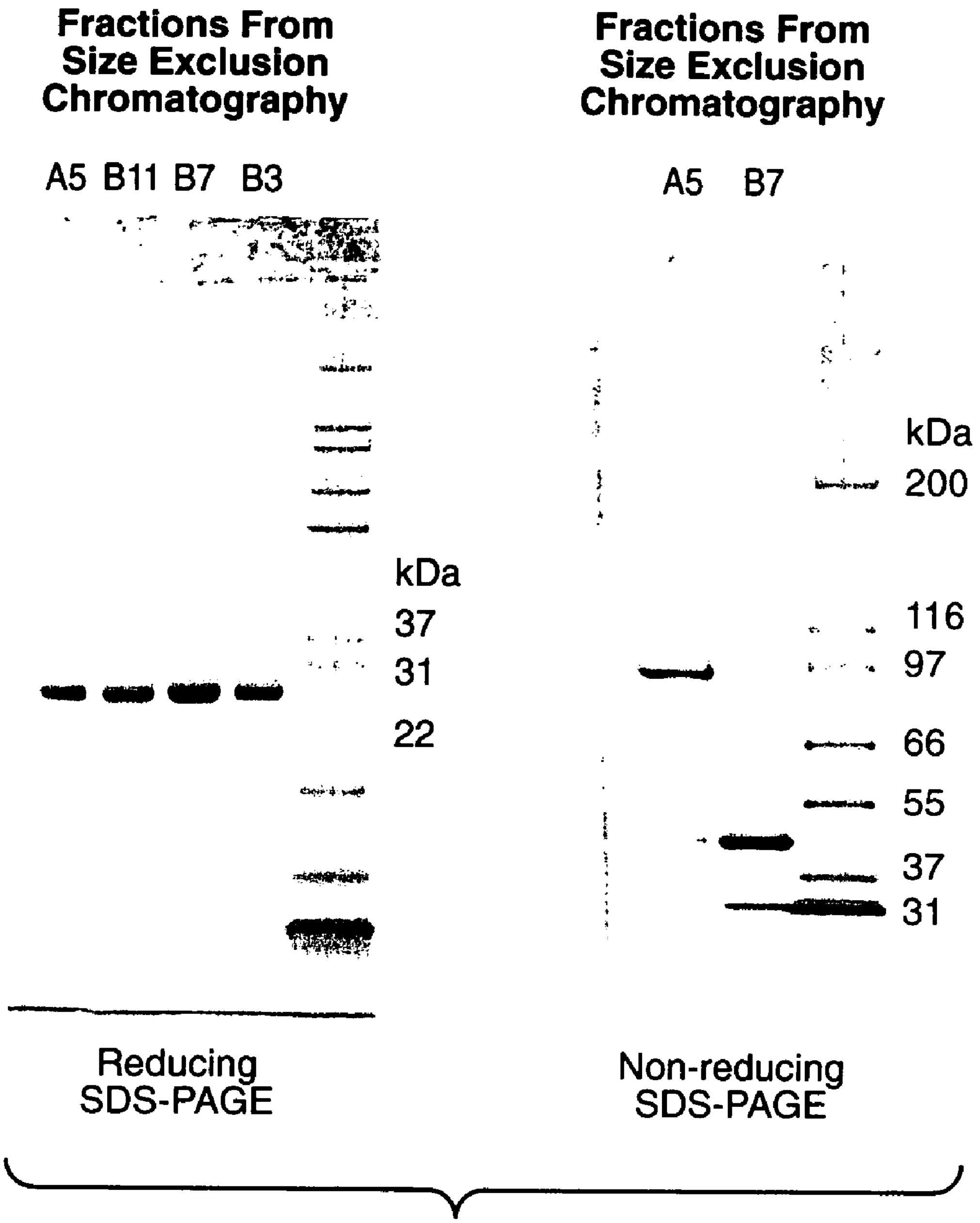
FIG._10

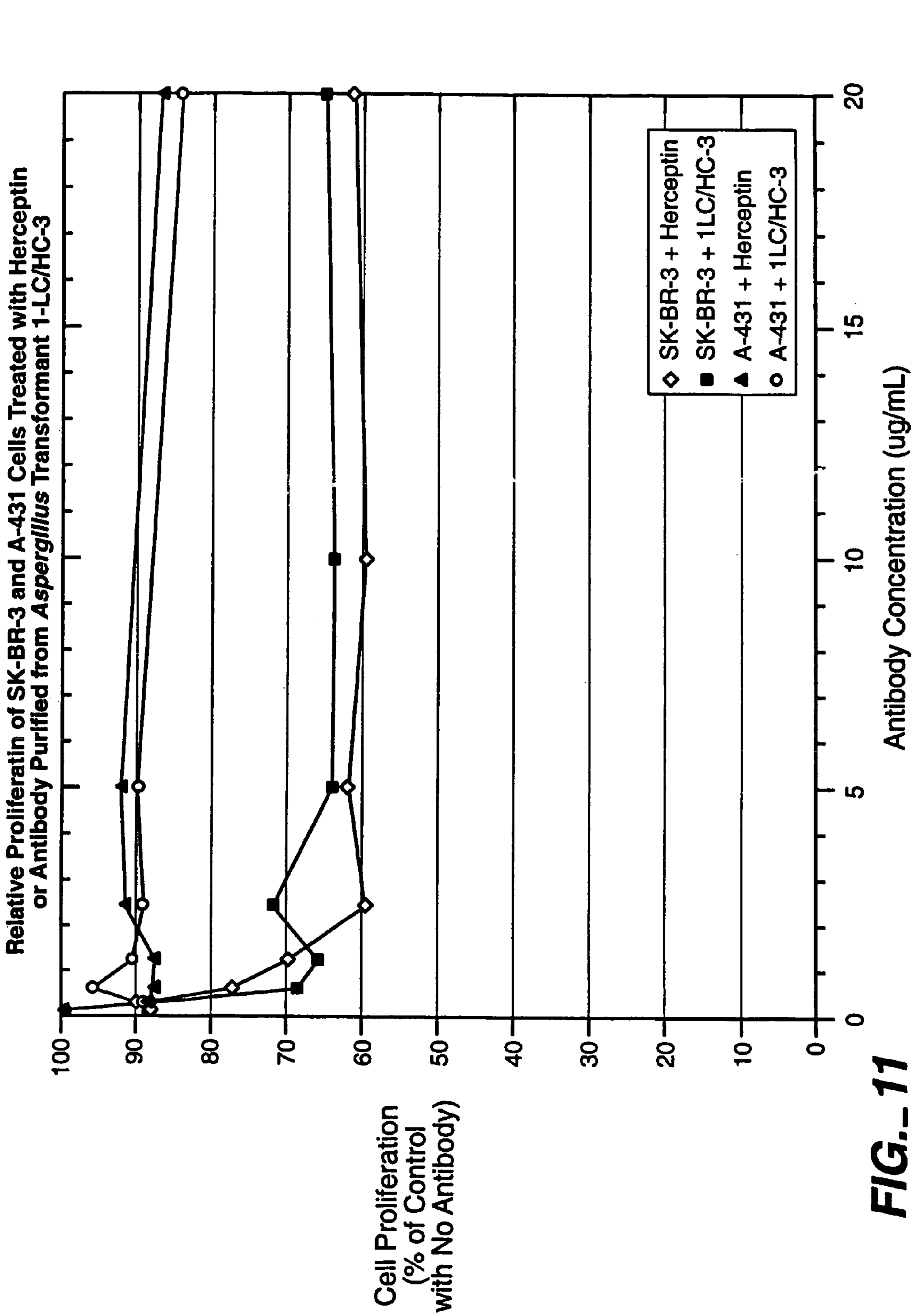
FIG._11

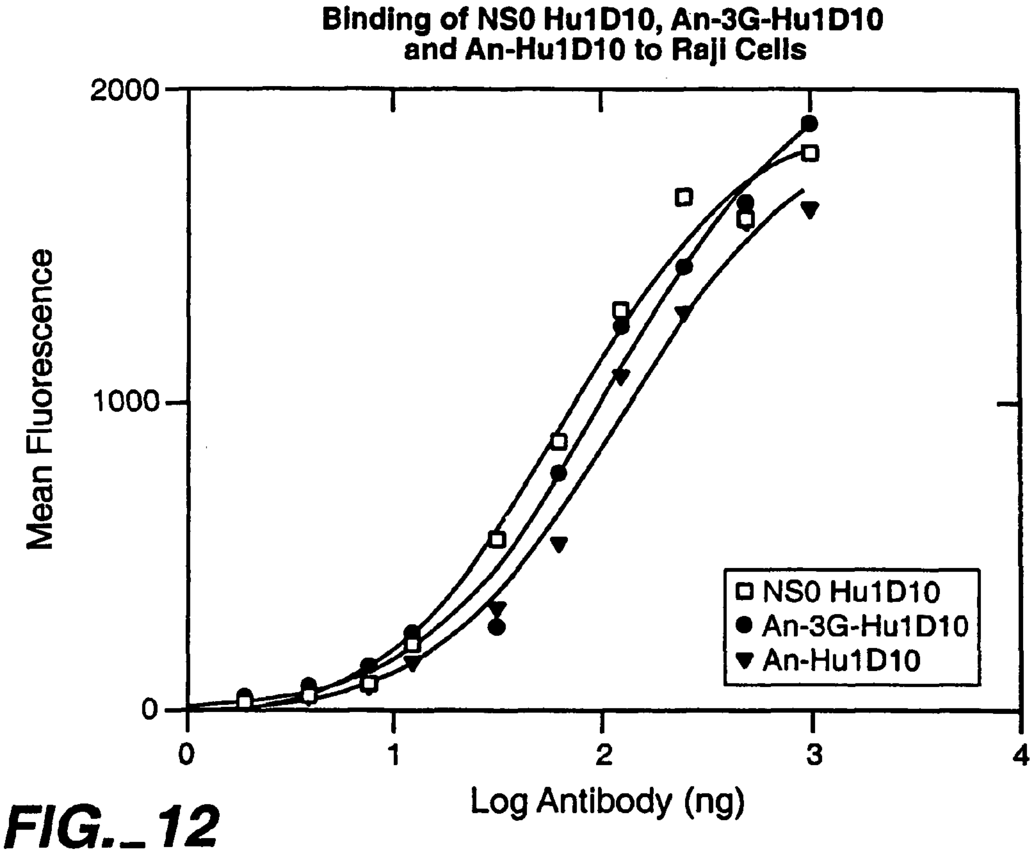
FIG._12
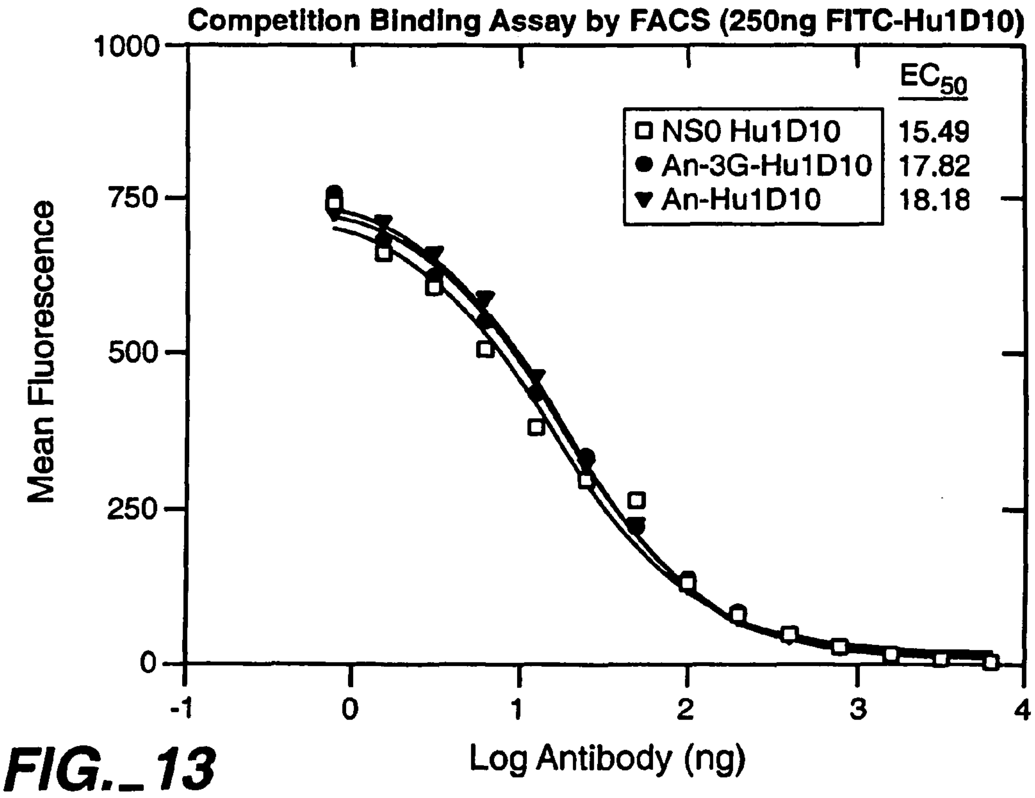
FIG._13

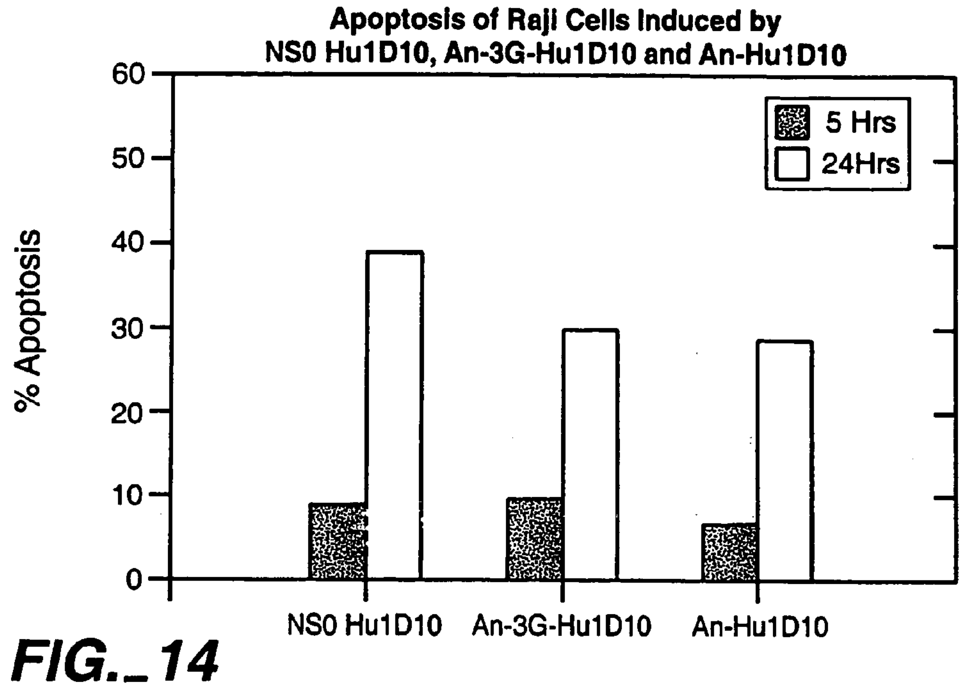
FIG._14
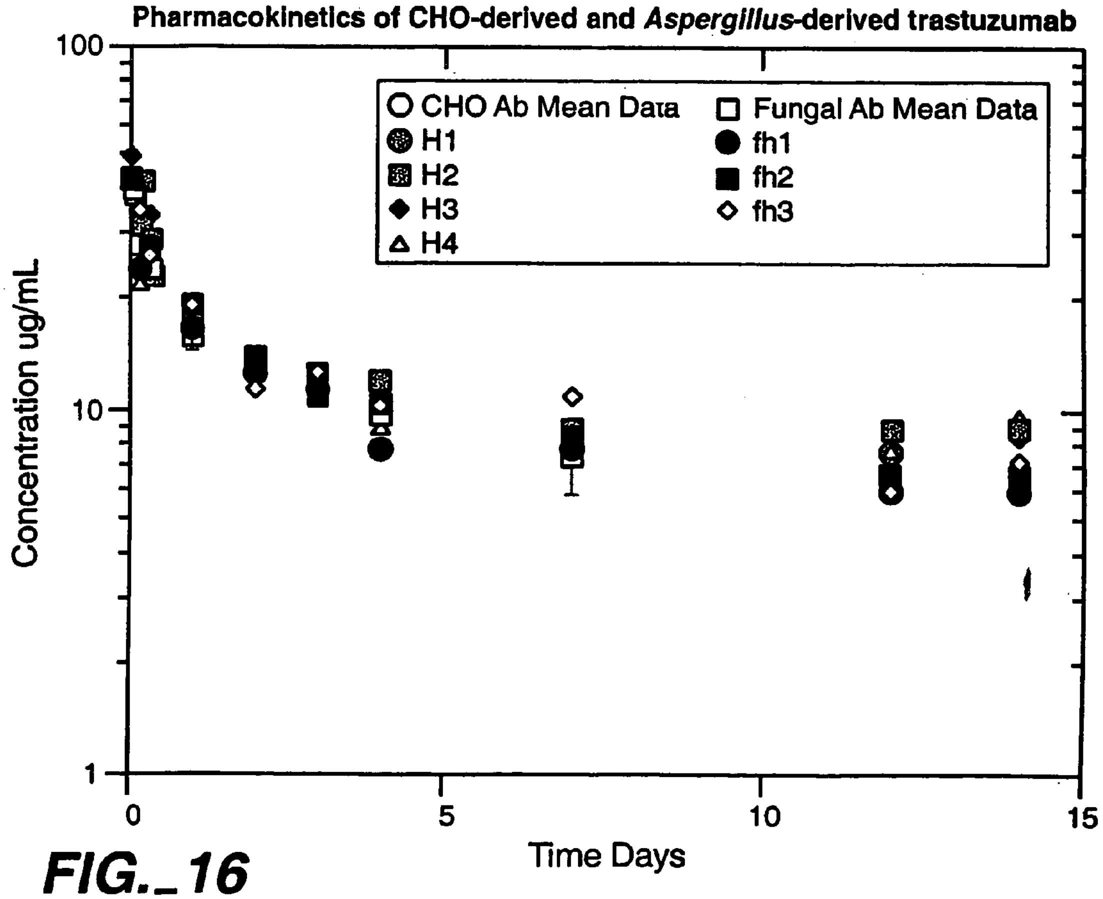
FIG._16

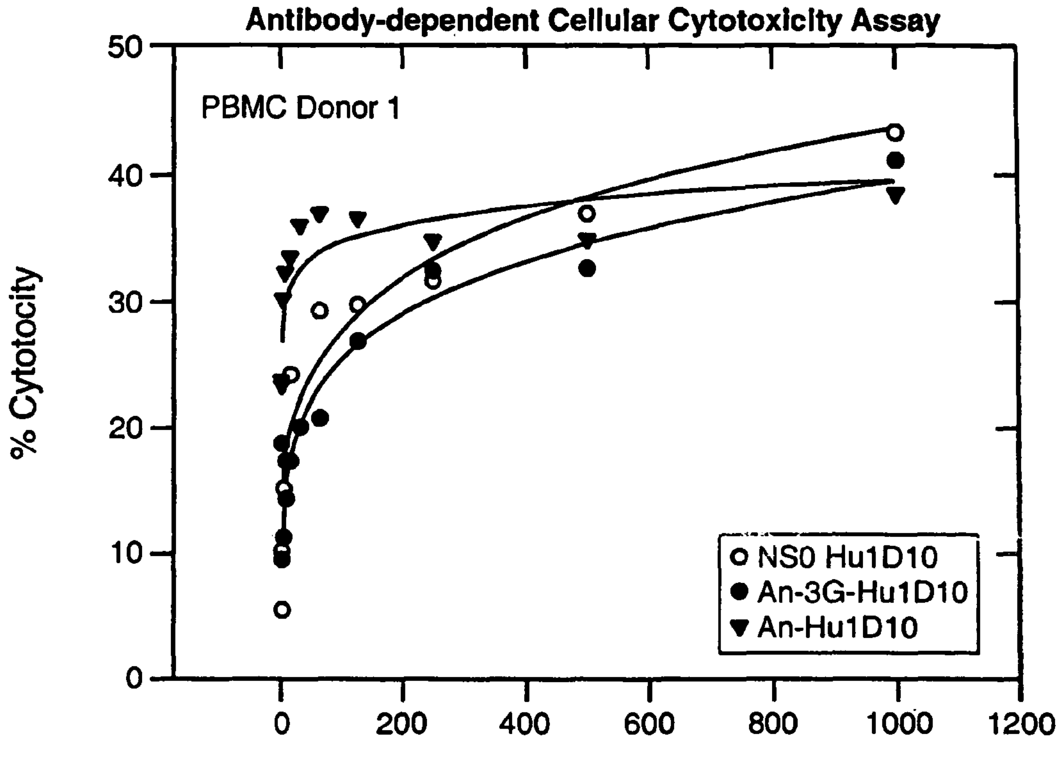
FIG._15A
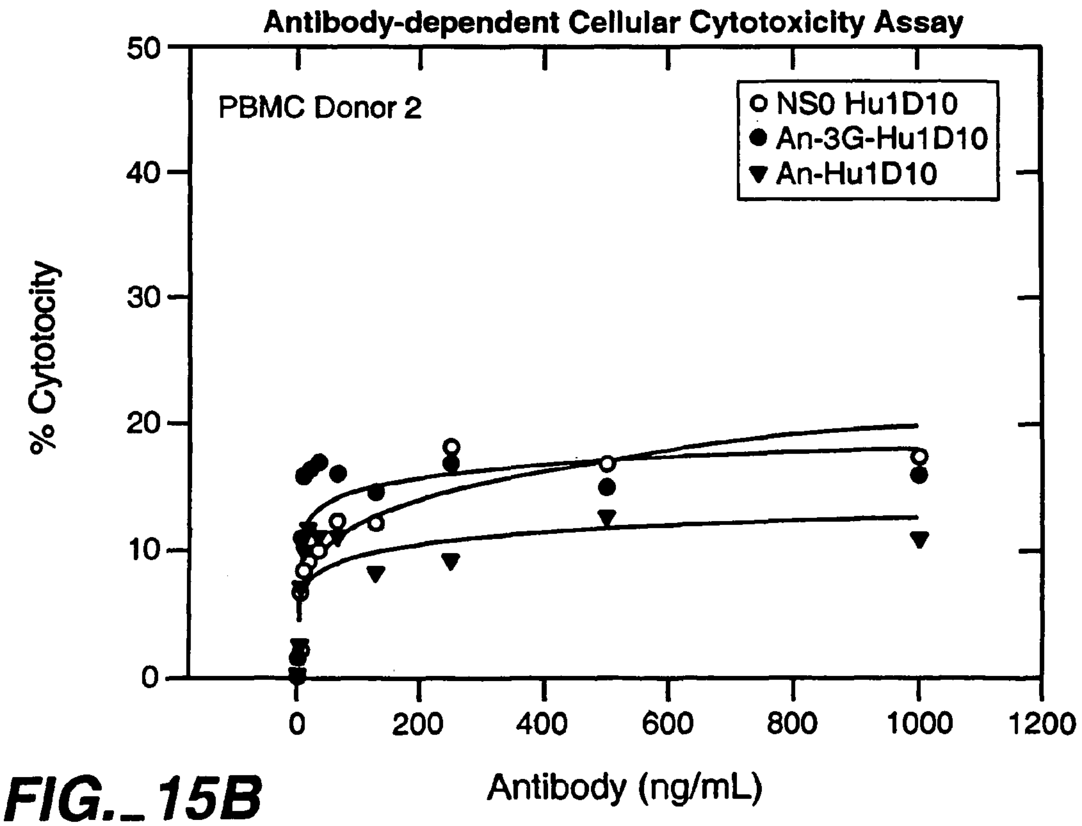
FIG._15B

PRODUCTION OF FUNCTIONAL ANTIBODIES IN FILAMENTOUS FUNGI

RELATED APPLICATIONS

This is a divisional of application of Ser. No. 10/418,836, now abandoned which claims priority to application No. 60/373,889, filed Apr. 18, 2002; application No. 60/411,540, filed Sep. 18, 2002; application No. 60/411,537, filed Sep. 18, 2002, and application No. 60/452,134, filed Mar. 4, 2003.

FIELD OF THE INVENTION

The present invention is directed to increased secretion of immunoglobulins from filamentous fungi. The invention discloses fusion nucleic acids, vectors, fusion polypeptides, and processes for obtaining the immunoglobulins.

BACKGROUND OF THE INVENTION

Production of fusion polypeptides has been reported in a number of organisms, including *E. coli*, yeast, and filamentous fungi. For example, bovine chymosin and porcine pancreatic prophospholipase $A_2$ have both been produced in *Aspergillus niger* or *Aspergillus niger* var. *awamori* (previously known as *Aspergillus awamon*) as fusions to full-length glucoamylase (GAI) (U.S. Pat. No. 5,679,543; Ward et al., Bio/technology 8:435-440, 1990; Roberts et al., Gene 122: 155-161, 1992). Human interleukin 6 (hIL6) has been produced in *A. nidulans* as a fusion to full-length *A. niger* GAI (Contreras et al., Biotechnology 9:378-381, 1991). Hen egg white lysozyme (Jeenes et al., FEMS Microbiol. Lett. 107: 267-272, 1993) and human lactoferrin (Ward et al., Bio/technology 13:498-503, 1995) have been produced in *A. niger* as fusions to residues 1498 of glucoamylase and hIL6 has been produced in *A. niger* as a fusion to glucoamylase residues 1-514 (Broekhuijsen et al., J. Biotechnol. 31:135-145, 1993). In some of the above experiments (Contreras et al., 1991; Broekhuijsen et al., 1993; Ward et al., 1995) a KEX2 protease recognition site (Lys, Arg) has been inserted between glucoamylase and the desired polypeptide to allow in vivo release of the desired polypeptide from the fusion protein as a result of the action of a native *Aspergillus* KEX2-like protease (the *Aspergillus* KEX2-like protease is now designated KEXB).

Additionally, bovine chymosin has been produced in *A. niger* var. *awamori* as a fusion with full-length native alpha-amylase (Korman et al., Curr. Genet. 17:203-212, 1990) and in *A. oryzae* as a fusion with truncated forms of *A. oryzae* glucoamylase (either residues 1-603 or 1-511; Tsuchiya et al., Biosci. Biotech. Biochem. 58:895-899, 1994).

A small protein (epidermal growth hormone; 53 amino acids) has been produced in *Aspergillus* as a tandem fusion of three copies of the protein (U.S. Pat. No. 5,218,093). The trimer of EGF was secreted as a result of the inclusion of an N-terminal secretion signal sequence. However, the EGF molecules were not additionally fused to a protein efficiently secreted by filamentous fungi and no method for subsequent separation of monomeric EGF proteins was provided.

The glaA gene encodes glucoamylase which is highly expressed in many strains of *Aspergillus niger* and *Aspergillus niger* var. *awamori*. The promoter and secretion signal sequence of the gene have been used to express heterologous genes in *Aspergilli* including bovine chymosin in *Aspergillus nidulans* and *A. niger* var. *awamori* as previously described (Cullen, D. et al., (1987) Bio/Technology 5, 713-719 and EPO Publication No. 0 215 594). In the latter experiments, a variety of constructs were made, incorporating prochymosin cDNA, either the glucoamylase or the chymosin secretion signal and, in one case, the first 11 codons of mature glucoamylase. Maximum yields of secreted chymosin obtained from *A. awamori* were below 15 mg/l in 50 ml shake flask cultures and were obtained using the chymosin signal sequence encoded by pGRG3. These previous studies indicated that integrated plasmid copy number did not correlate with chymosin yields. Abundant polyadenylated chymosin mRNA was produced, and intracellular levels of chymosin were high in some transformants regardless of the source of secretion signal. It was inferred that transcription was not a limiting factor in chymosin production but that secretion may have been inefficient. It was also evident that the addition of a small amino terminal segment (11 amino acids) of glucoamylase to the propeptide of prochymosin did not prevent activation to mature chymosin. The amount of extracellular chymosin obtained with the first eleven codons of glucoamylase, however, was substantially less than that obtained when the glucoamylase signal was used alone. Subsequently, it was demonstrated that chymosin production could be greatly increased when a fusion protein consisting of full-length glucoamylase and prochymosin was produced (U.S. Ser. No. 08/318,494; Ward et al. Bio/technology 8:435-440, 1990).

*Aspergillus niger* and *Aspergillus niger* var. *awamori* (*A. awamon*) glucoamylases have identical amino acid sequences. The glucoamylase is initially synthesized as preproglucoamylase. The pre and pro regions are removed during the secretion process so that mature glucoamylase is released to the external medium. Two forms of mature glucoamylase are recognized in culture supernatants: GAI is the full-length form (amino acid residues 1-616) and GAII is a natural proteolytic fragment comprising amino acid residues 1-512. GAI is known to fold as two separate domains joined by an extended linker region. The two domains are the 471 residue catalytic domain (amino acids 1-471) and the 108 residue starch binding domain (amino acids 509-616), the linker region being 36 residues in length (amino acids 472-508). GAII lacks the starch binding domain. These details of glucoamylase structure are reviewed by Libby et al. (Protein Engineering 7:1109-1114, 1994) and are shown diagrammatically in FIG. 2.

*Trichoderma reesei* produces several cellulase enzymes, including cellobiohydrolase I (CBHI), which are folded into two separate domains (catalytic and binding domains) separated by an extended linker region. Foreign polypeptides have been secreted in *T. reesei* as fusions with the catalytic domain plus linker region of CBHI (Nyyssonen et al., Bio/technology 11:591-595, 1993).

Antibody production has been, to date, preferably performed in transgenic animals, mammalian cell culture or plants. Each of these methods suffers from one or more drawbacks. For example, transgenic animals and mammalian cell cultures each have a risk of being contaminated by viral or other adventitious agents, e.g., prions. In addition, the ability to scale up any one of these production systems is limited. Recombinant plants may take approximately ten months to produce a recombinant protein, while mammalian cells may take about three months. Thus, there remains a need for alternative methods for antibody production.

SUMMARY OF THE INVENTION

Provided herein are nucleic acids, cells and methods for the production of immunoglobulins.

In a first embodiment, nucleic acids encoding a functional monoclonal immunoglobulin are provided. In one aspect, a nucleic acid comprising regulatory sequences operatively linked to a first, second, third and fourth nucleic acid sequences are provided. Terminator sequences are optionally provided following the fourth nucleic acid sequence. In a second aspect, the first nucleic acid sequence encodes a signal polypeptide functional as a secretory sequence in a first filamentous fungus, the second nucleic acid encodes a secreted polypeptide or functional portion thereof normally secreted from said first or a second filamentous fungus, the third nucleic acid encodes a cleavable linker and the fourth nucleic acid encodes an immunoglobulin chain or fragment thereof.

In a third aspect, an expression cassette comprising nucleic acid sequences encoding an immunoglobulin chain is provided.

In a second embodiment, methods of expressing a functional monoclonal antibody are provided. In one aspect, a host cell is (i) transformed with a first expression cassette comprising a nucleic acid sequence encoding a first immunoglobulin chain, (ii) transformed with a second expression cassette comprising a nucleic acid sequence encoding a second immunoglobulin chain, and (iii) cultured under appropriate conditions to express the immunoglobulin chains. Optionally, the immunoglobulin chains may be recovered. In one aspect, the immunoglobulin chains are expressed as a fusion protein. The expressed fusion immunoglobulin chains are subsequently assembled as functional antibodies and secreted.

In a third embodiment, cells capable of expressing an immunoglobulin are provided. Host cells are transformed with two expression cassettes, a first expression cassette encoding a first immunoglobulin chain type (e.g., either a heavy or light chain) and a second expression cassette encoding a second immunoglobulin chain type (e.g., either light or heavy chain, respectively). The heavy chain may be of any immunoglobulin class.

In a fourth embodiment, a functional monoclonal immunoglobulin is provided. In one aspect, the functional monoclonal antibody chains are expressed as fusion proteins consisting of the glucoamylase signal sequence, prosequence, catalytic domain and linker region up to amino acid number 502 of mature glucoamylase, followed by amino acids YKR and then by the mature immunoglobulin chain. One chain may be either the heavy or light chain.

In a second aspect, the fully assembled antibodies are treated with a protease to liberate an immunoglobulin from the fusion protein. In a third aspect, the antibodies may be treated with a deglycosylating enzyme.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE FIGURES

FIG. 1 shows a schematic representation of an antibody. Indicated on the drawing are the various regions of the antibody and the names of various antibody fragments.

FIG. 2 is a diagram depicting the two forms of glucoamylase from *Aspergillus niger* or *Aspergillus niger* var. *awamori.*

FIG. 3 is a diagram of plasmid pQ83.

FIG. 4 is a diagram of plasmid pCL1.

FIG. 5 is a diagram of pCL5, a second trastuzumab heavy chain expression plasmid.

FIG. 6 is a diagram of plasmid pCL2.

FIG. 7 is a diagram of plasmid pCL3.

FIG. 8 shows the results of SDS-PAGE under reducing conditions and with Coomassie Brilliant Blue staining of samples which had been purified by protein A chromatography. The bands observed for transformant 1-LC/HC-3 (lane 3) were identified as the light chain (25 kDa), non-glycosylated and glycosylated forms of the heavy chain (50 and 53 kDa), glucoamylase-light chain fusion protein (85 kDa) and glucoamylase-heavy chain fusion (116 kDa). The bands observed for transformant 1-HCA-4 (lane 2) were identified as the light chain (25 kDa), non-glycosylated form of the heavy chain (50 kDa), glucoamylase-light chain fusion protein (85 kDa) and glucoamylase-heavy chain fusion (116 kDa). The bands observed for transformant 1-Fab-1 (lane 1) were identified as the light chain and Fd' chain (both 25 kDa) and the glucoamylase-light chain and glucoamylase-Fd' fusion proteins (both 85 kDa).

FIG. 9 shows the results of SDS-PAGE (NuPAGE Tris-Acetate Electrophoresis System from Invitrogen Corporation, Carlsbad, Calif.) under non-reducing conditions and with Coomassie Brilliant Blue staining of samples which had been purified by protein A chromatography. The major bands observed for transformant 1-LC/HC-3 (lane 4) were identified as assembled IgG1 (150 kDa), assembled IgG1 with one molecule of glucoamylase attached (~200 kDa) and assembled IgG1 with two molecules of glucoamylase attached (~250 kDa). The major bands observed for transformant 1-HCΔ-4 (lane 3) were identified as assembled IgG1 (150 kDa), assembled IgG1 with one molecule of glucoamylase attached (~200 kDa) and assembled IgG1 with two molecules of glucoamylase attached (~250 kDa). The major bands observed for transformant 1-Fab-1 (lane 2) were identified as assembled Fab' (50 kDa) and assembled Fab' with one molecule of glucoamylase attached (~100 kDa).

FIG. 10 shows the results of SDS-PAGE under reducing and non-reducing conditions of samples of Fab' and F(ab')2 purified from supernatant of transformant 1-Fab-12 by hydrophobic charge induction chromatography followed by size exclusion chromatography. A5, B11, B7 and B3 represent different fractions collected from the size exclusion chromatography column.

FIG. 11 is a graph showing the anti-proliferative effect of the HER2 antibodies on human breast adenocarcinoma cell line, SK-BR-3 (ATCC number: HTB-30). Commercial Herceptin antibodies are indicated by diamonds (♦) and triangles (▲). *Aspergillus* transformant 1 LC/HC-3 antibodies are indicated by circles (●) and squares (■). Control cells were A-431, a human epidermoid carcinoma that expresses high levels of the EGF receptor and low levels of HER2.

FIG. 12 is a graph showing the binding of Hu1D10 antibody derived from NS0 mouse myeloma cell line (squares; ■), and two *Aspergillus* produced antibodies (designated as An-3G-Hu1D10 [circles; ●] and An-Hu1D10 [inverted triangles; ▼]) to Raji cells. No significant difference in binding was observed.

FIG. 13 is a graph showing the competitive binding of FITC-labeled antibody with Hu1D10 antibody derived from NS0 mouse myeloma cell line (squares; ■), and two *Aspergillus* produced antibodies (An-3G-Hu1D10 [circles; ●] and An-Hu1D10 [inverted triangles; ▼]) to Raji cells. No significant difference in binding was observed.

FIG. 14 is a bar graph indicating the percentage of cells in which apoptosis has been induced by Hu1D10, An-3G-

Hu1D10 and An-Hu1D10 at 5 hours or 24 hours. No significant difference in inducing apoptosis was observed.

FIGS. 15 A and B are graphs depicting the levels of Antibody-Dependent Cellular Cytotoxicity reached by each of the three antibodies tested, i.e., Hu1D10, An-3G-Hu1D10 and An-Hu1D10, in two different donors. Clear indication of ADCC activity by *Aspergillus*-derived antibodies is exhibited.

FIG. 16 is a graph of the in vivo pharmacokinetics of CHO-derived and *Aspergillus*-derived trastuzumab. No significant difference in pharmacokinetic disposition was observed for the fungal-derived antibody.

DETAILED DESCRIPTION OF THE INVENTION

The inventors have discovered that desired antibodies can be expressed and secreted in filamentous fungi at levels higher than that previously obtained using other expression systems.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., Dictionary of Microbiology and Molecular Biology, 2d Ed., John Wiley and Sons, New York (1994), and Hale & Marham, The Harper Collins Dictionary of Biology, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

DEFINITIONS

The terms "isolated" or "purified" as used herein refer to a nucleic acid or amino acid or polypeptide that is removed from at least one component with which it is naturally associated.

An "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. Expression cassette may be used interchangeably with DNA construct and its grammatical equivalents.

As used herein, the term "vector" refers to a nucleic acid construct designed for transfer nucleic acid sequences into cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "plasmid" refers to a circular double-stranded (ds) DNA construct used as a cloning vector, and which forms an extrachromosomal self-replicating genetic element in some eukaryotes.

The term "nucleic acid molecule" or "nucleic acid sequence" includes RNA, DNA and cDNA molecules. It will be understood that, as a result of the degeneracy of the genetic code, a multitude of nucleotide sequences encoding a given protein may be produced.

As used herein, a "fusion DNA sequence" comprises from 5' to 3' first, second, third and fourth DNA sequences.

As used herein, "a first nucleic acid sequence" or "first DNA sequence" encodes a signal peptide functional as a secretory sequence in a first filamentous fungus. Such signal sequences include those from glucoamylase, α-amylase and aspartyl proteases from *Aspergillus niger* var. *awamori, Aspergillus niger, Aspergillus oryzae*, signal sequences from cellobiohydrolase I, cellobiohydrolase II, endoglucanase I, endoglucanase III from *Trichoderma*, signal sequences from glucoamylase from *Neurospora* and *Humicola* as well as signal sequences from eukaryotes including the signal sequence from bovine chymosin, human tissue plasminogen activator, human interferon and synthetic consensus eukaryotic signal sequences such as that described by Gwynne et al., (1987) *Bio/Technology* 5, 713-719. Particularly preferred signal sequences are those derived from polypeptides secreted by the expression host used to express and secrete the fusion polypeptide. For example, the signal sequence from glucoamylase from *Aspergillus niger* is preferred when expressing and secreting a fusion polypeptide from *Aspergillus niger*. As used herein, first amino acid sequences correspond to secretory sequences which are functional in a filamentous fungus. Such amino acid sequences are encoded by first DNA sequences as defined.

As used herein, "second DNA sequences" encode "secreted polypeptides" normally expressed from filamentous fungi. Such secreted polypeptides include glucoamylase, α-amylase and aspartyl proteases from *Aspergillus niger* var. *awamori, Aspergillus niger*, and *Aspergillus oryzae*, cellobiohydrolase I, cellobiohydrolase II, endoglucanase I and endoglucanase III from *Trichoderma* and glucoamylase from *Neurospora* species and *Humicola* species. As with the first DNA sequences, preferred secreted polypeptides are those which are naturally secreted by the filamentous fungal expression host. Thus, for example when using *Aspergillus niger*, preferred secreted polypeptides are glucoamylase and α-amylase from *Aspergillus niger*, most preferably glucoamylase. In one aspect the glucoamylase is greater than 95%, 96%, 97%, 98% or 99% homologous with an *Aspergillus* glucoamylase.

When *Aspergillus* glucoamylase is the secreted polypeptide encoded by the second DNA sequence, the whole protein or a portion thereof may be used, optionally including a prosequence. Thus, the cleavable linker polypeptide may be fused to glucoamylase at any amino acid residue from position 468-509. Other amino acid residues may be the fusion site but utilizing the above residues is particularly advantageous.

A "functional portion of a secreted polypeptide" or grammatical equivalents means a truncated secreted polypeptide that retains its ability to fold into a normal, albeit truncated, configuration. For example, in the case of bovine chymosin production by *A. niger* var. *awamori* it has been shown that fusion of prochymosin following the 11th amino acid of mature glucoamylase provided no benefit compared to production of preprochymosin (U.S. Pat. No. 5,364,770). In U.S. Ser. No. 08/318,494, it was shown that fusion of prochymosin onto the C-terminus of preproglucoamylase up to the 297th amino acid of mature glucoamylase plus a repeat of amino acids 1-11 of mature glucoamylase yielded no secreted chymosin in *A. niger* var. *awamori*. In the latter case it is unlikely that the portion (approximately 63%) of the glucoamylase catalytic domain present in the fusion protein was able to fold correctly so that an aberrant, mis-folded and/or unstable fusion protein may have been produced which could not be secreted by the cell. The inability of the partial catalytic domain to fold correctly may have interfered with the folding of the attached chymosin. Thus, it is likely that sufficient residues of a domain of the naturally secreted polypeptide must be present to allow it to fold in its normal configuration independently of the desired polypeptide to which it is attached.

In most cases, the portion of the secreted polypeptide will be both correctly folded and result in increased secretion as compared to its absence.

Similarly, in most cases, the truncation of the secreted polypeptide means that the functional portion retains a biological function. In a preferred embodiment, the catalytic domain of a secreted polypeptide is used, although other functional domains may be used, for example, the substrate binding domains. In the case of *Aspergillus niger* and *Aspergillus niger* var. *awamori* glucoamylase, preferred functional portions retain the catalytic domain of the enzyme, and include amino acids 1-471. Additionally preferred embodiments utilize the catalytic domain and all or part of the linker region. Alternatively, the starch binding domain of glucoamylase may be used, which comprises amino acids 509-616 of *Aspergillus niger* and *Aspergillus niger* var. *awamori* glucoamylase.

As used herein, "third DNA sequences" comprise DNA sequences encoding a cleavable linker polypeptide. Such sequences include those which encode the prosequence of bovine chymosin, the prosequence of subtilisin, prosequences of retroviral proteases including human immunodeficiency virus protease and DNA sequences encoding amino acid sequences recognized and cleaved by trypsin, factor $X_a$ collagenase, clostripin, subtilisin, chymosin, yeast KEX2 protease, *Aspergillus* KEXB and the like. See e.g. Marston, F. A. O. (1986) *Biol. Chem J.* 240, 1-12. Such third DNA sequences may also encode the amino acid methionine that may be selectively cleaved by cyanogen bromide. It should be understood that the third DNA sequence need only encode that amino acid sequence which is necessary to be recognized by a particular enzyme or chemical agent to bring about cleavage of the fusion polypeptide. Thus, the entire prosequence of, for example, chymosin or subtilisin need not be used. Rather, only that portion of the prosequence which is necessary for recognition and cleavage by the appropriate enzyme is required.

It should be understood that the third nucleic acid need only encode that amino acid sequence which is necessary to be recognized by a particular enzyme or chemical agent to bring about cleavage of the fusion polypeptide.

Particularly preferred cleavable linkers are the KEX2 protease recognition site (Lys-Arg), which can be cleaved by a native *Aspergillus* KEX2-like (KEXB) protease, trypsin protease recognition sites of Lys and Arg, and the cleavage recognition site for endoproteinase-Lys-C.

As used herein, "fourth DNA sequences" encode "desired polypeptides." Such desired polypeptides include mammalian immunoglobulin chains. Immunoglobulins include, but are not limited to, antibodies from any species from which it is desirable to produce large quantities. It is especially preferred that the antibodies are human antibodies. Immunoglobulins may be from any class, i.e., G, A, M, E or D. In another aspect the antibodies are monoclonal. The antibody chains may be either the heavy or light chain. The terms "immunoglobulin" and "antibody" are used interchangeably herein.

The above-defined four DNA sequences encoding the corresponding four amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence will encode a "fusion polypeptide" or "fusion protein" encoding from its amino-terminus a signal peptide functional as a secretory sequence in a filamentous fungus, a secreted polypeptide or portion thereof normally secreted from a filamentous fungus, a cleavable linker polypeptide and a desired polypeptide.

As used herein, a "promotor sequence" is a DNA sequence which is recognized by the particular filamentous fungus for expression purposes. It is operably linked to a DNA sequence encoding the above defined fusion polypeptide. Such linkage comprises positioning of the promoter with respect to the translation initiation codon of the DNA sequence encoding the fusion DNA sequence. The promoter sequence contains transcription and translation control sequences which mediate the expression of the fusion DNA sequence. Examples include the promoter from the *A. niger* var. *awamori* or *A. niger* glucoamylase genes (Nunberg, J. H. et al. (1984) *Mol. Cell. Biol.* 4, 2306-2315; Boel, E. et al. (1984) *EMBO J.* 3, 1581-1585), the *A. oryzae, A. niger* var. *awamori* or *A. niger* or alpha-amylase genes, the *Rhizomucor miehei* carboxyl protease gene, the *Trichoderma reesei* cellobiohydrolase I gene (Shoemaker, S. P. et al. (1984) European Patent Application No. EPO0137280A1), the *A. nidulans* trpC gene (Yelton, M. et al. (1984) *Proc. Natl. Acad. Sci. USA* 81, 1470-1474; Mullaney, E. J. et al. (1985) *Mol. Gen. Genet.* 199, 37-45) the *A. nidulans* alcA gene (Lockington, R. A. et al. (1986) *Gene* 33 137-149), the *A. nidulans* amdS gene (McKnight, G. L. et al. (1986) *Cell* 46, 143-147), the *A. nidulans* amdS gene (Hynes, M. J. et al. (1983) *Mol. Cell Biol.* 3, 1430-1439), and higher eukaryotic promoters such as the SV40 early promoter (Barclay, S. L. and E. Meller (1983) *Molecular and Cellular Biology* 3, 2117-2130).

Likewise a "terminator sequence" is a DNA sequence which is recognized by the expression host to terminate transcription. It is operably linked to the 3' end of the fusion DNA encoding the fusion polypeptide to be expressed. Examples include the terminator from the *A. nidulans* trpC gene (Yelton, M. et al. (1984) *Proc. Natl. Acad. Sci. USA* 81, 1470-1474; Mullaney, E. J. et al. (1985) *Mol. Gen. Genet.* 199, 37-45), the *A. niger* var. *awamori* or *A. niger* glucoamylase genes (Nunberg, J. H. et al. (1984) *Mol. Cell. Biol.* 4, 2306-253; Boel, E. et al. (1984) *EMBO J.* 3, 1581-1585), the *A. oryzae, A. niger* var. *awamori* or *A. niger* or alpha-amylase genes and the *Rhizomucor miehei* carboxyl protease gene (EPO Publication No. 0 215 594), although any fungal terminator is likely to be functional in the present invention.

A "polyadenylation sequence" is a DNA sequence which when transcribed is recognized by the expression host to add polyadenosine residues to transcribed mRNA. It is operably linked to the 3' end of the fusion DNA encoding the fusion polypeptide to be expressed. Examples include polyadenylation sequences from the *A. nidulans* trpC gene (Yelton, M. et al. (1984) *Proc. Natl. Acad. Sci. USA* 81, 1470-1474; Mullaney, E. J. et al. (1985) *Mol. Gen. Genet.* 199, 37-45), the *A. niger* var. *awamori* or *A. niger* glucoamylase genes (Nunberg, J. H. et al. (1984) *Mol. Cell. Biol.* 4, 2306-2315) (Boel, E. et al. (1984) *EMBO J.* 3, 1581-1585), the *A. oryzae, A. niger* var. *awamori* or *A. niger* or alpha-amylase genes and the *Rhizomucor miehei* carboxyl protease gene described above. Any fungal polyadenylation sequence, however, is likely to be functional in the present invention.

As used herein, the term "selectable marker-encoding nucleotide sequence" refers to a nucleotide sequence which is capable of expression in fungal cells and where expression of the selectable marker confers to cells containing the expressed gene the ability to grow in the presence of a corresponding selective condition.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "expression" refers to the process by which a polypeptide is produced based on the nucleic acid sequence of a gene. The process includes both transcription and translation. It follows that the term "Ig chain expression" refers to transcription and translation of the specific Ig chain gene to be expressed, the products of which include precursor RNA, mRNA, polypeptide, post-translation processed polypeptide, and derivatives thereof. Similarly, "Ig expression" refers to the transcription, translation and assembly of the Ig chains into a form exemplified by FIG. 1. By way of example, assays for immunoglobulin expression include examination of fungal colonies when exposed to the appropriate conditions, western blot for Ig protein, as well as northern blot analysis and reverse transcriptase polymerase chain reaction (RT-PCR) assays for immunoglobulin mRNA.

As used herein the term "glycosylated" means that oligosaccharide molecules have been added to particular amino acid residues on a protein. A "de-glycosylated" protein is a protein that has been treated to partially or completely remove the oligosaccharide molecules from the protein. An "aglycosylated" protein is a protein that has not had the oligosaccharide molecules added to the protein. This may be due to a mutation in the protein that prevents the addition of the oligosaccharide.

A "non-glycosylated" protein is a protein that does not have the oligosaccharide attached to the protein. This may be due to various reasons, including but not limited to, the absence of enzymes responsible for the addition of the oligosaccharides to proteins. The term "non-glycosylated" encompasses both proteins that have not had the oligosaccharide added to the protein and those in which the oligosaccharides have been added but were subsequently removed. An "aglycosylated" protein may be a "non-glycosylated" protein. A "non-glycosylated" protein may be either an "aglycosylated" protein or a "deglycosylated" protein.

Fusion Proteins

The above-defined four DNA sequences encoding the corresponding four amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence will encode a "fusion polypeptide" encoding from its amino-terminus a signal peptide functional as a secretory sequence in a filamentous fungus, a secreted polypeptide or portion thereof normally secreted from a filamentous fungus, a cleavable linker polypeptide and a desired polypeptide, e.g., an immunglobulin chain.

Antibodies are comprised of two chain types, one light and one heavy. The basic structure of an antibody is the same regardless of the specificity for a particular antigen. Each antibody comprises four polypeptide chains of two different types. The chains are called the heavy chain (50-70 kDa in size) and the light chain (25 kDa). Two identical heavy chains and two identical light chains are linked together via interchain disulphide bonds to create the antibody monomer (FIG. 1). In addition to the interchain disulphide bonds there are also intrachain disulphide bonds in both the heavy and light chains. Different types of heavy and light chains are recognized. Heavy chains may be of the $\gamma$, $\propto$, $\alpha$, $\delta$ or $\epsilon$ class and this defines the class of immunoglobulin, i.e., IgG, IgM, IgA, IgD or IgE respectively. There are sub-classes within these classes, e.g., in humans there are four subclasses of the $\gamma$ heavy chain, $\gamma1$, $\gamma2$, $\gamma3$ and $\gamma4$ to produce IgG1, IgG2, IgG3 and IgG4 respectively. Light chains may be of the $\lambda$ or $\kappa$ type but this does not affect the class or subclass definition of the immunoglobulin. Thus, a human IgG1 molecule will contain two identical $\gamma1$ heavy chains linked to two identical light chains which may be of the $\lambda$ or $\kappa$ type (i.e., IgG1$\lambda$ or IgG1$\kappa$).

A heavy chain is divided into distinct structural domains. For example, a $\gamma$ heavy chain comprises, from the amino terminus, a variable region (VH), a constant region (CH1) a hinge region, a second constant region (CH2) and a third constant region (CH3). Light chains are structurally divided into two domains, a variable region (VL) and a constant region (CL). Antibody forms in which the heavy chain has been truncated to remove some of the constant region can be generated by protease digestion or by recombinant DNA methodology. For example, Fab fragments (FIG. 1) of an IgG have a form of the heavy chain (Fd) lacking the hinge region and the CH2 and CH3 domains whereas Fab' fragments (FIG. 1) of an IgG have a form of the heavy chain (Fd') which includes the hinge region but lacks the CH2 and CH3 domains.

Each chain will be expressed as a fusion protein by the host fungal cell. The chains are assembled into a complete antibody comprising the two heavy and two light chains.

Although cleavage of the fusion polypeptide to release the desired antibody will often be useful, it is not necessary. Antibodies expressed and secreted as fusion proteins surprisingly assemble and retain their antigen binding function.

Expression of Recombinant Immunoglobulin and Immunoglobulin Fragments

This invention provides filamentous fungal host cells which have been transduced, transformed or transfected with an expression vector comprising a Ig-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell line is transfected with an expression vector having a promoter or biologically active promoter fragment or one or more (e.g., a series) of enhancers which functions in the host cell line, operably linked to a nucleic acid sequence encoding Ig chain(s), such that the Ig chain(s) and fully assembled Ig is expressed in the cell line. In a preferred embodiment, the DNA sequences encode an Ig coding sequence. In another preferred embodiment, the promoter is a regulatable one.

A. Nucleic Acid Constructs/Expression Vectors

Natural or synthetic polynucleotide fragments encoding immunoglobulin ("immunoglobulin-encoding nucleic acid sequences") may be incorporated into heterologous nucleic acid constructs or vectors, capable of introduction into, and replication in, a filamentous fungal cell. The vectors and methods disclosed herein are suitable for use in host cells for the expression of immunoglobulin chain(s) and fully assembled immunoglobulin molecules. Any vector may be used as long as it is replicable and viable in the cells into which it is introduced. Large numbers of suitable vectors and promoters are known to those of skill in the art, and are commercially available. Appropriate cloning and expression vectors for use in filamentous fungal cells are also described in Sambrook et al., 1989, and Ausubel F M et al., 1989, expressly incorporated by reference herein. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Appropriate vectors are typically equipped with a selectable marker-encoding nucleic acid sequence, insertion sites, and suitable control elements, such as termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionein promoter that can upregulated by addition of certain metal salts. In one embodiment of this invention, glaA promoter is used. This promoter is induced in the presence of maltose. Such promoters are well known to those of skill in the art.

The choice of the proper selectable marker will depend on the host cell, and appropriate markers for different hosts are well known in the art. Typical selectable marker genes encode proteins that (a) confer resistance to antibiotics or other toxins, for example, ampicillin, methotrexate, tetracycline, neomycin (Southern and Berg, J., 1982), mycophenolic acid (Mulligan and Berg, 1980), puromycin, zeomycin, or hygromycin (Sugden et al., 1985) or (b) compliment an auxotrophic mutation or a naturally occuring nutritional deficiency in the host strain. In a preferred embodiment, a fungal pyrG gene is used as a selectable marker (Ballance, D. J. et al., 1983, Biochem. Biophys. Res. Commun. 112:284-289). In another preferred embodiment, a fungal amdS gene is used as a selectable marker (Tilburn, J. et al., 1983, Gene 26:205-221).

A selected immunoglobulin coding sequence may be inserted into a suitable vector according to well-known recombinant techniques and used to transform a cell line capable of immunoglobulin expression. Due to the inherent degeneracy of the genetic code, other nucleic acid sequences which encode substantially the same or a functionally equivalent amino acid sequence may be used to clone and express a specific immunoglobulin, as further detailed above. Therefore it is appreciated that such substitutions in the coding region fall within the sequence variants covered by the present invention. Any and all of these sequence variants can be utilized in the same way as described herein for a parent immunoglobulin-encoding nucleic acid sequence. One skilled in the art will recognize that differing immunoglobulins will be encoded by differing nucleic acid sequences.

Once the desired form of an immunoglobulin nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

Heterologous nucleic acid constructs may include the coding sequence for an immunoglobulin, or a variant, fragment or splice variant thereof: (i) in isolation; (ii) in combination with additional coding sequences; such as fusion protein or signal peptide coding sequences, where the immunoglobulin coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the immunoglobulin coding sequence is a heterologous gene.

A heterologous nucleic acid containing the appropriate nucleic acid coding sequence, as described above, together with appropriate promoter and control sequences, may be employed to transform filamentous fungal cells to permit the cells to express immunoglobulin chains and fully assembled immunoglobulins.

In one aspect of the present invention, a heterologous nucleic acid construct is employed to transfer an immunoglobulin-encoding nucleic acid sequence into a cell in vitro, with established cell lines preferred. Preferably, cell lines that are to be used as production hosts have the nucleic acid sequences of this invention stably integrated. It follows that any method effective to generate stable transformants may be used in practicing the invention.

In one aspect of the present invention, the first and second expression cassettes may be present on a single vector or on separate vectors.

The practice of the present invention will employ, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Animal Cell Culture" (R. I. Freshney, ed., 1987); "Current Protocols in Molecular Biology" (F. M. Ausubel et al., eds., 1987); and "Current Protocols in Immunology" (J. E. Coligan et al., eds., 1991). All patents, patent applications, articles and publications mentioned herein both supra and infra, are hereby expressly incorporated herein by reference.

B. Host Cells and Culture Conditions

The present invention provides cell lines comprising cells which have been modified, selected and cultured in a manner effective to result in expression of immunoglobulin chain(s) and fully assembled immunoglobulin molecules.

Examples of parental cell lines which may be treated and/or modified for immunoglobulin expression include, but are not limited to, filamentous fungal cells. Examples of appropriate primary cell types for use in practicing the invention include, but are not limited to, *Aspergillus* and *Trichoderma*.

Immunoglobulin expressing cells are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of immunoglobulin expression are achieved.

Preferred culture conditions for a given cell line may be found in the scientific literature and/or from the source of the cell line such as the American Type Culture Collection (ATCC). Typically, after cell growth has been established, the cells are exposed to conditions effective to cause or inhibit the expression of immunoglobulin chain(s) and fully assembled immunoglobulin molecules.

In the preferred embodiments, where a immunoglobulin coding sequence is under the control of an inducible promoter, the inducing agent, e.g., a carbohydrate, metal salt or antibiotics, is added to the medium at a concentration effective to induce immunoglobulin expression.

C. Introduction of an Immunoglobulin-Encoding Nucleic Acid Sequence into Host Cells The invention further provides cells and cell compositions which have been genetically modified to comprise an exogenously provided immunoglobulin-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above. In a preferred embodiment, a plasmid is used to transfect a filamentous fungal cell. The transformations may be sequential or by co-transformation.

Various methods may be employed for delivering an expression vector into cells in vitro. Methods of introducing nucleic acids into cells for expression of heterologous nucleic acid sequences are also known to the ordinarily skilled artisan, including, but not limited to electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; *Agrobacterium*-mediated transfer of DNA; and the like. In addition, heterologous nucleic acid constructs comprising a immunoglobulin-encoding nucleic acid sequence can be transcribed in vitro, and the resulting RNA introduced into the host cell by well-known methods, e.g., by injection.

Following introduction of a heterologous nucleic acid construct comprising the coding sequence for immunoglobulin chain(s), the genetically modified cells can be cultured in conventional nutrient media modified as appropriate for activating promoters, selecting transformants or amplifying expression of a immunoglobulin-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the immunoglobulin-encoding nucleic acid sequence found in the heterologous nucleic acid construct.

Fungal Expression

Appropriate host cells include filamentous fungal cells. The "filamentous fungi" of the present invention, which serve both as the expression hosts and the source of the first and second nucleic acids, are eukaryotic microorganisms and include all filamentous forms of the subdivision Eumycotina, Alexopoulos, C. J. (1962), Introductory Mycology, New York: Wiley. These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation. In contrast, vegetative growth by yeasts such as *S. cerevisiae* is by budding of a unicellular thallus. Illustrations of differences between *S. cerevisiae* and filamentous fungi include the inability of *S. cerevisiae* to process *Aspergillus* and *Trichoderma* introns and the inability to recognize many transcriptional regulators of filamentous fungi (Innis, M. A. et al. (1985) Science, 228, 21-26).

Various species of filamentous fungi may be used as expression hosts including the following genera: *Aspergillus, Trichoderma, Neurospora, Penicillium, Cephalosporium, Achlya, Phanerochaete, Podospora, Endothia, Mucor, Fusarium, Humicola*, and *Chrysosporium*. Specific expression hosts include *A. nidulans*, (Yelton, M., et al. (1984) Proc. Natl. Acad. Sci. USA, 81, 1470-1474; Mullaney, E. J. et al. (1985) Mol. Gen. Genet. 199, 3745; John, M. A. and J. F. Peberdy (1984) Enzyme Microb. Technol. 6, 386-389; Tilburn, et al. (1982) Gene 26, 205-221; Ballance, D. J. et al., (1983) Biochem. Biophys. Res. Comm. 112, 284-289; Johnston, I. L. et al. (1985) EMBO J. 4, 1307-1311) *A. niger*, (Kelly, J. M. and M. Hynes (1985) EMBO 4, 475-479) *A. niger* var. *awamori*, e.g., NRRL 3112, ATCC 22342, ATCC 44733, ATCC 14331 and strain UVK 143f, *A. oryzae*, e.g., ATCC 11490, *N. crassa* (Case, M. E. et al. (1979) Proc. Natl. Acad. Scie. USA 76, 5259-5263; Lambowitz U.S. Pat. No. 4,486,553; Kinsey, J. A. and J. A. Rambosek (1984) *Molecular and Cellular Biology* 4, 117-122; Bull, J. H. and J. C. Wooton (1984) Nature 310, 701-704), *Trichoderma reesei*, e.g. NRRL 15709, ATCC 13631, 56764, 56765, 56466, 56767, and *Trichoderma viride*, e.g., ATCC 32098 and 32086. A preferred expression host is *A. niger* var. *awamori* in which the gene encoding the major secreted aspartyl protease has been deleted. The production of this preferred expression host is described in U.S. patent application Ser. No. 214,237 filed Jul. 1, 1988, expressly incorporated herein by reference.

During the secretion process in fungi, which are eukaryotes, the secreted protein crosses the membrane from the cytoplasm into the lumen of the endoplasmic reticulum (ER). It is here that the protein folds and disulphide bonds are formed. Chaperone proteins such as BiP and proteins like protein disulphide isomerase assist in this process. It is also at this stage where sugar chains are attached to the protein to produce a glycosylated protein. Sugars are typically added to asparagine residues as N-linked glycosylation or to serine or threonine residues as O-linked glycosylation. Antibodies are known to assemble in the ER. In mammalian cells the heavy chains become associated with BiP immediately on entry into the ER and are not released until they have associated with the light chain. Correctly folded and glycosylated proteins pass from the ER to the Golgi apparatus where the sugar chains are modified and where the KEX2 or KEXB protease of yeast and fungi resides. The N-linked glycosylation added to secreted proteins produced in fungi differs from that added by mammalian cells.

Antibodies produced by the filamentous fungal host cells may be either glycosylated or non-glycosylated (i.e., aglycosylated or deglycosylated). Because the fungal glycosylation pattern differs from that produced by mammalian cells, the antibodies may be treated with an enzyme to deglycosylate the antibody. Enzymes useful for such deglycosylation are endoglycosidase H, endoglycosidase F1, endoglycosidase F2, endoglycosidase A, PNGase F, PNGase A, and PNGase At.

We have surprisingly found that high levels of full-length assembled antibody can be made in fungi when both the heavy and light chains are fused to a native secreted protein. From the information provided above it is clear that the antibody would be expected to assemble in the ER when glucoamylase was still attached to the N-termini of each of the four chains. This would produce a very large and complicated assembled protein of greater than 350 kD. The glucoamylase would not be expected to be cleaved from the antibody until the assembled complex passed through the Golgi apparatus.

Using the present inventive methods and host cells, we have attained surprisingly high levels of expression. The vast majority of reports of antibody production in microbial systems, e.g., *Escherichia coli* or yeasts such as *Saccharomyces cerevisiae* or *Pichia pastoris* have involved the production of antibody fragments (e.g., Fab fragments) or single-chain antibody forms (e.g., ScFv) (Verma, R. et al., 1998, J. Immunological Methods 216:165-181; Pennell, C. A. and Eldin, P., 1998, Res. Immunol. 149:599-603;). A low level of full-length antibody has been produced and secreted in *Saccharomyces cerevisiae*. In one study, 100 ng/ml of light chain and 50-80 ng/ml of heavy chain were detected in the culture supernatant and approximately 50-70% of the heavy chains were associated with light chain (Horwitz, A. H. et al., 1988, Proc. Natl. Acad. Sci USA). Full-length antibody in a correctly assembled form has been produced in the yeast *Pichia pastoris* (WO 00/23579). However, the highest yields reported were 36 mg/l.

In contrast, the system utilized herein has achieved levels of expression and secretion of greater than 0.5 g/l of full-length antibody. It is routinely found that greater than 1 g/l of the antibody may be recovered from the fermentation broth. Reproducible levels of 1.5 g/l have been achieved. Expression and/or secretion levels as high as 2 to 3 g/l of full length antibody may be attained once the optimal conditions are in place. Although the antibody is secreted as a fusion protein the antibody levels given herein have been corrected for glucoamylase. Thus, the absolute protein produced comprising an antibody is greater than those stated; the amount produced has had the contribution of glucoamylase subtracted to give the stated amounts.

Utility

For some applications of immunoglobulins it is of high important that the immunoglobulins are extremely pure, e.g. having a purity of more than 99%. This is particularly true whenever the immunoglobulin is to be used as a therapeutic, but is also necessary for other applications.

Therapeutic and prophylactic vaccine compositions are contemplated, which generally comprise mixtures of one or more of the above-described monoclonal antibodies, including fragments thereof and combinations thereof. Passive immunization by intramuscularly injection of immunoglobulin concentrates is a well-known application for temporary protection against infectious diseases, which is typically applied when people are traveling from one part of the world to the other.

A more sophisticated application of antibodies for therapeutic use is based on so called "drug-targeting" where very potent drugs are covalently linked to antibodies with specific binding affinities towards specific cells in the human organism, e.g. cancer cells.

The above-described recombinant monoclonal antibodies, including Fab molecules, Fv fragments as well as Fab' and $F(ab')_2$, which are capable of reacting immunologically with samples containing antigen particles are also used herein to detect the presence of antigens in specific binding assays of biological samples. In particular, the novel monoclonal antibodies of the present invention can be used in highly sensitive methods of screening for the presence of an antigen.

The format of specific binding assays will be subject to a great deal of variation in accordance with procedures that are well known in the art. For example, specific binding assays can be formatted to utilize one, or a mixture of several, of the recombinant monoclonal antibodies, (including Fab molecules, Fv fragments as well as Fab' and $F(ab')_2$) that have been prepared according to the present invention. The assay format can be generally based, for example, upon competition, direct binding reaction or sandwich-type assay techniques. Furthermore, the present assays can be conducted using immunoprecipitation or other techniques to separate assay reagents during, or after commencement of, the assay. Other assays can be conducted using monoclonal antibodies that have been insolubilized prior to commencement of the assay. In this regard, a number of insolubilization techniques are well known in the art, including, without limitation, insolubilization by adsorption to an immunosorbent or the like, absorption by contact with the wall of a reaction vessel, covalent crosslinking to insoluble matrices or "solid phase" substrates, noncovalent attachment to solid phase substrates using ionic or hydrophobic interactions, or by aggregation using precipitants such as polyethylene glycol or cross-linking agents such as glutaraldehyde.

There are a large number of solid phase substrates which can be selected for use in the present assays by those skilled in the art. For example, latex particles, microparticles, magnetic-, para-magnetic- or nonmagnetic-beads, membranes, plastic tubes, walls of microtitre wells, glass or silicon particles and sheep red blood cells all are suitable for use herein.

In general, most of the present assays involve the use of a labeled binding complex formed from the combination of a monoclonal antibody (including fragments thereof) with a detectable label moiety. A number of such labels are known in the art and can be readily attached (either using covalent or non-covalent association techniques) to the monoclonal antibodies of the present invention to provide a binding complex for use in the above-noted assay formats. Suitable detectable moieties include, but are not limited to, radioactive isotopes, fluorescers, luminescent compounds (e.g., fluorescein and rhodamine), chemiluminescers (e.g., acridinium, phenanthridinium and dioxetane compounds), enzymes (e.g., alkaline phosphatase, horseradish peroxidase and beta-galactosidase), enzyme substrates, enzyme cofactors, enzyme inhibitors, dyes, and metal ions. These labels can be associated with the antibodies using attachment techniques that are known in the art.

Exemplary assay methods generally involve the steps of: (1) preparing the detectably labeled binding complexes as above; (2) obtaining a sample suspected of containing antigen; (3) incubating the sample with the labeled complexes under conditions which allow for the formation of an antibody-antigen complex; and (4) detecting the presence or absence of labeled antibody-antigen complexes. As will be appreciated by those skilled in the art upon the reading of this specification, such assays can be used to screen for the presence of antigens in human donor blood and serum products. When the assays are used in the clinical setting samples can be obtained from human and animal body fluids, such as whole blood, serum, plasma, cerebrospinal fluid, urine and the like. Furthermore, the assays can be readily used to provide quantitative information using reference to standards or calibrants as known in the art.

In one particular assay method of the invention, an enzyme-linked immunosorbent assay (ELISA) can be used to quantify an antigen concentration in a sample. In the method, the specific binding molecules of the present invention are conjugated to an enzyme to provide a labeled binding complex, wherein the assay uses the bound enzyme as a quantitative label. In order to measure antigen, a binding molecule capable of specifically binding the selected antigen (e.g., an antibody molecule) is immobilized to a solid phase substrate (e.g., a microtitre plate or plastic cup), incubated with test sample dilutions, washed and incubated with the binding molecule-enzyme complexes of the invention, and then washed again. In this regard, suitable enzyme labels are generally known, including, for example, horseradish peroxidase. Enzyme activity bound to the solid phase is measured by adding the specific enzyme substrate, and determining product formation or substrate utilization calorimetrically. The enzyme activity bound to the solid phase substrate is a direct function of the amount of antigen present in the sample.

In another particular assay method of the invention, the presence of antigen in a biological sample (e.g., as an indicator of infection) can be detected using strip immunoblot assay (SIA) techniques, such as those known in the art which combine traditional Western and dot blotting techniques, e.g., the RIBA™ (Chiron Corp., Emeryville, Calif.) test. In these assays, one or more of the specific binding molecules (the recombinant monoclonal antibodies, including Fab molecules) are immobilized as individual, discrete bands on a membranous support test strip. Visualization of reactivity with antigens present in the biological sample is accomplished using sandwich binding techniques with labeled antibody-conjugates in conjunction with a colorimetric enzyme substrate. Internal controls can also be present on the strip. The assay can be performed manually or used in an automated format.

Furthermore, the recombinant human monoclonal antibodies, (including Fab molecules, Fv fragments as well as Fab' and $F(ab')_2$ molecules) that have been prepared according to the present invention can be used in affinity chromatography techniques in order to detect the presence of antigen in a biological sample or to purify the antigen from the other components of the biological sample. Such methods are well known in the art.

Kits suitable for use in conducting any of the above-described assays and affinity chromatography techniques, and containing appropriate labeled binding molecule complex reagents can also be provided in accordance with the practice of the invention. Assay kits are assembled by packaging the appropriate materials, including all reagents and materials necessary for conducting the assay in a suitable container, along with an appropriate set of assay instructions.

EXAMPLES

The following preparations and examples are given to enable those skilled in the art to more clearly understand and practice the present invention. They should not be considered as limiting the scope and/or spirit of the invention, but merely as being illustrative and representative thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer achromatography); Ts (tosyl); Bn (benzyl); Ph (phenyl); Ms (mesyl); Et (ethyl), Me (methyl), SDS (sodium dodecyl sulfate), PAGE (polyacrylamide gel electrophoresis), kDa (kiloDaltons), bp (base pairs).

Example 1

Cloning DNA Encoding the Human Ig κ Light Chain Constant Region

The human Ig K light chain constant region was PCR amplified from human leukocyte cDNA (QUICK-Clone cDNA, Clontech Laboratories, Palo Alto, Calif.). The primers used were:

BPF001:
5-CCGTGGCGGCGCCATCTGTCTTCATCTTCCCGCCATCTG-3 (SEQ ID NO: 1)

BPF002:
5-CAGTTCTAGAGGATCAACACTCTCCCCTGTTGAAGCTCTTTG-3 (SEQ ID NO: 2)

BPF001 includes two silent mutations to introduce a NarI restriction site (GGCGCC) for cloning purposes. BPF002 introduces an XbaI restriction site (TCTAGA) following the translation termination signal for cloning purposes. The PCR product was cloned into pCR2.1 TOPO (Invitrogen Corporation, Carlsbad, Calif.) using the TOPO TA cloning kit and protocol supplied by the manufacturer to create K1-pCR2.1TOPO. DNA from clone K1-pCR2.1TOPO was sequenced. The sequence is shown below.

```
GAATTCGCCCTTCCGTGGCGGCGCCATCTGTCTTCATCTTCCCGCCATCTGATGAG   (SEQ ID NO:
                                                            3)
CAGTTGAAATCTGGAACTGCCTCTGTTGTGTGCCTGCTGAATAACTTCTATCCCAGA
GAGGCCAAAGTACAGTGGAAGGTGGATAACGCCCTCCAATCGGGTAACTCCCAGGA
GAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCAT
CAGGGCCTGAGCTCGCCCGTCACAAAGAGCTTCAACAGGGGAGAGTGTTGATCCTC
TAGAACTGAAGGGCGAATTC
```

The sequence obtained matches GenBank accession number J00241; human Ig germline κ L chain, C region (inv3 allele).

Example 2

Cloning DNA Encoding the Human γ1 Heavy Chain Constant Region

The human γ 1 heavy chain constant region was PCR amplified from human leukocyte cDNA (QUICK-Clone cDNA, Clontech Laboratories, Palo Alto, Calif.). The primers used were:

```
BPF006:
5-GGGCCCATCGGTCTTCCCCCTGGCA-3                  (SEQ ID NO:
                                                4)
and

BPF004:
5-CAGTTCTAGAGGATCATTTACCCGGAGACAGGGAGAGGCTC-3  (SEQ ID NO:
                                                5)
```

BPF006 takes advantage of the naturally occurring ApaI restriction site (GGGCCC) at the 5 end of the human γ1 CH1 region. BPF004 introduces an XbaI restriction site (TCTAGA) following the translation termination codon for cloning purposes. The PCR product was cloned into pCR2.1 TOPO (Invitrogen Corporation, Carlsbad, Calif.) using the TOPO TA cloning kit and protocol supplied by the manufacturer to create BG13-pCR2.1-TOPO. DNA from clone BG13-pCR2.1-TOPO was sequenced. The sequence is shown below.

```
GGGCCCATCGGTCTTCCCCCTGGCACCCTCCTCCAAGAGCACCTCTGGGGGCACA   (SEQ ID NO:
                                                           6)
GCGGCCCTGGGCTGCCTGGTCAAGGACTACTTCCCCGAACCGGTGACGGTGTCGT
GGAACTCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTTGGGCA
CCCAGACCTACATCTGCAACGTGAATCACAAGCCCAGCAACACCAAGGTGGACAAG
AGAGTTGAGCCCAAATCTTGTGACAAAACTCACACATGCCCACCGTGCCCAGCACCT
GAACTCCTGGGGGGACCGTCAGTCTTCCTCTTCCCCCCAAAACCCAAGGACACCCT
CATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAA
GACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAA
CAAAGCCCTCCCAGCCCCCATCGAGAAAACCATCTCCAAAGCCAAAGGGCAGCCCC
GAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTG
GGAGAGCAATGGGCAGCCGGAGAACAACTACAAGACCACGCCTCCCGTGCTGGAC
TCCGACGGCTCCTTCTTCCTCTATAGCAAGCTCACCGTGGACAAGAGCAGGTGGCA
GCAGGGGAACGTCTTCTCATGCTCCGTGATGCATGAGGCTCTGCACAACCACTACA
CGCAGAAGAGCCTCTCCCTGTCTCCGGGTAAATGATCCTCTAGA
```

The sequence obtained matches the exon sequences of GenBank accession number Z17370; human germline immunoglobulin γ1 chain constant region gene, except for the following:

1) A change from an A to a G at nucleotide number 500 in Z17370 which represents a Lysine to an Arginine change in the protein corresponding to the G1m(3) allotype.
2) Changes from a T to a G and from a C to an A at nucleotide numbers 1533 and 1537 respectively in Z17370 representing Aspartate to Glutamate and Leucine to Methionine changes respectively. These changes correspond to the non(1) allotype.
3) a silent mutation of C to T corresponding to base 1686 of Z17370.

Example 3

Synthesis of DNA Encoding Trastuzumab Light Chain Variable Region

DNA encoding the amino acid sequence of the trastuzumab light chain variable region (As given in Carter et al., 1992, Proc. Natl. Acad. Sci. USA 89:4285-4289 except that tyrosine replaced glutamic acid at amino acid position 55) was synthesized by Aptagen, Inc., Herndon, Va., using their Gene Forge custom gene synthesis technology. The sequence is shown below.

```
TACGTATAAGCGCGATATCCAGATGACCCAGTCCCCGAGCTCCCTGTCCGCCTCTG   (SEQ ID NO: 7)
TGGGCGATAGGGTCACTATCACCTGCCGTGCCAGTCAGGATGTGAATACTGCTGTA
GCCTGGTATCAACAGAAACCCGGAAAGGCCCCGAAACTGCTGATTTACTCGGCATC
CTTCCTCTACTCTGGAGTCCCTTCTCGCTTCTCTGGTTCCCGCTCTGGGACGGATTT
CACTCTGACCATCAGCTCCCTGCAGCCGGAAGACTTCGCAACTTATTACTGTCAGCA
ACACTATACTACTCCTCCGACGTTCGGACAGGGTACCAAGGTGGAGATCAAACGTA
CCGTGGCGGCGCC
```

This DNA sequence includes a 5' SnaB1 restriction site (TACGTA) to allow digestion and ligation to the *A. niger* glucoamylase coding region followed by codons for the amino acids Lysine and Arginine (AAG CGC) representing a KEX2 protease cleavage site. At the 3' end there is a NarI restriction site to allow digestion and ligation to the light chain constant region. The codon usage in this DNA reflects the frequency of codon usage observed in *Aspergillus* genes.

Example 4

Synthesis of DNA Encoding Trastuzumab Heavy Chain Variable Region

DNA encoding the amino acid sequence of the trastuzumab heavy chain variable region (As given in Carter et al., 1992, Proc. Natl. Acad. Sci. USA 89:4285-4289 except that tyrosine replaced valine at amino acid position 105) was synthesized by Aptagen, Inc., Herndon, Va., using their Gene Forge custom gene synthesis technology. The sequence is shown below.

```
TACGTATAAGCGCGAGGTTCAGCTGGTGGAGTCTGGCGGTGGCCTGGTGCAGCCC   (SEQ ID NO: 8)
GGGGGCTCTCTCCGTTTGTCCTGTGCAGCTTCTGGCTTCAACATTAAAGACACCTAT
ATCCACTGGGTGCGTCAGGCTCCGGGTAAGGGCCTGGAGTGGGTTGCAAGGATTTA
TCCTACGAATGGTTATACTCGTTATGCCGATAGCGTCAAGGGCCGTTTCACTATAAG
CGCAGACACTTCGAAAAACACAGCCTACCTCCAGATGAACAGCCTGCGTGCTGAGG
ACACTGCCGTCTATTATTGTAGCAGATGGGGTGGGGACGGCTTCTATGCTATGGAC
TACTGGGGTCAAGGTACACTAGTCACCGTCAGCAGCGCTAGCACCAAGGGCCC
```

This DNA sequence includes a 5' SnaB1 restriction site (TACGTA) to allow digestion and ligation to the *A. niger* glucoamylase coding region followed by codons for the amino acids Lysine and Arginine (AAG CGC) representing a KEX2 protease cleavage site. At the 3' end there is an ApaI restriction site to allow digestion and ligation to the heavy chain constant region. The codon usage in this DNA reflects the frequency of codon usage observed in *Aspergillus* genes.

Example 5

Construction of a Trastuzumab Light Chain Expression Plasmid Containing the pyrG Marker The expression plasmid used for light chain expression in *Aspergillus* was based on pGAMpR, a glucoamylase-prochymosin expression vector which is described in detail in U.S. Pat. No. 5,679,543. This plasmid was digested with the restriction endonucleases SnaBI and XbaI, each of which cuts only once in pGAMpR. SnaBI cuts the plasmid within the coding region for the glucoamylase linker region and XbaI cuts pGAMpR just after the 3 end of the chymosin coding region. Using techniques known in the art the DNA sequences encoding the light chain variable and constant regions were assembled and inserted into pGAMpR replacing the chymosin encoding region. The final plasmid was named pQ83 (FIG. 3). This plasmid contains the *Neurospora crassa* pyr4 gene as a selectable marker for transformation into *Aspergillus* or other fungi. The *Aspergillus awamori* glaA (glucoamylase) promoter and *A. niger* glaA terminator are included to control expression of the open reading frame which includes the light chain encoding DNA. This plasmid was designed for the expression of a fusion protein consisting of the glucoamylase signal sequence, prosequence, catalytic domain and linker region up to amino acid number 502 of mature glucoamylase (Nunberg, J. H. et al., 1984, Mol. Cell. Biol. 4:2306-2315), followed by amino acids YKR and then by the mature light chain. Free light chain can be obtained after cleavage of this fusion protein immediately after the KR residues placed at the end of the glucoamylase linker region by *Aspergillus* KEX2 proteinase. The complete amino acid sequence of the fusion protein is given here. The YKR sequence between the end of the glucoamylase linker region and the start of the light chain sequence is underlined.

MSFRSLLALSGLVCTGLANVISKRATLDSWLSNEATVARTAILNNIGADGAWVSGADSGI (SEQ ID NO: 9)
VVASPSTDNPDYFYTWTRDSGLVLKTLVDLFRNGDTSLLSTIENYISAQAIVQGISNPSGD
LSSGAGLGEPKFNVDETAYTGSWGRPQRDGPALRATAMIGFGQWLLDNGYTSTATDIV
WPLVRNDLSYVAQYWNQTGYDLWEEVNGSSFFTIAVQHRALVEGSAFATAVGSSCSW
CDSQAPEILCYLQSFWTGSFILANFDSSRSGKDANTLLGSIHTFDPEAACDDSTFQPCSP
RALANHKEVVDSFRSIYTLNDGLSDSEAVAVGRYPEDTYYNGNPWFLCTLAAAEQLYDA
LYQWDKQGSLEVTDVSLDFFKALYSDAATGTYSSSSSTYSSIVDAVKTFADGFVSIVETH
AASNGSMSEQYDKSDGEQLSARDLTWSYAALLTANNRRNSVVPASWGETSASSVPGT
CAATSAIGTYSSVTVTSWPSIVATGGTTTTATPTGSGSVTSTSKTTATASKTSTYKRDIQ
MTQSPSSLSASVGDRVTITCRASQDVNTAVAWYQQKPGKAPKLLIYSASFLYSGVPSRF
SGSRSGTDFTLTISSLQPEDFATYYCQQHYTTPPTFGQGTKVEIKRTVAAPSVFIFPPSDE
QLKSGTASVVCLLNNFYPREAKVQWKVDNALQSGNSQESVTEQDSKDSTYSLSSTLTL
SKADYEKHKVYACEVTHQGLSSPVTKSFNRGEC

Example 6

Construction of Trastuzumab Heavy Chain Expression Plasmids

The *Aspergillus* expression vector pGAMpR was modified by methods known in the art to replace the *N. crassa* pyr4 gene with the *Aspergillus nidulans* amdS gene as a selectable marker for transformation into *Aspergillus* or other fungi (Kelly J. M. and Hynes, M. J., 1985, EMBO J. 4:475-479; Corrick, C. M. et al., 1987, Gene 53:63-71). Using techniques known in the art the DNA sequences encoding the heavy chain variable and constant regions were assembled and inserted into the version of the *Aspergillus* expression vector pGAMpR with the amdS selectable marker. The final plasmid was named pCL1 (FIG. 4). The *Aspergillus awamori* glaA (glucoamylase) promoter and *A. niger* glaA terminator are included to control expression of the open reading frame which includes the heavy chain encoding DNA. This plasmid was designed for the expression of a fusion protein consisting of the glucoamylase signal sequence, prosequence, catalytic domain and linker region up to amino acid number 502 of mature glucoamylase, followed by amino acids YKR and then by the mature heavy chain. Free heavy chain can be obtained after cleavage of this fusion protein immediately after the KR residues placed at the end of the glucoamylase linker region by *Aspergillus* KEX2 proteinase. The complete amino acid sequence of the fusion protein is given here. The YKR sequence between the end of the glucoamylase linker region and the start of the heavy chain sequence is underlined.

MSFRSLLALSGLVCTGLANVISKRATLDSWLSNEATVARTAILNNIGADGAWVSGADSGI (SEQ ID NO: 10)
VVASPSTDNPDYFYTWTRDSGLVLK-
TLVDLFRNGDTSLLSTIENYISAQAIVQGISNPSGD
LSSGAGLGEPKFNVDETAYTGSWGRPQRDGPALRATAMIGFGQWLLDNGYTSTATDIV
WPLVRNDLSYVAQYWNQTGYDLWEEVNGSSFFTIAVQHRALVEGSAFATAVGSSCSW
CDSQAPEILCYLQSFWTGSFILANFDSSRSGKDANTLLGSIHTFDPEAACDDSTFQPCSP
RALANHKEVVDSFRSIYTLNDGLSDSEAVAVGRYPEDTYYNGNPWFLCTLAAAEQLYDA
LYQWDKQGSLEVTDVSLDFFKALYSDAATGTYSSSSSTYSSIVDAVKTFADGFVSIVETH
AASNGSMSEQYDKSDGEQLSARDLTWSYAALLTANNRRNSVVPASWGETSASSVPGT
CAATSAIGTYSSVTVTSWPSIVATGGTTTTATPTGSGSVTSTSKTTATASKTSTYKREVQ
LVESGGGLVQPGGSLRLSCAASGFNIKDTYIHWVRQAPGKGLEWVARIYPTNGYTRYAD
SVKGRFTISADTSKNTAYLQMNSLRAEDTAVYYCSRWGGDGFYAMDYWGQGTLVTVS
SASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK

A second trastuzumab heavy chain expression plasmid (pCL5; FIG. 5) was constructed which contained exactly the same expression cassette as pCL1 (i.e., the *Aspergillus niger* var. *awamori* glaA promoter and *A. niger* glaA terminator controlling expression of the open reading frame encoding a fusion protein consisting of the glucoamylase signal sequence, prosequence, catalytic domain and linker region up to amino acid number 502 of mature glucoamylase, followed by amino acids YKR and then by the mature heavy chain). The only differences between pCL1 and pCL5 were that the latter plasmid lacked the *A. nidulans* amdS gene and, therefore, lacked a fungal transformation marker and that pBR322 instead of pUC100 was used as the bacterial plasmid backbone.

Example 7

Construction of an Expression Plasmid for the Fd' Fragment of the Trastuzumab Heavy Chain PCR was used to generate a DNA fragment encoding the Fd' portion of the heavy chain (heavy chain truncated after the antibody hinge region) using the assembled heavy chain variable and constant region DNA as template. The following two primers were used: oligo1 (5'-AAC AGC TAT GAC CAT G-3') (SEQ ID NO: 11) and oligo2 (5-TCT AGA GGA TCA TGC GGC GCA CGG TGG GCA TGT GTG AG-3) (SEQ ID NO: 12). The amplified 900 bp fragment was purified, digested with SnaBI and XbaI and the 719 bp SnaB1 to XbaI fragment generated was cloned into version of the the *Aspergillus* expression pGAMpR with the amdS gene as selectable marker. The final plasmid was named pCL2 (FIG. 6). The *Aspergillus awamori* glaA (glucoamylase) promoter and *A. niger* glaA terminator are included to control expression of the open reading frame which includes the heavy chain encoding DNA. This plasmid was designed for the expression of a fusion protein consisting of the glucoamylase signal sequence, prosequence, catalytic domain and linker region up to amino acid number 502 of mature glucoamylase, followed by amino acids YKR and then by the mature Fd' portion of the heavy chain. Free Fd' chain can be obtained after cleavage of this fusion protein immediately after the KR residues placed at the end of the glucoamylase linker region by *Aspergillus* KEX2 proteinase. The complete amino acid sequence of the fusion protein is given here. The YKR sequence between the end of the glucoamylase linker region and the start of the heavy chain sequence is underlined.

*Aspergillus awamori* glaA (glucoamylase) promoter and *A. niger* glaA terminator are included to control expression of the open reading frame which includes the heavy chain encoding DNA. This plasmid was designed for the expression of a fusion protein consisting of the glucoamylase signal

```
MSFRSLLALSGLVCTGLANVISKRATLDSWLSNEATVARTAILNNIGADGAWVSGADSGI(SEQ ID NO: 13)
VVASPSTDNPDYFYTWTRDSGLVLK-
TLVDLFRNGDTSLLSTIENYISAQAIVQGISNPSGD
LSSGAGLGEPKFNVDETAYTGSWGRPQRDGPALRATAMIGFGQWLLDNGYTSTATDIV
WPLVRNDLSYVAQYWNQTGYDLWEEVNGSSFFTIAVQHRALVEGSAFATAVGSSCSW
CDSQAPEILCYLQSFWTGSFILANFDSSRSGKDANTLLGSIHTFDPEAACDDSTFQPCSP
RALANHKEVVDSFRSIYTLNDGLSDSEAVAVGRYPEDTYYNGNPWFLCTLAAAEQLYDA
LYQWDKQGSLEVTDVSLDFFKALYSDAATGTYSSSSSTYSSIVDAVKTFADGFVSIVETH
AASNGSMSEQYDKSDGEQLSARDLTWSYAALLTANNRRNSVVPASWGETSASSVPGT
CAATSAIGTYSSVTVTSWPSIVATGGTTTTATPTGSGSVTSTSKTTATASKTSTYKREVQ
LVESGGGLVQPGGSLRLSCAASGFNIKDTYIHWVRQAPGKGLEWVARIYPTNGYTRYAD
SVKGRFTISADTSKNTAYLQMNSLRAEDTAVYYCSRWGGDGFYAMDYWGQGTLVTVS
SASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCAA
```

Example 8

Construction of an Expression Plasmid for an Aglycosylated Form of the Trastuzumab Heavy Chain There is known to be a single asparagine (at position 297) in the IgG heavy chain constant region which is the site of attachment for N-linked glycosylation. In order to prevent glycosylation of the antibody produced in *Aspergillus* the codon encoding this asparagine has been changed to a codon which encodes glutamine. The QuikChange Site-Directed Mutagenesis kit (Stratagene, La Jolla, Calif.) was used according to the manufacturers directions to make the appropriate change to the DNA sequence. A plasmid containing the assembled DNA encoding the heavy chain variable and constant regions was used as a template. The following two primers, one complementary to one DNA strand of the plasmid and the other complementary to the second strand of the plasmid, which overlap the asparagine codon to be mutated were used in the mutagenesis procedure: 5-GAG CAG TAC CAG AGC ACG TAC CGT GTG GTC-3 (SEQ ID NO: 14) and 5-GTA CGT GCT CTG GTA CTG CTC CTC CCG CGG CT-3 (SEQ ID NO: 15). The altered codon is underlined. DNA sequence analysis confirmed that the desired sequence change had been created and that no other undesired mutations had been introduced. The mutated version of full-length heavy chain was then cloned into the version of the *Aspergillus* expression vector pGAMpR with the amdS selectable marker. The final plasmid was named pCL3 (FIG. 7). The sequence, prosequence, catalytic domain and linker region up to amino acid number 502 of mature glucoamylase (Nunberg et al., 1984, Mol. Cell. Biol. 4:2306-2315), followed by amino acids YKR and then by the mature heavy chain containing the mutation to prevent glycosylation. Free heavy chain can be obtained after cleavage of this fusion protein immediately after the KR residues placed at the end of the glucoamylase linker region by *Aspergillus* KEX2 proteinase. The complete amino acid sequence of the fusion protein is given here. The YKR sequence between the end of the glucoamylase linker region and the start of the heavy chain sequence is underlined as is the glutamine residue which replaced the asparagine in the original heavy chain sequence.

```
MSFRSLLALSGLVCTGLANVISKRATLDSWLSNEATVARTAILNNIGADGAWVSGADSGI(SEQ ID NO: 16)
VVASPSTDNPDYFYTWTRDSGLVLK-
TLVDLFRNGDTSLLSTIENYISAQAIVQGISNPSGD
LSSGAGLGEPKFNVDETAYTGSWGRPQRDGPALRATAMIGFGQWLLDNGYTSTATDIV
WPLVRNDLSYVAQYWNQTGYDLWEEVNGSSFFTIAVQHRALVEGSAFATAVGSSCSW
CDSQAPEILCYLQSFWTGSFILANFDSSRSGKDANTLLGSIHTFDPEAACDDSTFQPSP
RALANHKEVVDSFRSIYTLNDGLSDSEAVAVGRYPEDTYYNGNPWFLCTAAAEQLYDA
LYQWDKQGSLEVTDVSLDFFKALYSDAATGTYSSSSSTYSSIVDAVKTFADGFVSIVETH
AASNGSMSEQYDKSDGEQLSARDLTWSYAALLTANNRRNSVVPASWGETSASSVPGT
CAATSAIGTYSSVTVTSWPSIVATGGTTTTATPTGSGSVTSTSKTTATASKTSTYKREVQ
LVESGGGLVQPGGSLRLSCAASGFNIKDTYIHWVRQAPGKGLEWVARIYPTNGYTRYAD
SVKGRFTISADTSKNTAYLQMNSLRAEDTAVYYCSRWGGDGFYAMDYWGQGTLVTVS
SASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPELL
GGPSVFLFPPKPKDTLMISRTPEVTCVVVDVSHEDPEVKFNWYVDGVEVHNAKTKPREE
QYQSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK
```

Example 9

Trastuzumab Light Chain Expression in *Aspergillus*

DNA of the integrative (i.e., it is designed to integrate into the host genomic DNA) expression plasmid pQ83 was prepared and transformed into *Aspergillus niger* var. *awamori* strain dgr246ΔGAP:pyr2-. This strain is derived from strain dgr246 P2 which has the pepA gene deleted, is pyrG minus and has undergone several rounds of mutagenesis and screening or selection for improved production of a heterologous gene product (Ward, M. et al., 1993, Appl. Microbiol. Biotech. 39:738-743 and references therein). To create strain dgr246ΔGAP:pyr2- the glaA (glucoamylase) gene was deleted in strain dgr246 P2 using exactly the same deletion plasmid (pΔGAM NB-Pyr) and procedure as reported by Fowler, T. et al (1990) Curr. Genet. 18:537-545. Briefly, the deletion was achieved by transformation with a linear DNA fragment having glaA flanking sequences at either end and with part of the promoter and coding region of the glaA gene replaced by the *Aspergillus nidulans* pyrG gene as selectable marker. Transformants in which the linear fragment containing the glaA flanking sequences and the pyrG gene had integrated at the chromosomal glaA locus were identified by Southern blot analysis. This change had occurred in transformed strain dgr246ΔGAP. Spores from this transformant were plated onto medium containing fluoroorotic acid and spontaneous resistant mutants were obtained as described by van Hartingsveldt, W. et al. (1987) Mol. Gen. Genet. 206:71-75. One of these, dgr246ΔGAP:pyr2-, was shown to be a uridine auxotroph strain which could be complemented by transformation with plasmids bearing a wild-type pyrG gene.

The *Aspergillus* transformation protocol was a modification of the Campbell method (Cambell et at. (1989). Curr. Genet. 16:53-56). All solutions and media were either autoclaved or filter sterilized through a 0.2 micron filter. Spores of *A. niger* var. *awamori* were harvested from complex media agar (CMA) plates. CMA contained 20 g/l dextrose, 20 g/l DifcoBrand malt extract, 1 g/l Bacto Peptone, 20 g/l Bacto agar, 20 ml/l of 100 mg/ml arginine and 20 ml/l of 100 mg/ml uridine. An agar plug of approximately 1.5 cm square of spores was used to inoculate 100 mls of liquid CMA (recipe as for CMA except that the Bacto agar was omitted). The flask was incubated at 37° C. on a shaker at 250-275 rpm, overnight. The mycelia were harvested through sterile Miracloth (Calbiochem, San Diego, Calif., USA) and washed with 200 mls of Solution A (0.8M $MgSO_4$ in 10 mM sodium phosphate, pH 5.8). The washed mycelia were placed in a sterile solution of 300 mg of beta-D-glucanase (Interspex Products, San Mateo, Calif.) in 20 mls of solution A. This was incubated at 28° C. at 200 rpm for 2 hour in a sterile 250 ml plastic bottle (Corning Inc, Corning, N.Y.). After incubation, this protoplasting solution was filtered through sterile Miracloth into a sterile 50 ml conical tube (Sarstedt, USA). The resulting liquid containing protoplasts was divided equally amongst four 50 ml conical tubes. Forty ml of solution B (1.2 M sorbitol, 50 mM $CaCl_2$, 10 mM Tris, pH7.5) were added to each tube and centrifuged in a table top clinical centrifuge (Damon IEC HN SII centrifuge) at ¾ speed for 10 minutes. The supernatant from each tube was discarded and 20 mls of fresh solution B was added to one tube, mixed, then poured into the next tube until all the pellets were resuspended. The tube was then centrifuged at ¾ speed for 10 minutes. The supernatant was discarded, 20 mls of fresh solution B was added, the tube was centrifuged for 10 minutes at ¾ speed. The wash occurred one last time before resuspending the washed protoplasts in solution B at a density of $0.5-1.0\times10^7$ protoplasts/100 ul. To each 100 ul of protoplasts in a sterile 15 ml conical tube (Sarstedt, USA), 10 ul of the transforming plasmid DNA was added. To this, 12.5 ul of solution C (50% PEG 4000, 50 mM $CaCl_2$, 10 mM Tris, pH 7.5) was added and the tube was placed on ice for 20 minutes. One ml of solution C was added and the tube was removed from the ice to room temperature and shaken gently. Two ml of solution B was added immediately to dilute solution C. The transforming mix was added equally to 3 tubes of melted MMS overlay (6 g/l $NaNO_3$, 0.52 g/l KCl, 1.52 g/l $KH_2PO_4$, 218.5 g/l D-sorbitol, 1.0 ml/l trace elements-LW, 10 g/l SeaPlaque agarose (FMC Bioproducts, Rookl and, Maine, USA) 20 ml/l 50% glucose, 2.5 ml/l 20% $MgSO_4.7H_2O$, pH to 6.5 with NaOH) that were stored in a 45° C. water bath. Trace elements-LW consisted of 1 g/l $FeSO_4.7H_2O$, 8.8 g/l $ZnSO_4.7H_2O$, 0.4 µl $CuSO_4.5H_2O$, 0.15 g/l $MnSO_4.4H_2O$, 0.1 g $Na_2B_4O_7.10H_2O$, 50 mg/l $(NH_4)_6Mo_7O_{24}.4H_2O$, 250 mls $H_2O$, 200 ul/l concentrated HCl. The melted overlays with the transformation mix were immediately poured onto 3 MMS plates (same as MMS overlay recipe with the exception of 20 g/l of Bacto agar instead of 10 g/l of SeaPlaque agarose) that had been supplemented with 200 ul/plate of 100 mg/ml of arginine added directly on top of the agar plate. After the agar solidified, the plates were incubated at 37° C. until transformants grew.

The sporulating transformants were picked off with a sterile toothpick onto a plate of minimal media+glucose (MM). MM consisted of 6 g/l $NaNO_3$, 0.52 g/l KCl, 1.52 g/l $KH_2PO_4$, 1 ml/l Trace elements-LW, 20 g/l Bacto agar, pH to 6.5 with NaOH, 25 ml/l of 40% glucose, 2.5 ml/l of 20% $MgSO_4.7H_2O$ and 20 ml/l of 100 mg/ml arginine. Once the transformants grew on MM they were transferred to CMA plates.

A 1.5 cm square agar plug from a plate culture of each transformant was added to 50 mls, in a 250 ml shake flask, of an inoculum medium called CSL+fructose 100 g/l corn steep liquor (50% solids, National), 1 g/l $NaH_2PO_4.H_2O$, 0.5 µl $MgSO_4$, 100 µl maltose, 10 g/l glucose, 50 g/l fructose, 3 m1/l Mazu DF60-P (Mazur Chemicals, Gurnee, Ill., USA), pH to 5.8 with NaOH. Flasks were incubated at 37° C., 200 rpm, for 2 days. Five ml of the 2 day old medium were inoculated into 50 ml of production medium called Promosoy special. This medium had the following components: 70 g/l sodium citrate, 15 g/l $(NH_4)_2$ $SO_4$, 1 g/l $NaH_2PO_4.H_2O$, 1 g/l $MgSO_4$, 1 ml Tween 80, pH to 6.2 with NaOH, 2 ml/l Mazu DF60-P, 45 g/l Promosy 100 (Central Soya, Fort Wayne, Ind.), 120 g/l maltose. The production media flasks were incubated at 30° C., 200 rpm for 5 days and supernatant samples were harvested.

Samples of culture supernatant were mixed with an appropriate volume of 2× sample loading buffer and subjected to sodium dodecyl sulfate-polyacrylamide gel electrophoresis (SDS-PAGE) using precast gels according to the manufacturers instructions (The NuPAGE Bis-Tris Electrophoresis System from Invitrogen Corporation, Carlsbad, Calif.). The gels were either stained for protein with Coomassie Brilliant Blue stain or the protein was transferred to membrane filters by Western blotting (Towbin et al., 1979, Proc. Natl. Acad. Sci. USA 76:4350-4354). Human kappa light chain was visualized on Western blots by sequential treatment with goat anti-human kappa light chain (bound and free) antibody and rabbit anti-goat IgG conjugated with horse radish peroxidase (HRP) followed by HRP color development by incubation with $H_2O_2$ and 4-chloro-l-napthol.

Transformants which produced trastuzumab light chain were identified by the appearance of extra protein bands compared to supernatant from the untransformed parental strain. The sizes and identities of these bands were as follows. A 25 kD band corresponding to the trastuzumab light chain which had been released from the glucoamylase-light chain fusion protein. A band with an apparent molecular weight of approximately 58 kD corresponding to the catalytic core and linker region of glucoamylase which had been released from the glucoamylase-light chain fusion protein. A band with an apparent molecular weight of approximately 85 kD corresponding to the glucoamylase-light chain fusion protein which had not been cleaved into separate glucoamylase and light chain proteins. The identities of the light chain bands were confirmed by Western analysis. The Western analysis employed an anti-human κ antibody to detect both the free light chain and the glucoamylase-light chain fusion protein. Quantification of the light chain in culture supernatants was performed by enzyme-linked immunosorption assays (ELISA). The best light chain expression strain was spore purified and was designated Q83-35-2. This strain produced approximately 1.5 g/l of trastuzumab light chain (κ chain) in shake flask culture according to ELISA. The ELISA was performed using goat anti-human κ (bound and free) antibody as a capture antibody coating the wells of microtiter plates. After adding appropriately diluted culture supernatant, incubation, and then washing the wells, the bound light chain from the supernatant was detected by addition of an goat anti human kappa (bound and free) antibody conjugated with horse radish peroxidase (HRP) followed by a color development reaction. A serial dilution of known concentration for human K light chain was used to produce a standard for quantification purposes.

Example 10

Improved Cleavage of the Glucoamylase-Light Chain Fusion Protein

As indicated above, some of the trastuzumab light chain remained attached to glucoamylase when secreted by *Aspergillus niger* transformants containing pQ83. It was estimated that approximately 60-75% of the secreted light chain was attached to glucoamylase. This indicated that the KEX2 site between glucoamylase and the light chain was not efficiently cleaved by the KEX2 protease. In order to determine if the site of cleavage was as predicted (i.e., immediately after the KR residues of the KEX2 cleavage site) the N-terminus of the free light chain from transformant Q83-35-2 was determined. Proteins in culture supernatant samples were separated by SDS-PAGE and were blotted onto a polyvinylidene difluoride (PVDF) membrane using a Novex transfer cell (Invitrogen Corporation, Carlsbad, Calif.) and transfer buffer consisting of 12 mM Tris base, 96 mM glycine, 20% methanol, 0.01% SDS, pH8.3. The transfer was run at 20 V for 90 minutes. The membrane was rinsed three times for 30 minutes each in distilled water and stained with Coomassie Brilliant Blue R-250. The portion of the membrane with the 25 kD light chain band was excised and the N-terminal sequence was determined by Edman degradation. The data indicated that the population of light chain molecules had a mixture of N-termini, the dominant sequences were DIQM and KRDI and these were present in approximately equal amounts. This result-demonstrates that some of the glucoamylase-light chain fusion proteins were cleaved at the expected position immediately after the KEX2 cleavage site but that approximately half of the cleaved fusion proteins had been cleaved at a position two residues towards the N-terminus.

In order to improve cleavage of the fusion protein we altered the position on the glucoamylase linker region to which the light chain was attached. Additionally, the amino acid sequence at the junction between glucoamylase and light chain was varied.

The expression plasmid used for these experiments was based on the same vector as pGAKHi+, a glucoamylase-hirulog expression vector which is described in detail in WO 9831821. The hirulog-encoding region of this plasmid, which is situated between unique NheI and BstEII restriction endonuclease recognition sites, was replaced by light chain-encoding DNA. NheI cuts the plasmid within the coding region for the glucoamylase linker region and BstEII cuts 5 of the glucoamylase terminator region. Using techniques known in the art the DNA sequence encoding the complete light chain was amplified by PCR using the following pair of primers. 5-CCGCTAGCAAGCGTGATATCCAG-3 (SEQ ID NO:17) was the forward primer and 5-CCGGTGACCGGATCAA-CACTCTCCC-3 (SEQ ID NO:18) was the reverse primer. These primers added NheI and BstEII recognition sites at the 5 and 3 ends of the light chain DNA respectively. The light chain DNA was then inserted into the vector to create a plasmid identical to pGAKHi+ but with the light chain DNA replacing the hirulog-encoding region to create pQ87. This plasmid contained the *Aspergillus niger* pyrG gene as a selectable marker for transformation into *Aspergillus* or other fungi. The *Aspergillus niger* var *awamori* g/aA (glucoamylase) promoter and *A. niger* glaA terminator were included to control expression of the open reading frame which includes the light chain encoding DNA. This plasmid was designed for the expression of the fusion protein shown below consisting of the glucoamylase signal sequence, prosequence, catalytic domain and linker region up to amino acid number 498 (a serine) of mature glucoamylase (Nunberg, J. H. et al., 1984, Mol. Cell. Biol. 4:2306-2315), followed by amino acids KR (underlined below) and then by the mature light chain.

```
      MSFRSLLALSGLVCTGLANVISKRATLDSWLSNEATVARTAILNNIGADGAWVSG    (SEQ ID NO: 19)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEWDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASKRDIQ
MTQSPSSLSASVGDRVTITCRASQDVNTAVAWYQQKPGKAPKLLIYSASFLYSGVPSRF
SGSRSGTDFTLTISSLQPEDFATYYCQQHYTTPPTFGQGTKVEIKRTVAAPSVFIFPPSDE
QLKSGTASVVCLLNNFYPREAKVQWKVDNALQSGNSQESVTEQDSKDSTYSLSSTLTL
SKADYEKHKVYACEVTHQGLSSPVTKSFNRGEC.
```

The amino acid sequence on either side of the KR residues (kexB cleavage site) was altered in a series of plasmids. To construct each new light chain expression plasmid, the following forward primers were used, each in combination with the same reverse primer as described for pQ87, to amplify the light chain DNA fragment in a PCR reaction. 5-CCGCTAGC-CAGAAGCGTGATATCCAGA-3 (SEQ ID NO:20) was the forward primer for pQ88; 5-CCGCTAGCCTCAAGCGT-GATATCCAG-3 (SEQ ID NO:21) was the forward primer for pQ90; 5-CCGCTAGCATCTCCAAGCGTGATATCCAG-3 (SEQ ID NO:22) was the forward primer for pQ91; 5-CCGCTAGCAACGTGATCTCCAAGCGT-GATATCCAG-3 (SEQ ID NO:23) was the forward primer for pQ94; 5-CCGCTAGCGTGATCTCCAAGCGT-GATATCCAG-3 (SEQ ID NO:24) was the forward primer for pQ95; and 5-CCGCTAGCATCTCCAAGCGTGGCGGTG-GCGATATCCAGATGACCCAG-3 (SEQ ID NO:25) was the forward primer for pQ96; The PCR fragment was then digested with restriction enzymes NheI and BstEII and inserted into the expression vector as for pQ87. In pQ88 and pQ90, an amino acid was inserted at the amino-terminal side of the KR residues which had been shown to be accepted at this position for cleavage of synthetic peptides by yeast KEX2 and *A. niger* KexB (Brenner, C. and Fuller, R. S., 1992, Proc. Natl. Acad. Sci. USA 89:922-926; Jalving, R. et al., 2000, Applied and Environmental Microbiology 66:363-368). In pQ91, pQ94 and pQ95, two, four or three residues respectively from the 6 amino acid propeptide of glucoamylase (which ends with KR and is cleaved by KEX2 protease) were placed on the amino-terminal side of the KR residues. Residues from the glucoamylase propeptide sequence have been placed in this position in glucoamylase fusion proteins by others (Spencer, J. A. et al., 1998, European Journal of Biochemistry 258:107-112; Broekhuijsen, M. P. et al., 1993, Journal of Biotechnology 31:135-145). In pQ96, three glycine residues were placed on the carboxyl side of the KR residues as had been employed by (Spencer, J. A. et al., 1998, European Journal of Biochemistry 258:107-112). For each plasmid the amino acid sequence of the encoded glucoamylase-light chain fusion protein is shown below and the variable region around the KEX2 cleavage site (KR) is underlined.

Glucoamylase-light chain fusion protein encoded by pQ88:

```
MSFRSLLALSGLVCTGLANVISKRATLDSWLSNEATVARTAILNNIGADGAWVSG    (SEQ ID NO: 26)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASQKRDI
QMTQSPSSLSASVGDRVTITCRASQDVNTAVAWYQQKPGKAPKLLIYSASFLYSGVPSR
FSGSRSGTDFTLTISSLQPEDFATYYCQQHYTTPPTFGQGTKVEIKRTVAAPSVFIFPPSD
EQLKSGTASVVCLLNNFYPREAKVQWKVDNALQSGNSQESVTEQDSKDSTYSLSSTLT
LSKADYEKHKVYACEVTHQGLSSPVTKSFNRGEC.
```

Glucoamylase-light chain fusion protein encoded by pQ90:

```
MSFRSLLALSGLVCTGLANVISKRATLDSWLSNEATVARTAILNNIGADGAWVSG    (SEQ ID NO: 27)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASLKRDI
QMTQSPSSLSASVGDRVTITCRASQDVNTAVAWYQQKPGKAPKLLIYSASFLYSGVPSR
FSGSRSGTDFTLTISSLQPEDFATYYCQQHYTTPPTFGQGTKVEIKRTVAAPSVFIFPPSD
EQLKSGTASVVCLLNNFYPREAKVQWKVDNALQSGNSQESVTEQDSKDSTYSLSSTLT
LSKADYEKHKVYACEVTHQGLSSPVTKSFNRGEC.
```

Glucoamylase-light chain fusion protein encoded by pQ91:

```
MSFRSLLALSGLVCTGLANVISKRATLDSWLSNEATVARTAILNNIGADGAWVSG    (SEQ ID NO: 28)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASISKRDI
QMTQSPSSLSASVGDRVTITCRASQDVNTAVAWYQQKPGKAPKLLIYSASFLYSGVPSR
FSGSRSGTDFTLTISSLQPEDFATYYCQQHYTTPPTFGQGTKVEIKRTVAAPSVFIFPPSD
EQLKSGTASWCLLNNFYPREAKVQWKVDNALQSGNSQESVTEQDSKDSTYSLSSTLT
LSKADYEKHKVYACEVTHQGLSSPVTKSFNRGEC.
```

Glucoamylase-light chain fusion protein encoded by pQ94:

```
MSFRSLLALSGLVCTGLANVISKRATLDSWLSNEATVARTAILNNIGADGAWVSG    (SEQ ID NO: 29)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
```

-continued

```
QPCSPRALANHKEWDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSWPASWGETSAS
SVPGTCAATSAIGTYSSVTVTSWPSIVATGGTTTTATPTGSGSVTSTSKTTATASNVISK
RDIQMTQSPSSLSASVGDRVTITCRASQDVNTAVAWYQQKPGKAPKLLIYSASFLYSGV
PSRFSGSRSGTDFTLTISSLQPEDFATYYCQQHYTTPPTFGQGTKVEIKRTVAAPSVFIFP
PSDEQLKSGTASWCLLNNFYPREAKVQWKVDNALQSGNSQESVTEQDSKDSTYSLSS
TLTLSKADYEKHKVYACEVTHQGLSSPVTKSFNRGEC.
```

Glucoamylase-light chain fusion protein encoded by pQ95:

```
    MSFRSLLALSGLVCTGLANVISKRATLDSWLSNEATVARTAILNNIGADGAWVSG   (SEQ ID NO: 30)
ADSGIWASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASVISKR
DIQMTQSPSSLSASVGDRVTITCRASQDVNTAVAWYQQKPGKAPKLLIYSASFLYSGVP
SRFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC.
```

Glucoamylase-light chain fusion protein encoded by pQ96:

```
    MSFRSLLALSGLVCTGLANVISKRATLDSWLSNEATVARTAILNNIGADGAWVSG   (SEQ ID NO: 31)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASISKRG
GGDIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKRTVAAPSVFIF
PPSDEQLKSGTASVVCLLNNFYPREAKVQWKVDNALQSGNSQESVTEQDSKDSTYSLS
STLTLSKADYEKHKVYACEVTHQGLSSPVTKSFNRGEC.
```

DNA of the expression plasmids pQ87, pQ88, pQ90, pQ91, pQ94, pQ95 and pQ96 were prepared and each was transformed individually into *Aspergillus niger* var. *awamori strain dgr*246ΔGAP:pyr2-. The transformants obtained were cultured in shake flasks in Promosoy special medium and the secreted proteins were visualized by SDS-PAGE and Coomassie Brilliant Blue staining. Cleavage of the glucoamylase-light chain fusion protein was assessed by examining the relative amounts of the 25 kD band corresponding to the trastuzumab light chain which had been released from the fusion protein, the 58 kD band corresponding to the catalytic core and linker region of glucoamylase which had been released from the fusion protein and the approximately 85 kD band corresponding to the glucoamylase-light chain fusion protein which had not been cleaved into separate glucoamylase and light chain proteins. In addition, the N-terminus of the released light chain was determined in some instances.

The extent of cleavage of the glucoamylase-light chain fusion protein was apparently unchanged, at approximately 25 to 40%, in *A. niger* transformants with the expression vectors pQ87, pQ88 or pQ90 compared to transformant Q83-35-2.

In contrast, approximately 90% of the glucoamylase-light chain fusion protein was cleaved in transformants with expression vectors pQ91, pQ94 and pQ95. The amino terminus of the free light chain in the supernatants of one transformant obtained with each of pQ91 and pQ94 was determined and a single dominant sequence of DIQMT (SEQ ID NO:41) was observed. This demonstrated that not only the extent of cleavage was improved in transformants with these expression vectors but also frequency at which the fusion protein was cleaved at the expected KEX2 site, i.e., the accuracy or fidelity of the cleavage had been improved.

100% of the glucoamylase-light chain fusion protein was apparently cleaved in transformants with expression vector pQ96. The amino terminus of the free light chain in the supernatant of one transformant obtained with pQ96 was determined and a single dominant sequence of GGGDI (SEQ ID NO:42) was observed.

Example 11

Trastuzumab Heavy Chain Expression in *Aspergillus*

DNA of the integrative expression plasmid pCL1 was prepared and transformed into *Aspergillus niger* var. *awamori* strain dgr246ΔGAM. Transformants were cultured in liquid medium in shake flasks as above. In some experiments, the trastuzumab heavy chain was specifically precipitated from the supernatant by incubation with protein A-sepharose beads (Amersham Pharmacia) which has specific affinity for the heavy chain of IgG. The beads were pre-washed in SDS-PAGE running buffer and were further washed in this buffer after incubation with heavy chain and before being resuspended in SDS-PAGE sample buffer, heating at 70° C. for 10 minutes prior and loading on a polyacrylamide gel. Samples of supernatant, or of material precipitated from supernatant with protein A-sepharose, were analyzed by SDS-polyacrylamide gel electrophoresis (SDS-PAGE) under reducing conditions followed by Coomassie Brilliant Blue staining of the protein bands or blotting to nylon membranes for Western analysis. Trastuzumab heavy chain was visualized on Western blots by sequential treatment with goat anti-human IgG-Fc antibody and rabbit anti-goat IgG conjugated with horse radish peroxidase (HRP) followed by HRP color development by incubation with $H_2O_2$ and 4-chloro-1-napthol. Transformants which produced trastuzumab heavy chain were identified by the appearance of extra protein bands compared to supernatant from the untransformed parental strain. The sizes and identities of these bands were as follows. A pair of bands, one at 50 kD (which has the same mobility on SDS-PAGE as the secreted alpha-amylase of *Aspergillus niger*), and one at approximately 53 KD, both corresponding to the trastuzumab heavy chain which had been released from the glucoamylase-heavy chain fusion protein (the appearance of free heavy chain of two different sizes is explained below). A band with an apparent molecular weight of 58 kD corresponding to the catalytic core and linker region of glucoamylase which had been released from the glucoamylase-heavy chain fusion protein. A band with an apparent molecular weight of 116 kD corresponding to the glucoamylase-heavy chain fusion protein which had not been cleaved into separate glucoamylase and heavy chain proteins. The best heavy-chain expressing transformant produced approximately 0.33 g per liter of culture supernatant of trastuzumab gamma heavy chain according to ELISA. The ELISA was performed using goat anti-human IgG-Fc antibody as a capture antibody coating the wells of microtiter plates. After adding appropriately diluted culture supernatant, incubation, and then washing the wells, the bound heavy chain from the supernatant was detected by addition of goat anti human IgG-Fc antibody conjugated with HRP followed by a color development reaction. A serial dilution of known concentration of human IgG was used to produce a standard for quantification purposes.

Example 12

Trastuzumab Heavy and Light Chain Expression in Aspergillus

Three different transformation strategies were used to construct *Aspergillus* transformants which produced both heavy and light chains of the trastuzumab antibody.

Strain construction by co-transformation. The expression plasmids pQ83 and pCL1 were mixed and transformed into *Aspergillus niger* var. *awamori* strain dgr246ΔGAM. Neither of these plasmids has a fungal origin of replication and would be expected to integrate into the *Aspergillus* chromosomal DNA at one or more sites. Transformants were cultured in shake flasks as described above and light and heavy chain production was evident from SDS-PAGE and Western analysis. A mix of the same light chain and heavy chain bands were observed as seen in the transformants which produced only light chain or only heavy chain. Up to approximately 0.3 g/l assembled IgG was measured by ELISA in shake flask cultures of the best transformant (1-LC/HC-3). The ELISA was performed using goat anti-human IgG-Fc antibody as a capture antibody coating the wells of microtiter plates. After adding appropriately diluted culture supernatant, incubation; and then washing the wells, the bound IgG1 from the supernatant was detected by addition of an goat anti human κ (bound and free) antibody conjugated with HRP followed by a color development reaction. By employing this combination of capture and detection antibodies in the ELISA, only assembled IgG1 would be measured whereas free light chain and heavy chain would not be measured. A serial dilution of known concentration of purified human IgG was used to produce a standard for quantification purposes. The capture and detection antibodies were reversed in some experiments so that the capture antibody was anti human K antibody and the detection antibody was anti-human IgG-Fc antibody conjugated with HRP. Results were comparable with either combination of antibodies.

Transformants were also obtained by co-transformation with the expression plasmids pQ83 and pCL5. These plasmids were mixed and transformed into *Aspergillus niger* var. *awamori* strain dgr246ΔGAM. Up to 0.9 g/l assembled IgG was measured by ELISA in shake flask cultures of the best transformant (2-LC/HC-38).

Strain construction using a replicating plasmid. The plasmids pQ83, pCL1 and pHELP1 were mixed and transformed into *Aspergillus niger* var. *awamori strain dgr*246ΔGAM. The plasmid pHELP1 (Gems, D. and Clutterbuck, A. J., 1993, Curr. Genet. 24:520-524) includes an *Aspergillus nidulans* sequence, AMA1, which confers autonomous replication in *aspergillus* strains. Based on previous results (Gems, D. and Clutterbuck, A. J., 1993, Curr. Genet. 24:520-524) it would be expected that the plasmids would recombine with one another and form a large replicating plasmid that contains elements of all three plasmids. Transformants were cultured in shake flasks and analyzed for expression of the trastuzumab heavy and light chains by SDS-PAGE and Western analysis. A mix of the same light chain and heavy chain bands were observed as seen in the transformants which produced only light chain or only heavy chain. Assembled IgG1 was assayed by ELISA. Up to 0.26 g/l assembled IgG was measured by ELISA in shake flask cultures.

Strain construction by two sequential transformations. The integrative plasmid pCL1 (heavy chain expression plasmid) was used to transform strain Q83-35-2, the best light chain producing strain identified above. Transformants were cultured in shake flasks and analyzed for expression of the trastuzumab heavy and light chains by SDS-PAGE and Western analysis. A mix of the same light chain and heavy chain bands were observed as seen in the transformants which produced only light chain or only heavy chain. Assembled IgG1 was assayed by ELISA. Up to 0.19 g/l assembled IgG was measured by ELISA in shake flask cultures.

In some experiments, the trastuzumab heavy chain and associated light chain was specifically precipitated from the supernatant by incubation with Protein A-Sepharose 4 Fast Flow beads (Amersham Pharmacia, Piscataway, N.J.) as above. Purification of the heavy chain and associated light chain was also performed using affinity chromatography on a HiTrap Protein A HP chromatography column (Amersham Pharmacia, Piscataway, N.J.) following the manufacturers protocol. FIG. 8 shows the results of SDS-PAGE under reducing conditions and with Coomassie Brilliant Blue staining of samples which had been purified by protein A chromatography. The bands observed for transformant 1-LC/HC-3 were identified as the light chain (25 kDa), non-glycosylated and glycosylated forms of the heavy chain (50 and 53 kDa), glucoamylase-light chain fusion protein (85 kDa) and glucoamylase-heavy chain fusion (116 kDa). The fact that light chain was co-purified with heavy chain by Protein A affinity chromatography (which is specific for heavy chain) demonstrated that the antibody was assembled. The fact that both glucoamylase-heavy chain and glucoamylase-light chain fusion proteins co-purified by Protein A affinity chromatography demonstrated that the antibody assembled with glucoamylase attached.

FIG. 9 shows the results of SDS-PAGE (NuPAGE Tris-Acetate Electrophoresis System from Invitrogen Corporation, Carlsbad, Calif.) under non-reducing conditions and with Coomassie Brilliant Blue staining of samples which had been purified by protein A chromatography. The major bands observed for transformant 1-LC/HC-3 were identified as assembled IgG1 (150 kDa), assembled IgG1 with one molecule of glucoamylase attached (~200 kDa) and assembled IgG1 with two molecules of glucoamylase attached (~250 kDa).

In order to understand why the two forms of the free heavy chain (i.e., that heavy chain which was released from the glucoamylase-heavy chain fusion protein) were produced differing in apparent molecular weight by approximately 3 kD, the following experiments were performed. The trastuzumab produced by *Aspergillus* was purified by protein A affinity chromatography. Samples of the purified trastuzumab were incubated for 1 hour in the presence or absence of 35 ug of endo-β-N-acetylglucosaminidase H (endo H) which is able to cleave high mannose type N-linked glycosylation from proteins leaving a single N-acetylglucosamine sugar attached to the asparagine of the protein. These samples were analyzed by SDS-PAGE under reducing conditions followed by Coomassie Brilliant Blue staining for proteins or staining which is specific for glycoproteins (GelCode Glycoprotein Staining Kit from Pierce, Rockford, Ill. used according to the manufactures instructions). The upper of the two bands of free heavy chain was greatly reduced in intensity by treatment with endo H. Only the upper free heavy chain band was stained with GelCode stain and this band was no longer visible with GelCode staining after endo H treatment. These observations indicate that the upper of the two free heavy chain bands represents heavy chain with N-linked high mannose glycan attached and that endo H treatment is able to remove this glycan.

It was possible to purify and separate the free IgG1 from the glucoamylase-IgG1 fusion proteins. The method used for purification was hydrophobic charge induction chromatography as described in co-pending application U.S. Ser. No. 60/411,537 filed Sep. 18, 2002, entitled “Protein Purification”. Firstly, fungal cells were removed from culture broth by filtration through Miracloth (Calbiochem, San Diego, Calif.). The filtered broth was concentrated approximately seven-fold by tangential ultrafiltration. Using a circulating pump, the broth was pressurized and flowed across a membrane made of regenerated cellulose with a 30,000 molecular weight cutoff (Prep/Scale™ TFF, Millipore). To remove particulates, the concentrate was centrifuged at 25,000 times gravity for 15 minutes, and the supernatant was filtered through a series of membranes, with each membrane having a smaller pore size than the previous, ending with 0.2-micrometer pore size. IgG1 was purified from supernatant using hydrophobic charge induction chromatography (HCIC) This was performed with the aid of a high performance liquid chromatographic system (AKTA™ explorer 10, Amersham Biosciences). HCIC provided an ability to separate antibody molecules from other supernatant proteins and from glucoamylase-fusion proteins. It was carried out using a column containing MEP HyperCel® (Ciphergen Biosystems) media. The column was equilibrated with 50 mM Tris, 200 mM NaCl, and pH 8.2 buffer. Supernatant, adjusted to pH 8.2, was applied to the column at a linear flow rate of 100 cm/h. After washing with five column volumes (5 CV) of equilibration buffer, bound molecules were eluted by incrementally decreasing the pH. Two CV of each of the following buffers were delivered to the column at 200 cm/h, in the order listed: 100 mM sodium acetate, pH 5.6; 100 mM sodium acetate, pH 4.75; 100 mM sodium acetate, pH 4.0; and 100 mM sodium citrate, pH 2.5. Free IgG1 eluted within the pH range 4.5-5.5 and was immediately neutralized with 1 M Tris and pH 8.2 buffer. The purity of the antibody exiting the column was assessed by SDS-PAGE.

Example 13

A Glycosylated Trastuzumab Expression in *Aspergillus*

The plasmid pCL3 (the expression vector for the aglycosylated mutant form of the heavy chain) was used to transform strain Q83-35-2, the best light chain producing strain identified above. Transformants were cultured in shake flasks. Both light chain and heavy chain expression was evident from SDS-PAGE after precipitation of the heavy chain with protein A-sepharose beads or after purification by protein A affinity chromatography. A mix of the same light chain and heavy chain bands were observed on SDS-PAGE under reducing conditions as seen in transformant 1-LC/HC-3 except that only a single band of free heavy chain at 50 kD was observed (strain 1-HCΔ4 in FIG. 8). A similar pattern of bands were observed on SDS-PAGE under non-reducing conditions as seen in transformant 1-LC/HC-3 (strain 1-HCΔ4 in FIG. 9). Fully assembled IgG1 was measured by ELISA. 0.1 g/l of aglycosylated trastuzumab was produced in shake flask cultures by the best transformant.

Example 14

Trastuzumab Fab' Fragment Expression in Aspergillus

The plasmid pCL2 (the expression vector for the Fd' fragment of the trastuzumab heavy chain) was used to transform strain Q83-35-2, the best light chain producing strain identified above. Transformants were cultured in shake flasks. Assembled Fab' was measured by ELISA. Two transformants were studied in more detail; 1-Fab-1 and 1-Fab-12. 1.2 g/l Fab' was produced in shake flask cultures by the best transformant (strain 1-Fab-12). Expression of the Fab' fragment of the trastuzumab was evident from SDS-PAGE after precipitation of the heavy chain with protein A-sepharose beads or after purification by protein A affinity chromatography. SDS-PAGE under reducing conditions showed a band at approximately 25 kDa representing both the light chain and Fd' chains as well as a band at approximately 85 kDa representing both the glucoamylase-light chain and glucoamylase-Fd' chain fusion proteins (strain 1-Fab-1 in FIG. 8). The major bands observed on SDS-PAGE under non-reducing conditions were one at approximately 50 kDa representing the assembled Fab' and one at approximately 100 kDa representing Fab' with a single glucoamylase molecule attached (strain 1-Fab-1 in FIG. 9). A fainter band at approximately 150 kDa may represent Fab' with glucoamylase molecules attached to both the light chain and the Fd' chain. It is of interest to determine if Fab' produced by *A. niger* can covalently dimerize through the free cysteines near the carboxyl terminus of the Fd' chain to form $F(ab')_2$. The size of $F(ab')_2$ would be approximately 100 kDa and would therefore run at the same position as Fab' with a single glucoamylase molecule attached on non-reducing SDS-PAGE. Similarly, the size of $F(ab')_2$ with one glucoamylase attached would be approximately 150 kDa and would therefore run at the same position as Fab' with two glucoamylase molecules attached. However, the higher molecular weight band at approximately 200 kDa observed for strain 1-Fab-1 in FIG. 9 is best explained as representing F(ab')$_2$ with two glucoamylase molecules attached.

To confirm that F(ab')$_2$ was secreted by transformant 1-Fab-12 the secreted antibody fragments were purified to separate the Fab' and F(ab')$_2$ from the glucoamylase-Fab' and glucoamylase-F(ab')$_2$ fusion proteins. The method used for purification was hydrophobic charge induction chromatography as described in co-pending application U.S. Ser. No. 60/411,537 filed Sep. 18, 2002, entitled "Protein Purification" followed by size exclusion chromatography. Firstly, fungal cells were removed from culture broth by filtration through Miracloth (Calbiochem, San Diego, Calif.). The filtered broth was concentrated approximately seven-fold by tangential ultrafiltration. Using a circulating pump, the broth was pressurized and flowed across a membrane made of regenerated cellulose with a 30,000 molecular weight cutoff (Prep/Scale™ TFF, Millipore). To remove particulates, the concentrate was centrifuged at 25,000 times gravity for 15 minutes, and the supernatant was filtered through a series of membranes, with each membrane having a smaller pore size than the previous, ending with 0.2-micrometer pore size. Fab' (monomer and dimer) antibody fragments were purified from supernatant using a combination of hydrophobic charge induction chromatography (HCIC) and size exclusion chromatography (SEC). Each of these methods was performed with the aid of a high performance liquid chromatographic system (AKTA™ explorer 10, Amersham Biosciences). HCIC provided an ability to separate antibody molecules from other supernatant proteins and from glucoamylase-fusion proteins. SEC served to separate Fab from F(ab')$_2$. HCIC was carried out using a column containing MEP HyperCel® (Ciphergen Biosystems) media. The column was equilibrated with 50 mM Tris, 200 mM NaCl, and pH 8.2 buffer. Supernatant, adjusted to pH 8.2, was applied to the column at a linear flow rate of 100 cm/h. After washing with five column volumes (5 CV) of equilibration buffer, bound molecules were eluted by incrementally decreasing the pH. Two CV of each of the following buffers were delivered to the column at 200 cm/h, in the order listed: 100 mM sodium acetate, pH 5.6; 100 mM sodium acetate, pH 4.75; 100 mM sodium acetate, pH 4.0; and 100 mM sodium citrate, pH 2.5. Fab' and F(ab')$_2$ eluted within the pH range 4.5-5.5 and were immediately neutralized with 1 M Tris and pH 8.2 buffer. A HiLoad™ 26/60 column with Superdex 200™ Prep Grade media (Amersham Biosciences) was used for SEC. The flow rate was kept at 17 cm/h. After equilibrating the column with 20 mM sodium acetate, 136 mM NaCl, and pH 5.5 buffer; a 6.5-mL sample was driven through the column with 1 CV of equilibration buffer. The purity of the antibody exiting the column was assessed by SDS-PAGE.

On SDS-PAGE under reducing conditions the Fd' and light chains of the HCl-purified Fab' and F(ab')$_2$ both run as bands of 25 kDa (FIG. 10). Under these conditions it is clear that no glucoamylase-light chain or glucoamylase-Fd' fusion proteins are present in the purified samples because these would run as a band of approximately 50 kDa. On SDS-PAGE under non-reducing conditions it is clear that F(ab')$_2$ is present in the purified samples (Fraction A5 in FIG. 10) because this runs as a band of approximately 100 kDa compared to the 50 kDa of Fab' (Fraction B7 in FIG. 10).

Example 15

Assays to Demonstrate that Trastuzumab Made in *Aspergillus* is Functional (it Binds to and Inhibits Proliferation of her2 Expressing Breast Cancer Cells)

The effect of the trastuzumab produced by *Aspergillus* transformant 1-LC/HC-3 was compared to that of commercial trastuzumab (Herceptin, Genentech, South San Francisco, Calif.) on the proliferation of a human breast adenocarcinoma cell line, SK-BR-3 (ATCC number: HTB-30), which expresses high levels of HER2. In order to assay proliferation of the cells in 96 well microtiter plates the "CellTiter 96 Aqueous One Solution Cell Proliferation Assay" (Promega Corporation, Madison, Wis.) was used according to the manufacturers instructions. SK-BR-3 cells were plated at 1800 cells per well and allowed to adhere for 6 hours prior to antibody addition then assayed 72 hours later. Protein A purified IgG1 from transformant 1-LC/HC-3 was tested for anti-proliferative effects on SK-BR-3 cells relative to Herceptin and untreated cells. As a control cell line A-431 cells (ATCC number: CRL-1555) were used. A-431 is human epidermoid carcinoma that expresses high levels of the EGF receptor and low levels of HER2. Herceptin should have little or no anti-proliferative effect on this cell line. Data is presented as the percent proliferation (mean of triplicate wells) relative to untreated cells (see FIG. 11). These results are in excellent agreement with the reported anti-proliferative effects of trastuzumab on the SK-BR-3 cell line (Carter, P. et al., 1992, Proc. Natl. Acad. Sci. USA 89:4285-4289) and demonstrate that the antibody purified from culture supernatant of transformant 1-LC/HC-3 is assembled and functional in its ability to bind to the specific antigen, HER2.

Example 16

Production of Hu1D10 Antibody in *Aspergillus*

Expression vectors were constructed in the same manner as described in Example 10 to allow the production of the light and heavy chains of Hu1D10 antibody (of the IgG1κ subclass; Kostelny, S. a. et al., 2001, Int. J. Cancer 93:556-565) in *Aspergillus niger*. The cDNA encoding Hu1D10 was modified by site directed mutagenesis to remove internal BstEII sites. PCR primers were designed to amplify and add NheI sites at the 5 end, add BstEII sites at the 3 end and to add specific codons at the 5 ends.

Two forms of the cDNA encoding the Hu1D10 light chain were generated which varied at the 5 end sequence. The cDNA sequence encoding the Q101 form of Hu1D10 light chain was as follows. The nucleotides represented in lower case are those added by the PCR primers.

```
     GctagcatctccaagcgcGACATCCAGATGACTCAGTCTCCATCTTCTCTATCTGCAT  (SEQ ID NQ: 32)
CTGTGGGAGACAGGGTCACAATCACATGTCGAGCAAGTGAAAATATTTACAGTTATT
TAGCATGGTACCAGCAGAAACCTGGAAAAGCTCCTAAGCTCCTGGTCTCTAATGCTA
AAACCTTAGCAGAAGGTGTGCCATCAAGGTTCAGTGGCAGTGGATCAGGCAAACAG
TTTACTCTGACAATCAGCAGCCTGCAGCCTGAAGATTTTGCTACTTATTACTGTCAAC
ATCATTATGGTAATTCGTACCCGTTCGGACAGGGGACCAAACTGGAAATAAAACGAA
CTGTGGCTGCACCATCTGTCTTCATCTTCCCGCCATCTGATGAGCAGTTGAAATCTG
GAACTGCCTCTGTTGTGTGCCTGCTGAATAACTTCTATCCCAGAGAGGCCAAAGTAC
AGTGGAAGGTGGATAACGCCCTCCAATCGGGTAACTCCCAGGAGAGTGTCACAGAG
CAGGACAGCAAGGACAGCACCTACAGCCTCAGCAGCACCCTGACGCTGAGCAAAGC
```

-continued

```
AGACTACGAGAAACACAAAGTCTACGCCTGCGAAGTCACCCATCAGGGCCTGAGCT
CGCCCGTCACAAAGAGCTTCAACAGGGGAGAGTGTTAGggtgacc.
```

The cDNA sequence encoding the Q100 form of Hu1D10 light chain was as follows. The nucleotides represented in lower case are those added by the PCR primers.

```
     GctagcatctccaagcgcggtggcggaGACATCCAGATGACTCAGTCTCCATCTTCTCTA  (SEQ ID NO: 33)
TCTGCATCTGTGGGAGACAGGGTCACAATCACATGTCGAGCAAGTGAAAATATTTAC
AGTTATTTAGCATGGTACCAGCAGAAACCTGGAAAAGCTCCTAAGCTCCTGGTCTCT
AATGCTAAAACCTTAGCAGAAGGTGTGCCATCAAGGTTCAGTGGCAGTGGATCAGG
CAAACAGTTTACTCTGACAATCAGCAGCCTGCAGCCTGAAGATTTTGCTACTTATTAC
TGTCAACATCATTATGGTAATTCGTACCCGTTCGGACAGGGGACCAAACTGGAAATA
AAACGAACTGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGT
CACAGAGCAGGACAGCAAGGACAGCACCTACAGCCTCAGCAGCACCCTGACGCTGA
GCAAAGCAGACTACGAGAAACACAAAGTCTACGCCTGCGAAGTCACCCATCAGGGC
CTGAGCTCGCCCGTCACAAAGAGCTTCAACAGGGGAGAGTGTTAGggtgacc.
```

The above amplified light chain cDNAs could then be inserted into the *Aspergillus* expression vector to create pQ101 or pQ100. The *Aspergillus niger* var *awamori* glaA (glucoamylase) promoter and *A. niger* glaA terminator were present in the plasmid to control expression of the open reading frame which included the light chain encoding cDNA.

Plasmid pQ101 was designed for the expression of a fusion protein with the amino acid sequence shown below and consisting of the glucoamylase signal sequence, prosequence, catalytic domain and linker region up to amino acid number 498 (a serine) of mature glucoamylase (Nunberg, J. H. et al., 1984, Mol. Cell. Biol. 4:2306-2315), followed by amino acids ISKR (underlined below) and then by the mature Hu1D10 light chain. This plasmid did not include a selectable marker for *Aspergillus* transformation.

```
     MSFRSLLALSGLVCTGLANVISKRATLDSWLSNEATVARTAILNNIGADGAWVSG    (SEQ ID NO: 34)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASISKRDI
QMTQSPSSLSASVGDRVTITCRASENIYSYLAWYQQKPGKAPKLLVSNAKTLAEGVPSR
FSGSGSGKQFTLTISSLQPEDFATYYCQHHYGNSYPFGQGTKLEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC.
```

Plasmid pQ100 was designed for the expression of a fusion protein with the amino acid sequence shown below and consisting of the glucoamylase signal sequence, prosequence, catalytic domain and linker region up to amino acid number 498 (a serine) of mature glucoamylase (Nunberg, J. H. et al. 1984 Mol. Cell. Biol. 4:2306-2315), followed by amino acids ISKRGGG (underlined below) and then by the mature Hu1D10 light chain. This plasmid also contained the *A. niger* pyrG gene as a selectable marker for *Aspergillus* transformation.

```
     MSFRSLLALSGLVCTGLANVISKRATLDSWLSNEATVARTAILNNIGADGAWVSG  (SEQ ID NO: 35)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
```

-continued

```
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASISKRG
GGDIQMTQSPSSLSASVGDRVTITCRASENIYSYLAWYQQKPGKAPKLLVSNAKTLAEG
VPSRFSGSGSGKQFTLTISSLQPEDFATYYCQHHYGNSYPFGQGTKLEIKRTVAAPSVFI
FPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC.
```

Two forms of the cDNA encoding the Hu1D10 heavy chain were generated which varied at the 5 end sequence. The cDNA sequence encoding the CL17 form of Hu1D10 light chain was as follows. The nucleotides represented in lower case are those added by the PCR primers.

```
     gctagcatctccaagcgcCAGGTGCAGCTGCAGGAGTCAGGACCAGGCCTAGTGAA   (SEQ ID NO: 36)
GCCCTCAGAGACTCTGTCCCTAACCTGCACAGTCTCTGGTTTCTCATTAACTAACTAT
GGTGTACACTGGGTTCGCCAGTCTCCAGGAAAGGGTCTGGAATGGATCGGAGTGAA
ATGGAGTGGTGGGTCGACAGAATATAATGCAGCTTTCATATCCAGACTGACCATCAG
CAAGGACACCTCCAAGAACCAAGTTTCCCTTAAACTGAACAGTCTGACCGCTGCTGA
CACAGCCGTGTACTACTGTGCCAGAAATGATAGATATGCTATGGACTACTGGGGTCA
AGGAACTCTAGTCACCGTCTCCTCAGCCTCCACCAAGGGCCCATCGGTCTTCCCCC
TGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCA
GCGGCGTGCACACCTTCCCGGCTGTCCTACAGTCCTCAGGACTCTACTCCCTGAGC
AGCGTGGTGACAGTGCCCTCCAGCAGCTTGGGCACCCAGACCTACATCTGCAACGT
GAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGA
GGTCACATGCGTGGTGGTGGACGTGAGCCACGAAGACCCTGAGGTCAAGTTCAACT
GGTACGTGGACGGCGTGGAGGTGCATAATGCCAAGACAAAGCCGCGGGAGGAGCA
GTACAACAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTACACCCT
GCCCCCATCCCGGGATGAGCTGACCAAGAACCAGGTCAGCCTGACCTGCCTGGTCA
AAGGCTTCTATCCCAGCGACATCGCCGTGGAGTGGGAGAGCAATGGGCAGCCGGA
GAACAACTACAAGACCACGCCTCCCGTGCTGGACTCCGACGGCTCCTTCTTCCTCT
ACAGCAAGCTCACCGTGGACAAGAGCAGGTGGCAGCAGGGGAACGTCTTCTCATGC
TCCGTGATGCATGAGGCTCTGCACAACCACTACACGCAGAAGAGCCTCTCCCTGTC
TCCGGGTAAATGAggtgacc.
```

The cDNA sequence encoding the CL16 form of Hu1D10 heavy chain was as follows. The nucleotides represented in lower case are those added by the PCR primers.

```
     gctagcatctccaagcgcggtggcggaCAGGTGCAGCTGCAGGAGTCAGGACCAGGCCT   (SEQ ID NO: 37)
AGTGAAGCCCTCAGAGACTCTGTCCCTAACCTGCACAGTCTCTGGTTTCTCATTAAC
TAACTATGGTGTACACTGGGTTCGCCAGTCTCCAGGAAAGGGTCTGGAATGGATCG
GAGTGAAATGGAGTGGTGGGTCGACAGAATATAATGCAGCTTTCATATCCAGACTGA
CCATCAGCAAGGACACCTCCAAGAACCAAGTTTCCCTTAAACTGAACAGTCTGACCG
CTGCTGACACAGCCGTGTACTACTGTGCCAGAAATGATAGATATGCTATGGACTACT
GGGGTCAAGGAACTCTAGTCACCGTCTCCTCAGCCTCCACCAAGGGCCCATCGGTC
TTCCCCCTGGCACCCTCCTCCAAGAGCACCTCTGGGGGCACAGCGGCCCTGGGCT
GCCTGGTCAAGGACTACTTCCCCGAACCGGTGACGGTGTCGTGGAACTCAGGCGC
CCTGACCAGCGGCGTGCACACCTTCCCGGCTGTCCTACAGTCCTCAGGACTCTACT
CCCTCAGCAGCGTGGTGACAGTGCCCTCCAGCAGCTTGGGCACCCAGACCTACATC
TGCAACGTGAATCACAAGCCCAGCAACACCAAGGTGGACAAGAAAGTTGAGCCCAA
ATCTTGTGACAAAACTCACACATGCCCACCGTGCCCAGCACCTGAACTCCTGGGGG
GACCGTCAGTCTTCCTCTTCCCCCCAAAACCCAAGGACACCCTCATGATCTCCCGGA
CCCCTGAGGTCACATGCGTGGTGGTGGACGTGAGCCACGAAGACCCTGAGGTCAA
GTTCAACTGGTACGTGGACGGCGTGGAGGTGCATAATGCCAAGACAAAGCCGCGG
GAGGAGCAGTACAACAGCACGTACCGTGTGGTCAGCGTCCTCACCGTCCTGCACCA
GGACTGGCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCACAGGTG
TACACCCTGCCCCCATCCCGGGATGAGCTGACCAAGAACCAGGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTC
TTCCTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCCTCT
CCCTGTCTCCGGGTAAATGAggtgacc.
```

The above amplified heavy chain cDNAs could then be inserted into the *Aspergillus* expression vector to create pCL17 or pQCL16. The *Aspergillus niger* var *awamori* glaA (glucoamylase) promoter and *A. niger* glaA terminator were present in the plasmid to control expression of the open reading frame which included the heavy chain encoding DNA.

Plasmid pCL17 was designed for the expression of a fusion protein with the amino acid sequence shown below and consisting of the glucoamylase signal sequence, prosequence-catalytic domain and linker region up to amino acid number 498 (a serine) of mature glucoamylase (Nunberg, J. H. et al., , 1984, Mol. Cell. Biol. 4:2306-2315), followed by amino acids ISKR (underlined below) and then by the mature Hu1D10 heavy chain. This plasmid also contained the *A. niger* pyrG gene as a selectable marker for *Aspergillus* transformation.

MSFRSLLALSGLVCTGLANVISKRATLDSWLSNEATVARTAILNNIGADGAWVSG (SEQ ID NO: 38)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASISKRQ
VQLQESGPGLVKPSETLSLTCTVSGFSLTNYGVHWVRQSPGKGLEWIGVKWSGGSTE
YNAAFISRLTISKDTSKNQVSLKLNSLTAADTAVYYCARNDRYAMDYWGQGTLVTVSSA
STKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDK
SRWQQGNVFSCSVMHEALHNHYTQKSLSLSPGK.

Plasmid pCL16 was designed for the expression of a fusion protein with the amino acid sequence shown below and consisting of the glucoamylase signal sequence, prosequence, catalytic domain and linker region up to amino acid number 498 (a serine) of mature glucoamylase (Nunberg, J. H. et al., 1984, Mol. Cell. Biol. 4:2306-2315), followed by amino acids ISKRGGG (underlined below) and then by the mature Hu1D10 heavy chain. This plasmid did not include a selectable marker for *Aspergillus* transformation.

MSFRSLLALSGLVCTGLANVISKRATLDSWLSNEATVARTAILNNIGADGAWVSG (SEQ ID NO: 39)
ADSGIVVASPSTDNPDYFYTWTRDSGLVLKTLVDLFRNGDTSLLSTIENYISAQAIVQGIS
NPSGDLSSGAGLGEPKFNVDETAYTGSWGRPQRDGPALRATAMIGFGQWLLDNGYTS
TATDIVWPLVRNDLSYVAQYWNQTGYDLWEEVNGSSFFTIAVQHRALVEGSAFATAVG
SSCSWCDSQAPEILCYLQSFWTGSFILANFDSSRSGKDANTLLGSIHTFDPEAACDDSTF
QPCSPRALANHKEVVDSFRSIYTLNDGLSDSEAVAVGRYPEDTYYNGNPWFLCTLAAAE
QLYDALYQWDKQGSLEVTDVSLDFFKALYSDAATGTYSSSSSTYSSIVDAVKTFADGFV
SIVETHAASNGSMSEQYDKSDGEQLSARDLTWSYAALLTANNRRNSVVPASWGETSAS
SVPGTCAATSAIGTYSSVTVTSWPSIVATGGTTTTATPTGSGSVTSTSKTTATASISKRG
GGQVQLQESGPGLVKPSETLSLTCTVSGFSLTNYGVHWVRQSPGKGLEWIGVKWSGG
STEYNAAFISRLTISKDTSKNQVSLKLNSLTAADTAVYYCARNDRYAMDYWGQGTLVTVS
SASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK.

Plasmids pQ101 and pCL17 were co-transformed into *Aspergillus niger* var *awamori* strain dgr246ΔGAP:pyr2- by the methods described in Examples 9 and 12. The best Hu1D10 producing transformant (3-Hu1D10-20e) was identified and found to produce approximately 0.2 g/l of IgG1κ.

Plasmids pQ100 and pCL16 were co-transformed into *Aspergillus niger* var *awamori* strain dgr246ΔGAP:pyr2- by the methods described in Examples 9 and 12. The best Hu1D10 producing transformant (2-Hu1D10-16b) was identified and found to produce approximately 0.2 g/l of IgG1κ.

Antibody was purified from culture supernatant of these transformants by the methods described in Example 12. The purified antibody preparation obtained from strain 3-Hu1D10 was designated An-Hu1D10 and that from strain 2-Hu1D10-16b was designated An-3G-Hu1D10.

Example 17

Antibody Affinity and Avidity

The human Burkitt's lymphoma-derived cell line Raji (ATCC, Manassas, Va.), which expresses the HLA-DR β chain allotype recognized by Hu1D10 (Kostelny et al., 2001, Int J Cancer, 93:556), was maintained in RPMI-1640 (Gibco BRL, Grand Island, N.Y.) containing 10% fetal bovine serum (FBS; HyClone, Logan, Utah) in a 7.5% $CO_2$ incubator. The affinity of Hu1D10 binding to HLA-DR β chains was determined by measuring the amount of antibody that bound to Raji cells. Raji cells ($5\times10^5$ cells/test) were incubated with varying amounts (serial 2-fold dilutions starting at 1 μg/test) of control Hu1D10 (derived from the NS0 mouse myeloma cell line), An-Hu1D10 or An-3G-Hu1D10 for 30 min on ice in 100 μl of FACS Staining Buffer (FSB; PBS containing 1% bovine serum albumin and 0.2% sodium azide). After incubation, cells were washed three times in FSB and incubated with fluorescein isothiocyanate (FITC)-conjugated AffiniPure goat anti human IgG antibodies (Jackson ImmunoResearch, West Grove, Pa.) for additional 30 min on ice. The cells were washed three times with FSB and analyzed by flow cytometry using a FACScan (Becton Dickinson, San Jose, Calif.). Antibody concentration (ng/test) was plotted versus mean channel fluorescence (FIG. 12). A competition binding experiment was also performed in which a mixture of FITC-labeled NS0-Hu1D10 (0.25 μg/test) and competitor antibody (serial 2-fold dilutions of control NS0-derived Hu1D10, An-Hu1D10 or An-3G-Hu1D10 starting at 6.25 μg/test) in FSB was added to Raji cells ($5\times10^5$ cells/test) in a final volume of 100 μl per test in duplicate. All samples were incubated on ice for 30 min. The cells were washed three times with FSB and analyzed by flow cytometry. Competitor concentration (ng/test) was plotted versus mean channel fluorescence (FIG. 13). No significant difference was observed in the binding to Raji cells among the NS0-derived and *Aspergillus*-derived Hu1D10 antibodies (FIGS. 12 and 13), indicating that the production of Hu1D10 in *Aspergillus niger* had no measurable effect on the structure of its antigen binding site.

In addition, the avidity of Hu1D10 was measured by monitoring the degree of apoptosis in a population of Raji cells (as determined by staining with FITC-Annexin V and propidium iodide; Vermes, I. et al., 1995, J. Immunol. Methods 184:38-51). To measure the ability control NS0-derived Hu1D10, An-Hu1D10 or An-3G-Hu1D10 antibodies to induce apoptosis, Raji cells resuspended at $5\times10^5$ cells/ml in RPMI-1640 containing 10% FBS were incubated with 2 μg antibody at 37° C. for 5 hr or 24 hr. Cells were then washed three times in 1× binding buffer provided in the Apoptosis Detection Kit (Pharmingen, San Diego, Calif.) and stained with FITC-conjugated annexin V and propidium iodide according to the manufacturer's protocol. Cell death was determined by 2-color flow cytometry. Percent apoptosis was defined as the sum of the percentage of annexin V staining cells and the percentage of annexin V and propidium iodide staining cells. Relative cell fluorescence was analyzed on FACScan (FIG. 14).

No significant difference in ability to induce apoptosis was observed between NS0-Hu1D10, An-Hu1D10 or An-3G-Hu1D10 in these experiments.

Example 18

Antibody-Dependent Cellular Cytotoxicity (ADCC)

The ability of NS0-Hu1D10, An-Hu1D10 or An-3G-Hu1D10 to kill Raji cells by ADCC was measured (Kostelny et al, 2001). ADCC was analyzed with the LDH Detection Kit (Roche Molecular Biochemicals, Indianapolis, Ind.) using human PBMC as effector cells (E) and Raji cells as target cells (T). Human peripheral blood mononuclear cells (PBMC) were isolated from healthy donors using Ficoll-Paque PLUS lymphocyte isolation solution (Amersham Biosciences, Uppsala, Sweden). Target and effector cells were washed in RPMI-1640 (Gibco BRL) supplemented with 1% BSA and added to 96-well U-bottom plates (Becton Dickinson) at an E:T ratio of 40:1. Hu1D10 antibodies were added to the wells at desired concentrations. After a 4 hr incubation at 37° C., all plates were centrifuged and cell-free supernatants were incubated with LDH reaction mixture in separate 96-well flat-bottom plates for 30 min at 25° C. The absorbance of reaction samples was measured at 490 nm. Antibody-independent cellular cytotoxicity (AICC) was measured by adding effector and target cells in the absence of antibodies. Spontaneous release (SR) was measured by adding only target or effector cells. Maximal release (MR) was measured by adding 2% Triton-X100 to target cells. Percent lysis was determined by the following equation: $\{$(LDH release of sample−SR of effector cells−SR of target cells)/(MR of target cells−SR of target cells)$\}\times100$. Each condition was examined in duplicate.

Human PBMC from two different donors were used in the analysis. With donor 1 (FIG. 15, left panel), the maximal cytotoxicity level reached nearly 40% with either of the three Hu1D10 antibodies. In this particular experiment, the *Aspergillus*-derived An-Hu1D10 induced cytotoxicity slightly better than the other two Hu1D10 antibodies. Between the NS0-derived Hu1D10 and the *Aspergillus*-derived An-3G-Hu1D10 antibodies, however, there was no significant difference in induction of cytotoxicity. With donor 2 (FIG. 15, right panel), the maximal cytotoxicity levels were between 15 to 20% with the three Hu1D10 antibodies. In this experiment, the An-Hu1D10 antibody was not as active in inducing cytotoxicity as the other two Hu1D10 antibodies, although the difference among the three antibodies was minimal. These results clearly indicate that the *Aspergillus*-derived Hu1D10 antibodies exhibit ADCC activities.

Example 19

Pharmacokinetics

An in vivo rat study was performed in order to compare the pharmacokinetics of trastuzumab purified from *A. niger* strain 2-LC/HC-38b with that of trastuzumab (Herceptin) purchased from Genentech Inc., South San Francisco.

Two groups of Sprague Dawley rats (weight range of approximately 250-300 g) received a 2 mg/kg IV bolus dose of *A. niger*-derived trastuzumab (N=3) or of the commercial trastuzumab (N=4). Animals were dosed according to individual body weight using trastuzumab preparations that had been diluted to a final concentration of 0.9 mg/mL. Blood for serum (0.5 mL/sample) was collected at 0, 1, 4, 8, 24, 48, 72 and 96 hours and 7, 12, and 14 days post-dose. Serum was prepared by centrifugation of the blood sample within 30 minutes of collection. The serum was decanted and the serum samples were stored on ice until transfer for storage at −80° C. Human IgG1 levels in these serum samples were measured by ELISA as described above. The serum concentration versus time profiles of the fungal-derived and commercial trastuzumabs are shown in FIG. 16. A noncompartmental analysis of the data was performed (Table 1). The parameters from this analysis as well as the serum concentration versus time profiles of trastuzumab from 2 LC/HC-38b and the commercial source were similar. Given the long survival time in the serum of both commercial trastuzumab and the antibody from 2 LC/HC-38b an accurate estimate of half-life could not be determined in this 14 day study. However, the parameters commonly used to evaluate bioequivalence, namely $C_{max}$ (the mean peak concentration of antibody in the serum) and $AUC_{last}$ (area under the concentration-time curve), were comparable for the 2 LC/HC 38b and mammalian cell-derived trastuzumabs. These results indicated that the fungal expression of trastuzumab did not affect the pharmacokinetic disposition of the antibody in vivo.

Although the foregoing invention has been described in some detail by way of illustration and example for purposes of clarity and understanding, it will be obvious that certain changes and modifications may be practiced within the scope of the appended claims.

TABLE 1

Pharmacokinetics of CHO-derived and *Aspergillus*-derived trastuzumab

| Meaned parameters from individual animals | | | Fungal |
|---|---|---|---|
| Parameter | Units | CHO Ab n = 4 | Ab n = 3 |
| Cmax | ug/mL | 49.5(6.2) | 48.3(3) |
| No_points_Lambda_z | | 8.25(1.5) | 4.67(1.5) |
| AUClast | day * ug/mL | 153(4.4) | 143(11) |
| HL_Lambda_z | day | 11.1(3.3) | 15(2) |
| AUCINF_obs | day * ug/mL | 297(45) | 285(5.4) |
| AUC_% Extrap_obs | % | 47.7(6.9) | 49.8(3) |
| Vz_obs | mL/kg | 106(16) | 152(23) |

What is claimed is:

1. A process for producing an immunoglobulin molecule or an immunologically functional immunoglobulin fragment comprising at least the variable domains of the immunoglobulin heavy and light chains, in a host filamentous fungus, comprising the steps of:

a. transforming said host with a first expression vector containing a fusion DNA construct encoding a first fusion polypeptide comprising, from a 5' end of said DNA construct, first, second, third and fourth nucleic acids, wherein said first nucleic acid encodes a signal polypeptide functional as a secretory sequence in the host, said second nucleic acid encodes a secreted polypeptide or functional portion thereof normally secreted from a filamentous fungus, said third nucleic acid encodes a cleavable linker and said fourth nucleic acid encodes an immunoglobulin light chain or fragment thereof;

b. transforming said host with a second expression vector containing a fusion nucleic acid encoding a second fusion polypeptide comprising, from a 5' end of said fusion nucleic acid, first, second, third and fourth nucleic acids, wherein said first nucleic acid encodes a signal polypeptide functional as a secretory sequence in the host, said second nucleic acid encodes a secreted polypeptide or functional portion thereof normally secreted from a filamentous fungus, said third nucleic acid encodes a cleavable linker and said fourth nucleic acid encodes an immunoglobulin heavy chain or fragment thereof;

c. growing said host under conditions which permit expression of said fusion DNA construct and said fusion nucleic acid sequences to cause the expression of the first fusion and the second fusion polypeptides; and d. isolating said immunoglobulin molecule or immunologically functional immunoglobulin fragment comprising at least the variable domains of the immunoglobulin heavy and lights chains;

wherein the secreted polypeptide or functional portion thereof in (a) and (b) is glucoamylase, and the cleavable linker in (a) and (b) is cleavable by a native filamentous fungus protease, and wherein the immunoglobulin or immunologically functional immunoglobulin fragment has an amino acid substitution N297Q in the heavy chain, and the immunoglobulin has reduced glycosylation due to the amino acid substitution N297Q in the heavy chain.

2. The process of claim 1, wherein the immunoglobulin molecule or fragment thereof is secreted.

3. The process according to claim 1, wherein the host filamentous fungus is an *Aspergillus, Neurospora*, or *Fusarium*.

4. The process according to claim 3, wherein the host filamentous fungus is an *Aspergillus*.

5. The process according to claim 4, wherein the host filamentous fungus is an *Aspergillus niger*.

6. The process according to claim 1, wherein the immunoglobulin has a fungal glycosylation pattern.

7. The process according to claim 6, wherein the immunoglobulin has a high mannose glycosylation pattern.

8. The process according to claim 1, wherein the transformation of step a) and step b) is a co-transformation.

9. The process according to claim 1, wherein the transformation of step a) and step b) are sequential transformations.

10. The host filamentous fungal cell transformed by the process of claim 1.

11. The process according to claim 1, wherein the cleavable linker in (a) and (b) is the KEX2 site.

12. The process according to claim 1, wherein the host filamentous fungus is an *Aspergillus, Neurospora, Fusarium, Trichoderma, Cephalosporium, Penicillium* or *Chrysosporium* and wherein the secreted polypeptide or functional portion thereof in (a) and (b) is glucoamylase from *Aspergillus niger*.

* * * * *

SEQUENCE LISTING

<160> NUMBER OF SEQ ID NOS: 42

<210> SEQ ID NO 1
<211> LENGTH: 39
<212> TYPE: DNA
<213> ORGANISM: Artificial Sequence
<220> FEATURE:
<223> OTHER INFORMATION: primer

<400> SEQUENCE: 1
ccgtggcggc gccatctgtc ttcatcttcc cgccatctg 39

<210> SEQ ID NO 2
<211> LENGTH: 42
<212> TYPE: DNA
<213> ORGANISM: Artificial Sequence
<220> FEATURE:
<223> OTHER INFORMATION: primer

<400> SEQUENCE: 2
cagttctaga ggatcaacac tctcccctgt tgaagctctt tg 42

<210> SEQ ID NO 3
<211> LENGTH: 357
<212> TYPE: DNA
<213> ORGANISM: Artificial Sequence
<220> FEATURE:
<223> OTHER INFORMATION: synthetic

<400> SEQUENCE: 3
gaattcgccc ttccgtggcg gcgccatctg tcttcatctt cccgccatct gatgagcagt 60
tgaaatctgg aactgcctct gttgtgtgcc tgctgaataa cttctatccc agagaggcca 120
aagtacagtg gaaggtggat aacgccctcc aatcgggtaa ctcccaggag agtgtcacag 180
agcaggacag caaggacagc acctacagcc tcagcagcac cctgacgctg agcaaagcag 240
actacgagaa acacaaagtc tacgcctgcg aagtcaccca tcagggcctg agctcgcccg 300
tcacaaagag cttcaacagg ggagagtgtt gatcctctag aactgaaggg cgaattc 357

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
gggcccatcg gtcttccccc tggca 25

<210> SEQ ID NO 5
<211> LENGTH: 41
<212> TYPE: DNA
<213> ORGANISM: Artificial Sequence
<220> FEATURE:
<223> OTHER INFORMATION: primer

<400> SEQUENCE: 5
cagttctaga ggatcattta cccggagaca gggagaggct c 41

<210> SEQ ID NO 6
<211> LENGTH: 991
<212> TYPE: DNA
<213> ORGANISM: Artificial Sequence
<220> FEATURE:

-continued

<223> OTHER INFORMATION: synthetic

<400> SEQUENCE: 6
gggcccatcg gtcttccccc tggcaccctc ctccaagagc acctctgggg gcacagcggc 60
cctgggctgc ctggtcaagg actacttccc cgaaccggtg acggtgtcgt ggaactcagg 120
cgccctgacc agcggcgtgc acaccttccc ggctgtccta cagtcctcag gactctactc 180
cctcagcagc gtggtgaccg tgccctccag cagcttgggc acccagacct acatctgcaa 240
cgtgaatcac aagcccagca acaccaaggt ggacaagaga gttgagccca aatcttgtga 300
caaaactcac acatgcccac cgtgcccagc acctgaactc ctggggggac cgtcagtctt 360
cctcttcccc ccaaaaccca aggacaccct catgatctcc cggacccctg aggtcacatg 420
cgtggtggtg gacgtgagcc acgaagaccc tgaggtcaag ttcaactggt acgtggacgg 480
cgtggaggtg cataatgcca agacaaagcc gcgggaggag cagtacaaca gcacgtaccg 540
tgtggtcagc gtcctcaccg tcctgcacca ggactggctg aatggcaagg agtacaagtg 600
caaggtctcc aacaaagccc tcccagcccc catcgagaaa accatctcca aagccaaagg 660
gcagccccga gaaccacagg tgtacaccct gcccccatcc cgggaggaga tgaccaagaa 720
ccaggtcagc ctgacctgcc tggtcaaagg cttctatccc agcgacatcg ccgtggagtg 780
ggagagcaat gggcagccgg agaacaacta caagaccacg cctcccgtgc tggactccga 840
cggctccttc ttcctctata gcaagctcac cgtggacaag agcaggtggc agcaggggaa 900
cgtcttctca tgctccgtga tgcatgaggc tctgcacaac cactacacgc agaagagcct 960
ctccctgtct ccgggtaaat gatcctctag a 991

<210> SEQ ID NO 7
<211> LENGTH: 351
<212> TYPE: DNA
<213> ORGANISM: Artificial Sequence
<220> FEATURE:
<223> OTHER INFORMATION: synthetic

<400> SEQUENCE: 7
tacgtataag cgcgatatcc agatgaccca gtccccgagc tccctgtccg cctctgtggg 60
cgatagggtc actatcacct gccgtgccag tcaggatgtg aatactgctg tagcctggta 120
tcaacagaaa cccggaaagg ccccgaaact gctgatttac tcggcatcct tcctctactc 180
tggagtccct tctcgcttct ctggttcccg ctctgggacg gatttcactc tgaccatcag 240
ctccctgcag ccggaagact tcgcaactta ttactgtcag caacactata ctactcctcc 300
gacgttcgga cagggtacca aggtggagat caaacgtacc gtggcggcgc c 351

<210> SEQ ID NO 8
<211> LENGTH: 390
<212> TYPE: DNA
<213> ORGANISM: Artificial Sequence
<220> FEATURE:
<223> OTHER INFORMATION: synthetic

<400> SEQUENCE: 8
tacgtataag cgcgaggttc agctggtgga gtctggcggt ggcctggtgc agcccggggg 60
ctctctccgt ttgtcctgtg cagcttctgg cttcaacatt aaagacacct atatccactg 120
ggtgcgtcag gctccgggta agggcctgga gtgggttgca aggatttatc ctacgaatgg 180
ttatactcgt tatgccgata gcgtcaaggg ccgtttcact ataagcgcag acacttcgaa 240
aaacacagcc tacctccaga tgaacagcct gcgtgctgag gacactgccg tctattattg 300

```
tagcagatgg ggtggggacg gcttctatgc tatggactac tggggtcaag gtacactagt    360

caccgtcagc agcgctagca ccaagggccc                                     390


<210> SEQ ID NO 9
<211> LENGTH: 743
<212> TYPE: PRT
<213> ORGANISM: Artificial Sequence
<220> FEATURE:
<223> OTHER INFORMATION: fusion protein

<400> SEQUENCE: 9

Met Ser Phe Arg Ser Leu Leu Ala Leu Ser Gly Leu Val Cys Thr Gly
 1               5                  10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350
```

-continued

```
Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Tyr Lys
        515                 520                 525

Arg Asp Ile Gln Met Thr Gln Ser Pro Ser Ser Leu Ser Ala Ser Val
    530                 535                 540

Gly Asp Arg Val Thr Ile Thr Cys Arg Ala Ser Gln Asp Val Asn Thr
545                 550                 555                 560

Ala Val Ala Trp Tyr Gln Gln Lys Pro Gly Lys Ala Pro Lys Leu Leu
                565                 570                 575

Ile Tyr Ser Ala Ser Phe Leu Tyr Ser Gly Val Pro Ser Arg Phe Ser
            580                 585                 590

Gly Ser Arg Ser Gly Thr Asp Phe Thr Leu Thr Ile Ser Ser Leu Gln
        595                 600                 605

Pro Glu Asp Phe Ala Thr Tyr Tyr Cys Gln Gln His Tyr Thr Thr Pro
    610                 615                 620

Pro Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740


<210> SEQ ID NO 10
<211> LENGTH: 979
<212> TYPE: PRT
<213> ORGANISM: Artificial Sequence
```

<220> FEATURE:
<223> OTHER INFORMATION: fusion protein

<400> SEQUENCE: 10

```
Met Ser Phe Arg Ser Leu Leu Ala Leu Ser Gly Leu Val Cys Thr Gly
 1              5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400
```

-continued

```
Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Tyr Lys
        515                 520                 525

Arg Glu Val Gln Leu Val Glu Ser Gly Gly Gly Leu Val Gln Pro Gly
    530                 535                 540

Gly Ser Leu Arg Leu Ser Cys Ala Ala Ser Gly Phe Asn Ile Lys Asp
545                 550                 555                 560

Thr Tyr Ile His Trp Val Arg Gln Ala Pro Gly Lys Gly Leu Glu Trp
                565                 570                 575

Val Ala Arg Ile Tyr Pro Thr Asn Gly Tyr Thr Arg Tyr Ala Asp Ser
            580                 585                 590

Val Lys Gly Arg Phe Thr Ile Ser Ala Asp Thr Ser Lys Asn Thr Ala
        595                 600                 605

Tyr Leu Gln Met Asn Ser Leu Arg Ala Glu Asp Thr Ala Val Tyr Tyr
    610                 615                 620

Cys Ser Arg Trp Gly Gly Asp Gly Phe Tyr Ala Met Asp Tyr Trp Gly
625                 630                 635                 640

Gln Gly Thr Leu Val Thr Val Ser Ser Ala Ser Thr Lys Gly Pro Ser
                645                 650                 655

Val Phe Pro Leu Ala Pro Ser Ser Lys Ser Thr Ser Gly Gly Thr Ala
            660                 665                 670

Ala Leu Gly Cys Leu Val Lys Asp Tyr Phe Pro Glu Pro Val Thr Val
        675                 680                 685

Ser Trp Asn Ser Gly Ala Leu Thr Ser Gly Val His Thr Phe Pro Ala
    690                 695                 700

Val Leu Gln Ser Ser Gly Leu Tyr Ser Leu Ser Ser Val Val Thr Val
705                 710                 715                 720

Pro Ser Ser Ser Leu Gly Thr Gln Thr Tyr Ile Cys Asn Val Asn His
                725                 730                 735

Lys Pro Ser Asn Thr Lys Val Asp Lys Arg Val Glu Pro Lys Ser Cys
            740                 745                 750

Asp Lys Thr His Thr Cys Pro Pro Cys Pro Ala Pro Glu Leu Leu Gly
        755                 760                 765

Gly Pro Ser Val Phe Leu Phe Pro Pro Lys Pro Lys Asp Thr Leu Met
    770                 775                 780

Ile Ser Arg Thr Pro Glu Val Thr Cys Val Val Val Asp Val Ser His
785                 790                 795                 800

Glu Asp Pro Glu Val Lys Phe Asn Trp Tyr Val Asp Gly Val Glu Val
                805                 810                 815

His Asn Ala Lys Thr Lys Pro Arg Glu Glu Gln Tyr Asn Ser Thr Tyr
            820                 825                 830
```

Arg Val Val Ser Val Leu Thr Val Leu His Gln Asp Trp Leu Asn Gly
835 840 845

Lys Glu Tyr Lys Cys Lys Val Ser Asn Lys Ala Leu Pro Ala Pro Ile
850 855 860

Glu Lys Thr Ile Ser Lys Ala Lys Gly Gln Pro Arg Glu Pro Gln Val
865 870 875 880

Tyr Thr Leu Pro Pro Ser Arg Glu Glu Met Thr Lys Asn Gln Val Ser
885 890 895

Leu Thr Cys Leu Val Lys Gly Phe Tyr Pro Ser Asp Ile Ala Val Glu
900 905 910

Trp Glu Ser Asn Gly Gln Pro Glu Asn Asn Tyr Lys Thr Thr Pro Pro
915 920 925

Val Leu Asp Ser Asp Gly Ser Phe Phe Leu Tyr Ser Lys Leu Thr Val
930 935 940

Asp Lys Ser Arg Trp Gln Gln Gly Asn Val Phe Ser Cys Ser Val Met
945 950 955 960

His Glu Ala Leu His Asn His Tyr Thr Gln Lys Ser Leu Ser Leu Ser
965 970 975

Pro Gly Lys

<210> SEQ ID NO 11
<211> LENGTH: 16
<212> TYPE: DNA
<213> ORGANISM: Artificial Sequence
<220> FEATURE:
<223> OTHER INFORMATION: primer

<400> SEQUENCE: 11
aacagctatg accatg 16

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
tctagaggat catgcggcgc acggtgggca tgtgtgag 38

<210> SEQ ID NO 13
<211> LENGTH: 763
<212> TYPE: PRT
<213> ORGANISM: Artificial Sequence
<220> FEATURE:
<223> OTHER INFORMATION: fusion protein

<400> SEQUENCE: 13

Met Ser Phe Arg Ser Leu Leu Ala Leu Ser Gly Leu Val Cys Thr Gly
1 5 10 15

Leu Ala Asn Val Ile Ser Lys Arg Ala Thr Leu Asp Ser Trp Leu Ser
20 25 30

Asn Glu Ala Thr Val Ala Arg Thr Ala Ile Leu Asn Asn Ile Gly Ala
35 40 45

Asp Gly Ala Trp Val Ser Gly Ala Asp Ser Gly Ile Val Val Ala Ser
50 55 60

Pro Ser Thr Asp Asn Pro Asp Tyr Phe Tyr Thr Trp Thr Arg Asp Ser
65 70 75 80

Gly Leu Val Leu Lys Thr Leu Val Asp Leu Phe Arg Asn Gly Asp Thr

-continued

```
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510
```

```
Ser Thr Ser Lys Thr Thr Ala Thr Ala Ser Lys Thr Ser Thr Tyr Lys
        515                 520                 525

Arg Glu Val Gln Leu Val Glu Ser Gly Gly Gly Leu Val Gln Pro Gly
    530                 535                 540

Gly Ser Leu Arg Leu Ser Cys Ala Ala Ser Gly Phe Asn Ile Lys Asp
545                 550                 555                 560

Thr Tyr Ile His Trp Val Arg Gln Ala Pro Gly Lys Gly Leu Glu Trp
                565                 570                 575

Val Ala Arg Ile Tyr Pro Thr Asn Gly Tyr Thr Arg Tyr Ala Asp Ser
            580                 585                 590

Val Lys Gly Arg Phe Thr Ile Ser Ala Asp Thr Ser Lys Asn Thr Ala
        595                 600                 605

Tyr Leu Gln Met Asn Ser Leu Arg Ala Glu Asp Thr Ala Val Tyr Tyr
    610                 615                 620

Cys Ser Arg Trp Gly Gly Asp Gly Phe Tyr Ala Met Asp Tyr Trp Gly
625                 630                 635                 640

Gln Gly Thr Leu Val Thr Val Ser Ser Ala Ser Thr Lys Gly Pro Ser
                645                 650                 655

Val Phe Pro Leu Ala Pro Ser Ser Lys Ser Thr Ser Gly Gly Thr Ala
            660                 665                 670

Ala Leu Gly Cys Leu Val Lys Asp Tyr Phe Pro Glu Pro Val Thr Val
        675                 680                 685

Ser Trp Asn Ser Gly Ala Leu Thr Ser Gly Val His Thr Phe Pro Ala
    690                 695                 700

Val Leu Gln Ser Ser Gly Leu Tyr Ser Leu Ser Ser Val Val Thr Val
705                 710                 715                 720

Pro Ser Ser Ser Leu Gly Thr Gln Thr Tyr Ile Cys Asn Val Asn His
                725                 730                 735

Lys Pro Ser Asn Thr Lys Val Asp Lys Arg Val Glu Pro Lys Ser Cys
            740                 745                 750

Asp Lys Thr His Thr Cys Pro Pro Cys Ala Ala
        755                 760
```

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14

```
gagcagtacc agagcacgta ccgtgtggtc                                        30
```

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15

```
gtacgtgctc tggtactgct cctcccgcgg ct                                     32
```

<210> SEQ ID NO 16
<211> LENGTH: 979
<212> TYPE: PRT
<213> ORGANISM: Artificial Sequence
<220> FEATURE:
<223> OTHER INFORMATION: fusion protein

<400> SEQUENCE: 16

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

-continued

```
Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Tyr Lys
        515                 520                 525

Arg Glu Val Gln Leu Val Glu Ser Gly Gly Gly Leu Val Gln Pro Gly
    530                 535                 540

Gly Ser Leu Arg Leu Ser Cys Ala Ala Ser Gly Phe Asn Ile Lys Asp
545                 550                 555                 560

Thr Tyr Ile His Trp Val Arg Gln Ala Pro Gly Lys Gly Leu Glu Trp
                565                 570                 575

Val Ala Arg Ile Tyr Pro Thr Asn Gly Tyr Thr Arg Tyr Ala Asp Ser
            580                 585                 590

Val Lys Gly Arg Phe Thr Ile Ser Ala Asp Thr Ser Lys Asn Thr Ala
        595                 600                 605

Tyr Leu Gln Met Asn Ser Leu Arg Ala Glu Asp Thr Ala Val Tyr Tyr
    610                 615                 620

Cys Ser Arg Trp Gly Gly Asp Gly Phe Tyr Ala Met Asp Tyr Trp Gly
625                 630                 635                 640

Gln Gly Thr Leu Val Thr Val Ser Ser Ala Ser Thr Lys Gly Pro Ser
                645                 650                 655

Val Phe Pro Leu Ala Pro Ser Ser Lys Ser Thr Ser Gly Gly Thr Ala
            660                 665                 670

Ala Leu Gly Cys Leu Val Lys Asp Tyr Phe Pro Glu Pro Val Thr Val
        675                 680                 685

Ser Trp Asn Ser Gly Ala Leu Thr Ser Gly Val His Thr Phe Pro Ala
    690                 695                 700

Val Leu Gln Ser Ser Gly Leu Tyr Ser Leu Ser Ser Val Val Thr Val
705                 710                 715                 720

Pro Ser Ser Ser Leu Gly Thr Gln Thr Tyr Ile Cys Asn Val Asn His
                725                 730                 735

Lys Pro Ser Asn Thr Lys Val Asp Lys Arg Val Glu Pro Lys Ser Cys
            740                 745                 750

Asp Lys Thr His Thr Cys Pro Pro Cys Pro Ala Pro Glu Leu Leu Gly
        755                 760                 765

Gly Pro Ser Val Phe Leu Phe Pro Pro Lys Pro Lys Asp Thr Leu Met
    770                 775                 780

Ile Ser Arg Thr Pro Glu Val Thr Cys Val Val Val Asp Val Ser His
785                 790                 795                 800

Glu Asp Pro Glu Val Lys Phe Asn Trp Tyr Val Asp Gly Val Glu Val
                805                 810                 815

His Asn Ala Lys Thr Lys Pro Arg Glu Glu Gln Tyr Gln Ser Thr Tyr
            820                 825                 830

Arg Val Val Ser Val Leu Thr Val Leu His Gln Asp Trp Leu Asn Gly
        835                 840                 845
```

Lys Glu Tyr Lys Cys Lys Val Ser Asn Lys Ala Leu Pro Ala Pro Ile
    850                 855                 860

Glu Lys Thr Ile Ser Lys Ala Lys Gly Gln Pro Arg Glu Pro Gln Val
865                 870                 875                 880

Tyr Thr Leu Pro Pro Ser Arg Glu Glu Met Thr Lys Asn Gln Val Ser
                885                 890                 895

Leu Thr Cys Leu Val Lys Gly Phe Tyr Pro Ser Asp Ile Ala Val Glu
            900                 905                 910

Trp Glu Ser Asn Gly Gln Pro Glu Asn Asn Tyr Lys Thr Thr Pro Pro
        915                 920                 925

Val Leu Asp Ser Asp Gly Ser Phe Phe Leu Tyr Ser Lys Leu Thr Val
    930                 935                 940

Asp Lys Ser Arg Trp Gln Gln Gly Asn Val Phe Ser Cys Ser Val Met
945                 950                 955                 960

His Glu Ala Leu His Asn His Tyr Thr Gln Lys Ser Leu Ser Leu Ser
                965                 970                 975

Pro Gly Lys

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
ccgctagcaa gcgtgatatc cag 23

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
ccggtgaccg gatcaacact ctccc 25

<210> SEQ ID NO 19
<211> LENGTH: 738
<212> TYPE: PRT
<213> ORGANISM: Artificial Sequence
<220> FEATURE:
<223> OTHER INFORMATION: fusion protein

<400> SEQUENCE: 19

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val

-continued

```
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Arg Asp Ile Gln Met
        515                 520                 525
```

```
Thr Gln Ser Pro Ser Ser Leu Ser Ala Ser Val Gly Asp Arg Val Thr
    530                 535                 540

Ile Thr Cys Arg Ala Ser Gln Asp Val Asn Thr Ala Val Ala Trp Tyr
545                 550                 555                 560

Gln Gln Lys Pro Gly Lys Ala Pro Lys Leu Leu Ile Tyr Ser Ala Ser
                565                 570                 575

Phe Leu Tyr Ser Gly Val Pro Ser Arg Phe Ser Gly Ser Arg Ser Gly
            580                 585                 590

Thr Asp Phe Thr Leu Thr Ile Ser Ser Leu Gln Pro Glu Asp Phe Ala
        595                 600                 605

Thr Tyr Tyr Cys Gln Gln His Tyr Thr Thr Pro Pro Thr Phe Gly Gln
    610                 615                 620

Gly Thr Lys Val Glu Ile Lys Arg Thr Val Ala Ala Pro Ser Val Phe
625                 630                 635                 640

Ile Phe Pro Pro Ser Asp Glu Gln Leu Lys Ser Gly Thr Ala Ser Val
                645                 650                 655

Val Cys Leu Leu Asn Asn Phe Tyr Pro Arg Glu Ala Lys Val Gln Trp
            660                 665                 670

Lys Val Asp Asn Ala Leu Gln Ser Gly Asn Ser Gln Glu Ser Val Thr
        675                 680                 685

Glu Gln Asp Ser Lys Asp Ser Thr Tyr Ser Leu Ser Ser Thr Leu Thr
    690                 695                 700

Leu Ser Lys Ala Asp Tyr Glu Lys His Lys Val Tyr Ala Cys Glu Val
705                 710                 715                 720

Thr His Gln Gly Leu Ser Ser Pro Val Thr Lys Ser Phe Asn Arg Gly
                725                 730                 735

Glu Cys


<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20

ccgctagcca gaagcgtgat atccaga                                          27


<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21

ccgctagcct caagcgtgat atccag                                           26


<210> SEQ ID NO 22
<211> LENGTH: 29
<212> TYPE: DNA
<213> ORGANISM: Artificial Sequence
<220> FEATURE:
<223> OTHER INFORMATION: primer

<400> SEQUENCE: 22

ccgctagcat ctccaagcgt gatatccag                                        29


<210> SEQ ID NO 23
<211> LENGTH: 35
```

<212> TYPE: DNA
<213> ORGANISM: Artificial Sequence
<220> FEATURE:
<223> OTHER INFORMATION: primer

<400> SEQUENCE: 23
ccgctagcaa cgtgatctcc aagcgtgata tccag 35

<210> SEQ ID NO 24
<211> LENGTH: 32
<212> TYPE: DNA
<213> ORGANISM: Artificial Sequence
<220> FEATURE:
<223> OTHER INFORMATION: primer

<400> SEQUENCE: 24
ccgctagcgt gatctccaag cgtgatatcc ag 32

<210> SEQ ID NO 25
<211> LENGTH: 47
<212> TYPE: DNA
<213> ORGANISM: Artificial Sequence
<220> FEATURE:
<223> OTHER INFORMATION: primer

<400> SEQUENCE: 25
ccgctagcat ctccaagcgt ggcggtggcg atatccagat gacccag 47

<210> SEQ ID NO 26
<211> LENGTH: 739
<212> TYPE: PRT
<213> ORGANISM: Artificial Sequence
<220> FEATURE:
<223> OTHER INFORMATION: fusion protein

<400> SEQUENCE: 26

```
Met Ser Phe Arg Ser Leu Leu Ala Leu Ser Gly Leu Val Cys Thr Gly
 1               5                  10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
```

```
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Gln Lys Arg Asp Ile Gln
        515                 520                 525

Met Thr Gln Ser Pro Ser Ser Leu Ser Ala Ser Val Gly Asp Arg Val
    530                 535                 540

Thr Ile Thr Cys Arg Ala Ser Gln Asp Val Asn Thr Ala Val Ala Trp
545                 550                 555                 560

Tyr Gln Gln Lys Pro Gly Lys Ala Pro Lys Leu Leu Ile Tyr Ser Ala
                565                 570                 575

Ser Phe Leu Tyr Ser Gly Val Pro Ser Arg Phe Ser Gly Ser Arg Ser
            580                 585                 590

Gly Thr Asp Phe Thr Leu Thr Ile Ser Ser Leu Gln Pro Glu Asp Phe
        595                 600                 605

Ala Thr Tyr Tyr Cys Gln Gln His Tyr Thr Thr Pro Pro Thr Phe Gly
    610                 615                 620
```

-continued

```
Gln Gly Thr Lys Val Glu Ile Lys Arg Thr Val Ala Ala Pro Ser Val
625                 630                 635                 640

Phe Ile Phe Pro Pro Ser Asp Glu Gln Leu Lys Ser Gly Thr Ala Ser
                645                 650                 655

Val Val Cys Leu Leu Asn Asn Phe Tyr Pro Arg Glu Ala Lys Val Gln
            660                 665                 670

Trp Lys Val Asp Asn Ala Leu Gln Ser Gly Asn Ser Gln Glu Ser Val
        675                 680                 685

Thr Glu Gln Asp Ser Lys Asp Ser Thr Tyr Ser Leu Ser Ser Thr Leu
    690                 695                 700

Thr Leu Ser Lys Ala Asp Tyr Glu Lys His Lys Val Tyr Ala Cys Glu
705                 710                 715                 720

Val Thr His Gln Gly Leu Ser Ser Pro Val Thr Lys Ser Phe Asn Arg
                725                 730                 735

Gly Glu Cys


<210> SEQ ID NO 27
<211> LENGTH: 739
<212> TYPE: PRT
<213> ORGANISM: Artificial Sequence
<220> FEATURE:
<223> OTHER INFORMATION: fusion protein

<400> SEQUENCE: 27

Met Ser Phe Arg Ser Leu Leu Ala Leu Ser Gly Leu Val Cys Thr Gly
 1               5                  10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255
```

```
Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Leu Lys Arg Asp Ile Gln
        515                 520                 525

Met Thr Gln Ser Pro Ser Ser Leu Ser Ala Ser Val Gly Asp Arg Val
    530                 535                 540

Thr Ile Thr Cys Arg Ala Ser Gln Asp Val Asn Thr Ala Val Ala Trp
545                 550                 555                 560

Tyr Gln Gln Lys Pro Gly Lys Ala Pro Lys Leu Leu Ile Tyr Ser Ala
                565                 570                 575

Ser Phe Leu Tyr Ser Gly Val Pro Ser Arg Phe Ser Gly Ser Arg Ser
            580                 585                 590

Gly Thr Asp Phe Thr Leu Thr Ile Ser Ser Leu Gln Pro Glu Asp Phe
        595                 600                 605

Ala Thr Tyr Tyr Cys Gln Gln His Tyr Thr Thr Pro Pro Thr Phe Gly
    610                 615                 620

Gln Gly Thr Lys Val Glu Ile Lys Arg Thr Val Ala Ala Pro Ser Val
625                 630                 635                 640

Phe Ile Phe Pro Pro Ser Asp Glu Gln Leu Lys Ser Gly Thr Ala Ser
                645                 650                 655

Val Val Cys Leu Leu Asn Asn Phe Tyr Pro Arg Glu Ala Lys Val Gln
            660                 665                 670

Trp Lys Val Asp Asn Ala Leu Gln Ser Gly Asn Ser Gln Glu Ser Val
```

```
        675                 680                 685

Thr Glu Gln Asp Ser Lys Asp Ser Thr Tyr Ser Leu Ser Ser Thr Leu
    690                 695                 700

Thr Leu Ser Lys Ala Asp Tyr Glu Lys His Lys Val Tyr Ala Cys Glu
705                 710                 715                 720

Val Thr His Gln Gly Leu Ser Ser Pro Val Thr Lys Ser Phe Asn Arg
                725                 730                 735

Gly Glu Cys


<210> SEQ ID NO 28
<211> LENGTH: 740
<212> TYPE: PRT
<213> ORGANISM: Artificial Sequence
<220> FEATURE:
<223> OTHER INFORMATION: fusion protein

<400> SEQUENCE: 28

Met Ser Phe Arg Ser Leu Leu Ala Leu Ser Gly Leu Val Cys Thr Gly
 1               5                  10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300
```

-continued

Val Val Asp Ser Phe Arg Ser Ile Tyr Thr Leu Asn Asp Gly Leu Ser
305 310 315 320

Asp Ser Glu Ala Val Ala Val Gly Arg Tyr Pro Glu Asp Thr Tyr Tyr
325 330 335

Asn Gly Asn Pro Trp Phe Leu Cys Thr Leu Ala Ala Ala Glu Gln Leu
340 345 350

Tyr Asp Ala Leu Tyr Gln Trp Asp Lys Gln Gly Ser Leu Glu Val Thr
355 360 365

Asp Val Ser Leu Asp Phe Phe Lys Ala Leu Tyr Ser Asp Ala Ala Thr
370 375 380

Gly Thr Tyr Ser Ser Ser Ser Ser Thr Tyr Ser Ser Ile Val Asp Ala
385 390 395 400

Val Lys Thr Phe Ala Asp Gly Phe Val Ser Ile Val Glu Thr His Ala
405 410 415

Ala Ser Asn Gly Ser Met Ser Glu Gln Tyr Asp Lys Ser Asp Gly Glu
420 425 430

Gln Leu Ser Ala Arg Asp Leu Thr Trp Ser Tyr Ala Ala Leu Leu Thr
435 440 445

Ala Asn Asn Arg Arg Asn Ser Val Val Pro Ala Ser Trp Gly Glu Thr
450 455 460

Ser Ala Ser Ser Val Pro Gly Thr Cys Ala Ala Thr Ser Ala Ile Gly
465 470 475 480

Thr Tyr Ser Ser Val Thr Val Thr Ser Trp Pro Ser Ile Val Ala Thr
485 490 495

Gly Gly Thr Thr Thr Thr Ala Thr Pro Thr Gly Ser Gly Ser Val Thr
500 505 510

Ser Thr Ser Lys Thr Thr Ala Thr Ala Ser Ile Ser Lys Arg Asp Ile
515 520 525

Gln Met Thr Gln Ser Pro Ser Ser Leu Ser Ala Ser Val Gly Asp Arg
530 535 540

Val Thr Ile Thr Cys Arg Ala Ser Gln Asp Val Asn Thr Ala Val Ala
545 550 555 560

Trp Tyr Gln Gln Lys Pro Gly Lys Ala Pro Lys Leu Leu Ile Tyr Ser
565 570 575

Ala Ser Phe Leu Tyr Ser Gly Val Pro Ser Arg Phe Ser Gly Ser Arg
580 585 590

Ser Gly Thr Asp Phe Thr Leu Thr Ile Ser Ser Leu Gln Pro Glu Asp
595 600 605

Phe Ala Thr Tyr Tyr Cys Gln Gln His Tyr Thr Thr Pro Pro Thr Phe
610 615 620

Gly Gln Gly Thr Lys Val Glu Ile Lys Arg Thr Val Ala Ala Pro Ser
625 630 635 640

Val Phe Ile Phe Pro Pro Ser Asp Glu Gln Leu Lys Ser Gly Thr Ala
645 650 655

Ser Val Val Cys Leu Leu Asn Asn Phe Tyr Pro Arg Glu Ala Lys Val
660 665 670

Gln Trp Lys Val Asp Asn Ala Leu Gln Ser Gly Asn Ser Gln Glu Ser
675 680 685

Val Thr Glu Gln Asp Ser Lys Asp Ser Thr Tyr Ser Leu Ser Ser Thr
690 695 700

Leu Thr Leu Ser Lys Ala Asp Tyr Glu Lys His Lys Val Tyr Ala Cys
705 710 715 720

Glu Val Thr His Gln Gly Leu Ser Ser Pro Val Thr Lys Ser Phe Asn
725 730 735

Arg Gly Glu Cys
740

<210> SEQ ID NO 29
<211> LENGTH: 742
<212> TYPE: PRT
<213> ORGANISM: Artificial Sequence
<220> FEATURE:
<223> OTHER INFORMATION: fusion protein

<400> SEQUENCE: 29

Met Ser Phe Arg Ser Leu Leu Ala Leu Ser Gly Leu Val Cys Thr Gly
1 5 10 15

Leu Ala Asn Val Ile Ser Lys Arg Ala Thr Leu Asp Ser Trp Leu Ser
20 25 30

Asn Glu Ala Thr Val Ala Arg Thr Ala Ile Leu Asn Asn Ile Gly Ala
35 40 45

Asp Gly Ala Trp Val Ser Gly Ala Asp Ser Gly Ile Val Val Ala Ser
50 55 60

Pro Ser Thr Asp Asn Pro Asp Tyr Phe Tyr Thr Trp Thr Arg Asp Ser
65 70 75 80

Gly Leu Val Leu Lys Thr Leu Val Asp Leu Phe Arg Asn Gly Asp Thr
85 90 95

Ser Leu Leu Ser Thr Ile Glu Asn Tyr Ile Ser Ala Gln Ala Ile Val
100 105 110

Gln Gly Ile Ser Asn Pro Ser Gly Asp Leu Ser Ser Gly Ala Gly Leu
115 120 125

Gly Glu Pro Lys Phe Asn Val Asp Glu Thr Ala Tyr Thr Gly Ser Trp
130 135 140

Gly Arg Pro Gln Arg Asp Gly Pro Ala Leu Arg Ala Thr Ala Met Ile
145 150 155 160

Gly Phe Gly Gln Trp Leu Leu Asp Asn Gly Tyr Thr Ser Thr Ala Thr
165 170 175

Asp Ile Val Trp Pro Leu Val Arg Asn Asp Leu Ser Tyr Val Ala Gln
180 185 190

Tyr Trp Asn Gln Thr Gly Tyr Asp Leu Trp Glu Glu Val Asn Gly Ser
195 200 205

Ser Phe Phe Thr Ile Ala Val Gln His Arg Ala Leu Val Glu Gly Ser
210 215 220

Ala Phe Ala Thr Ala Val Gly Ser Ser Cys Ser Trp Cys Asp Ser Gln
225 230 235 240

Ala Pro Glu Ile Leu Cys Tyr Leu Gln Ser Phe Trp Thr Gly Ser Phe
245 250 255

Ile Leu Ala Asn Phe Asp Ser Ser Arg Ser Gly Lys Asp Ala Asn Thr
260 265 270

Leu Leu Gly Ser Ile His Thr Phe Asp Pro Glu Ala Ala Cys Asp Asp
275 280 285

Ser Thr Phe Gln Pro Cys Ser Pro Arg Ala Leu Ala Asn His Lys Glu
290 295 300

Val Val Asp Ser Phe Arg Ser Ile Tyr Thr Leu Asn Asp Gly Leu Ser
305 310 315 320

Asp Ser Glu Ala Val Ala Val Gly Arg Tyr Pro Glu Asp Thr Tyr Tyr
325 330 335

Asn Gly Asn Pro Trp Phe Leu Cys Thr Leu Ala Ala Ala Glu Gln Leu
340 345 350

-continued

```
Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Asn Val Ile Ser Lys Arg
        515                 520                 525

Asp Ile Gln Met Thr Gln Ser Pro Ser Ser Leu Ser Ala Ser Val Gly
    530                 535                 540

Asp Arg Val Thr Ile Thr Cys Arg Ala Ser Gln Asp Val Asn Thr Ala
545                 550                 555                 560

Val Ala Trp Tyr Gln Gln Lys Pro Gly Lys Ala Pro Lys Leu Leu Ile
                565                 570                 575

Tyr Ser Ala Ser Phe Leu Tyr Ser Gly Val Pro Ser Arg Phe Ser Gly
            580                 585                 590

Ser Arg Ser Gly Thr Asp Phe Thr Leu Thr Ile Ser Ser Leu Gln Pro
        595                 600                 605

Glu Asp Phe Ala Thr Tyr Tyr Cys Gln Gln His Tyr Thr Thr Pro Pro
    610                 615                 620

Thr Phe Gly Gln Gly Thr Lys Val Glu Ile Lys Arg Thr Val Ala Ala
625                 630                 635                 640

Pro Ser Val Phe Ile Phe Pro Pro Ser Asp Glu Gln Leu Lys Ser Gly
                645                 650                 655

Thr Ala Ser Val Val Cys Leu Leu Asn Asn Phe Tyr Pro Arg Glu Ala
            660                 665                 670

Lys Val Gln Trp Lys Val Asp Asn Ala Leu Gln Ser Gly Asn Ser Gln
        675                 680                 685

Glu Ser Val Thr Glu Gln Asp Ser Lys Asp Ser Thr Tyr Ser Leu Ser
    690                 695                 700

Ser Thr Leu Thr Leu Ser Lys Ala Asp Tyr Glu Lys His Lys Val Tyr
705                 710                 715                 720

Ala Cys Glu Val Thr His Gln Gly Leu Ser Ser Pro Val Thr Lys Ser
                725                 730                 735

Phe Asn Arg Gly Glu Cys
            740
```

<210> SEQ ID NO 30
<211> LENGTH: 741
<212> TYPE: PRT
<213> ORGANISM: Artificial Sequence
<220> FEATURE:
<223> OTHER INFORMATION: fusion protein

<400> SEQUENCE: 30

```
Met Ser Phe Arg Ser Leu Leu Ala Leu Ser Gly Leu Val Cys Thr Gly
 1               5                  10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400
```

Val Lys Thr Phe Ala Asp Gly Phe Val Ser Ile Val Glu Thr His Ala
405 410 415

Ala Ser Asn Gly Ser Met Ser Glu Gln Tyr Asp Lys Ser Asp Gly Glu
420 425 430

Gln Leu Ser Ala Arg Asp Leu Thr Trp Ser Tyr Ala Ala Leu Leu Thr
435 440 445

Ala Asn Asn Arg Arg Asn Ser Val Val Pro Ala Ser Trp Gly Glu Thr
450 455 460

Ser Ala Ser Ser Val Pro Gly Thr Cys Ala Ala Thr Ser Ala Ile Gly
465 470 475 480

Thr Tyr Ser Ser Val Thr Val Thr Ser Trp Pro Ser Ile Val Ala Thr
485 490 495

Gly Gly Thr Thr Thr Thr Ala Thr Pro Thr Gly Ser Gly Ser Val Thr
500 505 510

Ser Thr Ser Lys Thr Thr Ala Thr Ala Ser Val Ile Ser Lys Arg Asp
515 520 525

Ile Gln Met Thr Gln Ser Pro Ser Ser Leu Ser Ala Ser Val Gly Asp
530 535 540

Arg Val Thr Ile Thr Cys Arg Ala Ser Gln Asp Val Asn Thr Ala Val
545 550 555 560

Ala Trp Tyr Gln Gln Lys Pro Gly Lys Ala Pro Lys Leu Leu Ile Tyr
565 570 575

Ser Ala Ser Phe Leu Tyr Ser Gly Val Pro Ser Arg Phe Ser Gly Ser
580 585 590

Arg Ser Gly Thr Asp Phe Thr Leu Thr Ile Ser Ser Leu Gln Pro Glu
595 600 605

Asp Phe Ala Thr Tyr Tyr Cys Gln Gln His Tyr Thr Thr Pro Pro Thr
610 615 620

Phe Gly Gln Gly Thr Lys Val Glu Ile Lys Arg Thr Val Ala Ala Pro
625 630 635 640

Ser Val Phe Ile Phe Pro Pro Ser Asp Glu Gln Leu Lys Ser Gly Thr
645 650 655

Ala Ser Val Val Cys Leu Leu Asn Asn Phe Tyr Pro Arg Glu Ala Lys
660 665 670

Val Gln Trp Lys Val Asp Asn Ala Leu Gln Ser Gly Asn Ser Gln Glu
675 680 685

Ser Val Thr Glu Gln Asp Ser Lys Asp Ser Thr Tyr Ser Leu Ser Ser
690 695 700

Thr Leu Thr Leu Ser Lys Ala Asp Tyr Glu Lys His Lys Val Tyr Ala
705 710 715 720

Cys Glu Val Thr His Gln Gly Leu Ser Ser Pro Val Thr Lys Ser Phe
725 730 735

Asn Arg Gly Glu Cys
740

<210> SEQ ID NO 31
<211> LENGTH: 743
<212> TYPE: PRT
<213> ORGANISM: Artificial Sequence
<220> FEATURE:
<223> OTHER INFORMATION: fusion protein

<400> SEQUENCE: 31

Met Ser Phe Arg Ser Leu Leu Ala Leu Ser Gly Leu Val Cys Thr Gly
1 5 10 15

Leu Ala Asn Val Ile Ser Lys Arg Ala Thr Leu Asp Ser Trp Leu Ser

-continued

```
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445
```

```
Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Ile Ser Lys Arg Gly Gly
        515                 520                 525

Gly Asp Ile Gln Met Thr Gln Ser Pro Ser Ser Leu Ser Ala Ser Val
    530                 535                 540

Gly Asp Arg Val Thr Ile Thr Cys Arg Ala Ser Gln Asp Val Asn Thr
545                 550                 555                 560

Ala Val Ala Trp Tyr Gln Gln Lys Pro Gly Lys Ala Pro Lys Leu Leu
                565                 570                 575

Ile Tyr Ser Ala Ser Phe Leu Tyr Ser Gly Val Pro Ser Arg Phe Ser
            580                 585                 590

Gly Ser Arg Ser Gly Thr Asp Phe Thr Leu Thr Ile Ser Ser Leu Gln
        595                 600                 605

Pro Glu Asp Phe Ala Thr Tyr Tyr Cys Gln Gln His Tyr Thr Thr Pro
    610                 615                 620

Pro Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740
```

<210> SEQ ID NO 32
<211> LENGTH: 670
<212> TYPE: DNA
<213> ORGANISM: Artificial Sequence
<220> FEATURE:
<223> OTHER INFORMATION: expression vector

<400> SEQUENCE: 32

```
gctagcatct ccaagcgcga catccagatg actcagtctc catcttctct atctgcatct      60

gtgggagaca gggtcacaat cacatgtcga gcaagtgaaa atatttacag ttatttagca     120

tggtaccagc agaaacctgg aaaagctcct aagctcctgg tctctaatgc taaaacctta     180

gcagaaggtg tgccatcaag gttcagtggc agtggatcag gcaaacagtt tactctgaca     240

atcagcagcc tgcagcctga agattttgct acttattact gtcaacatca ttatggtaat     300

tcgtacccgt tcggacaggg gaccaaactg gaaataaaac gaactgtggc tgcaccatct     360

gtcttcatct tcccgccatc tgatgagcag ttgaaatctg gaactgcctc tgttgtgtgc     420
```

ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660
tagggtgacc 670

<210> SEQ ID NO 33
<211> LENGTH: 679
<212> TYPE: DNA
<213> ORGANISM: Artificial Sequence
<220> FEATURE:
<223> OTHER INFORMATION: expression vector

<400> SEQUENCE: 33
gctagcatct ccaagcgcgg tggcggagac atccagatga ctcagtctcc atcttctcta 60
tctgcatctg tgggagacag ggtcacaatc acatgtcgag caagtgaaaa tatttacagt 120
tatttagcat ggtaccagca gaaacctgga aaagctccta agctcctggt ctctaatgct 180
aaaaccttag cagaaggtgt gccatcaagg ttcagtggca gtggatcagg caaacagttt 240
actctgacaa tcagcagcct gcagcctgaa gattttgcta cttattactg tcaacatcat 300
tatggtaatt cgtacccgtt cggacagggg accaaactgg aaataaaacg aactgtggct 360
gcaccatctg tcttcatctt cccgccatct gatgagcagt tgaaatctgg aactgcctct 420
gttgtgtgcc tgctgaataa cttctatccc agagaggcca aagtacagtg gaaggtggat 480
aacgccctcc aatcgggtaa ctcccaggag agtgtcacag agcaggacag caaggacagc 540
acctacagcc tcagcagcac cctgacgctg agcaaagcag actacgagaa acacaaagtc 600
tacgcctgcg aagtcaccca tcagggcctg agctcgcccg tcacaaagag cttcaacagg 660
ggagagtgtt agggtgacc 679

<210> SEQ ID NO 34
<211> LENGTH: 740
<212> TYPE: PRT
<213> ORGANISM: Artificial Sequence
<220> FEATURE:
<223> OTHER INFORMATION: fusion protein

<400> SEQUENCE: 34

Met Ser Phe Arg Ser Leu Leu Ala Leu Ser Gly Leu Val Cys Thr Gly
1 5 10 15

Leu Ala Asn Val Ile Ser Lys Arg Ala Thr Leu Asp Ser Trp Leu Ser
20 25 30

Asn Glu Ala Thr Val Ala Arg Thr Ala Ile Leu Asn Asn Ile Gly Ala
35 40 45

Asp Gly Ala Trp Val Ser Gly Ala Asp Ser Gly Ile Val Val Ala Ser
50 55 60

Pro Ser Thr Asp Asn Pro Asp Tyr Phe Tyr Thr Trp Thr Arg Asp Ser
65 70 75 80

Gly Leu Val Leu Lys Thr Leu Val Asp Leu Phe Arg Asn Gly Asp Thr
85 90 95

Ser Leu Leu Ser Thr Ile Glu Asn Tyr Ile Ser Ala Gln Ala Ile Val
100 105 110

Gln Gly Ile Ser Asn Pro Ser Gly Asp Leu Ser Ser Gly Ala Gly Leu
115 120 125

Gly Glu Pro Lys Phe Asn Val Asp Glu Thr Ala Tyr Thr Gly Ser Trp

```
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Ile Ser Lys Arg Asp Ile
        515                 520                 525

Gln Met Thr Gln Ser Pro Ser Ser Leu Ser Ala Ser Val Gly Asp Arg
    530                 535                 540

Val Thr Ile Thr Cys Arg Ala Ser Glu Asn Ile Tyr Ser Tyr Leu Ala
545                 550                 555                 560
```

```
Trp Tyr Gln Gln Lys Pro Gly Lys Ala Pro Lys Leu Leu Val Ser Asn
                565                 570                 575

Ala Lys Thr Leu Ala Glu Gly Val Pro Ser Arg Phe Ser Gly Ser Gly
            580                 585                 590

Ser Gly Lys Gln Phe Thr Leu Thr Ile Ser Ser Leu Gln Pro Glu Asp
        595                 600                 605

Phe Ala Thr Tyr Tyr Cys Gln His His Tyr Gly Asn Ser Tyr Pro Phe
    610                 615                 620

Gly Gln Gly Thr Lys Leu Glu Ile Lys Arg Thr Val Ala Ala Pro Ser
625                 630                 635                 640

Val Phe Ile Phe Pro Pro Ser Asp Glu Gln Leu Lys Ser Gly Thr Ala
                645                 650                 655

Ser Val Val Cys Leu Leu Asn Asn Phe Tyr Pro Arg Glu Ala Lys Val
            660                 665                 670

Gln Trp Lys Val Asp Asn Ala Leu Gln Ser Gly Asn Ser Gln Glu Ser
        675                 680                 685

Val Thr Glu Gln Asp Ser Lys Asp Ser Thr Tyr Ser Leu Ser Ser Thr
    690                 695                 700

Leu Thr Leu Ser Lys Ala Asp Tyr Glu Lys His Lys Val Tyr Ala Cys
705                 710                 715                 720

Glu Val Thr His Gln Gly Leu Ser Ser Pro Val Thr Lys Ser Phe Asn
                725                 730                 735

Arg Gly Glu Cys
            740
```

<210> SEQ ID NO 35
<211> LENGTH: 743
<212> TYPE: PRT
<213> ORGANISM: Artificial Sequence
<220> FEATURE:
<223> OTHER INFORMATION: fusion protein

<400> SEQUENCE: 35

```
Met Ser Phe Arg Ser Leu Leu Ala Leu Ser Gly Leu Val Cys Thr Gly
 1               5                  10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
```

-continued

```
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Ile Ser Lys Arg Gly Gly
        515                 520                 525

Gly Asp Ile Gln Met Thr Gln Ser Pro Ser Ser Leu Ser Ala Ser Val
    530                 535                 540

Gly Asp Arg Val Thr Ile Thr Cys Arg Ala Ser Glu Asn Ile Tyr Ser
545                 550                 555                 560

Tyr Leu Ala Trp Tyr Gln Gln Lys Pro Gly Lys Ala Pro Lys Leu Leu
                565                 570                 575

Val Ser Asn Ala Lys Thr Leu Ala Glu Gly Val Pro Ser Arg Phe Ser
            580                 585                 590

Gly Ser Gly Ser Gly Lys Gln Phe Thr Leu Thr Ile Ser Ser Leu Gln
        595                 600                 605
```

```
Pro Glu Asp Phe Ala Thr Tyr Tyr Cys Gln His His Tyr Gly Asn Ser
    610                 615                 620

Tyr Pro Phe Gly Gln Gly Thr Lys Leu Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740
```

<210> SEQ ID NO 36
<211> LENGTH: 1366
<212> TYPE: DNA
<213> ORGANISM: Artificial Sequence
<220> FEATURE:
<223> OTHER INFORMATION: expression vector

<400> SEQUENCE: 36

```
gctagcatct ccaagcgcca ggtgcagctg caggagtcag gaccaggcct agtgaagccc     60

tcagagactc tgtccctaac ctgcacagtc tctggtttct cattaactaa ctatggtgta    120

cactgggttc gccagtctcc aggaaagggt ctggaatgga tcggagtgaa atggagtggt    180

gggtcgacag aatataatgc agctttcata tccagactga ccatcagcaa ggacacctcc    240

aagaaccaag tttcccttaa actgaacagt ctgaccgctg ctgacacagc cgtgtactac    300

tgtgccagaa atgatagata tgctatggac tactggggtc aaggaactct agtcaccgtc    360

tcctcagcct ccaccaaggg cccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgacagtgc cctccagcag cttgggcacc    600

cagacctaca tctgcaacgt gaatcacaag cccagcaaca ccaaggtgga caagaaagtt    660

gagcccaaat cttgtgacaa aactcacaca tgcccaccgt gcccagcacc tgaactcctg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacaacagca cgtaccgtgt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gatgagctga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320
```

tacacgcaga agagcctctc cctgtctccg ggtaaatgag gtgacc 1366

<210> SEQ ID NO 37
<211> LENGTH: 1375
<212> TYPE: DNA
<213> ORGANISM: Artificial Sequence
<220> FEATURE:
<223> OTHER INFORMATION: expression vector

<400> SEQUENCE: 37
gctagcatct ccaagcgcgg tggcggacag gtgcagctgc aggagtcagg accaggccta 60
gtgaagccct cagagactct gtccctaacc tgcacagtct ctggtttctc attaactaac 120
tatggtgtac actgggttcg ccagtctcca ggaaagggtc tggaatggat cggagtgaaa 180
tggagtggtg ggtcgacaga atataatgca gctttcatat ccagactgac catcagcaag 240
gacacctcca agaaccaagt ttcccttaaa ctgaacagtc tgaccgctgc tgacacagcc 300
gtgtactact gtgccagaaa tgatagatat gctatggact actggggtca aggaactcta 360
gtcaccgtct cctcagcctc caccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgacagtgcc ctccagcagc 600
ttgggcaccc agacctacat ctgcaacgtg aatcacaagc ccagcaacac caaggtggac 660
aagaaagttg agcccaaatc ttgtgacaaa actcacacat gcccaccgtg cccagcacct 720
gaactcctgg ggggaccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc agcccccatc 1020
gagaaaacca tctccaaagc caaagggcag ccccgagaac cacaggtgta caccctgccc 1080
ccatcccggg atgagctgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctacagcaa gctcaccgtg 1260
gacaagagca ggtggcagca ggggaacgtc ttctcatgct ccgtgatgca tgaggctctg 1320
cacaaccact acacgcagaa gagcctctcc ctgtctccgg gtaaatgagg tgacc 1375

<210> SEQ ID NO 38
<211> LENGTH: 972
<212> TYPE: PRT
<213> ORGANISM: Artificial Sequence
<220> FEATURE:
<223> OTHER INFORMATION: fusion protein

<400> SEQUENCE: 38

Met Ser Phe Arg Ser Leu Leu Ala Leu Ser Gly Leu Val Cys Thr Gly
1 5 10 15

Leu Ala Asn Val Ile Ser Lys Arg Ala Thr Leu Asp Ser Trp Leu Ser
20 25 30

Asn Glu Ala Thr Val Ala Arg Thr Ala Ile Leu Asn Asn Ile Gly Ala
35 40 45

Asp Gly Ala Trp Val Ser Gly Ala Asp Ser Gly Ile Val Val Ala Ser
50 55 60

-continued

```
Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
```

-continued

```
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Ile Ser Lys Arg Gln Val
        515                 520                 525

Gln Leu Gln Glu Ser Gly Pro Gly Leu Val Lys Pro Ser Glu Thr Leu
    530                 535                 540

Ser Leu Thr Cys Thr Val Ser Gly Phe Ser Leu Thr Asn Tyr Gly Val
545                 550                 555                 560

His Trp Val Arg Gln Ser Pro Gly Lys Gly Leu Glu Trp Ile Gly Val
                565                 570                 575

Lys Trp Ser Gly Gly Ser Thr Glu Tyr Asn Ala Ala Phe Ile Ser Arg
            580                 585                 590

Leu Thr Ile Ser Lys Asp Thr Ser Lys Asn Gln Val Ser Leu Lys Leu
        595                 600                 605

Asn Ser Leu Thr Ala Ala Asp Thr Ala Val Tyr Tyr Cys Ala Arg Asn
    610                 615                 620

Asp Arg Tyr Ala Met Asp Tyr Trp Gly Gln Gly Thr Leu Val Thr Val
625                 630                 635                 640

Ser Ser Ala Ser Thr Lys Gly Pro Ser Val Phe Pro Leu Ala Pro Ser
                645                 650                 655

Ser Lys Ser Thr Ser Gly Gly Thr Ala Ala Leu Gly Cys Leu Val Lys
            660                 665                 670

Asp Tyr Phe Pro Glu Pro Val Thr Val Ser Trp Asn Ser Gly Ala Leu
        675                 680                 685

Thr Ser Gly Val His Thr Phe Pro Ala Val Leu Gln Ser Ser Gly Leu
    690                 695                 700

Tyr Ser Leu Ser Ser Val Val Thr Val Pro Ser Ser Ser Leu Gly Thr
705                 710                 715                 720

Gln Thr Tyr Ile Cys Asn Val Asn His Lys Pro Ser Asn Thr Lys Val
                725                 730                 735

Asp Lys Lys Val Glu Pro Lys Ser Cys Asp Lys Thr His Thr Cys Pro
            740                 745                 750

Pro Cys Pro Ala Pro Glu Leu Leu Gly Gly Pro Ser Val Phe Leu Phe
        755                 760                 765

Pro Pro Lys Pro Lys Asp Thr Leu Met Ile Ser Arg Thr Pro Glu Val
    770                 775                 780

Thr Cys Val Val Val Asp Val Ser His Glu Asp Pro Glu Val Lys Phe
785                 790                 795                 800

Asn Trp Tyr Val Asp Gly Val Glu Val His Asn Ala Lys Thr Lys Pro
                805                 810                 815

Arg Glu Glu Gln Tyr Asn Ser Thr Tyr Arg Val Val Ser Val Leu Thr
            820                 825                 830

Val Leu His Gln Asp Trp Leu Asn Gly Lys Glu Tyr Lys Cys Lys Val
        835                 840                 845

Ser Asn Lys Ala Leu Pro Ala Pro Ile Glu Lys Thr Ile Ser Lys Ala
    850                 855                 860

Lys Gly Gln Pro Arg Glu Pro Gln Val Tyr Thr Leu Pro Pro Ser Arg
865                 870                 875                 880

Asp Glu Leu Thr Lys Asn Gln Val Ser Leu Thr Cys Leu Val Lys Gly
                885                 890                 895

Phe Tyr Pro Ser Asp Ile Ala Val Glu Trp Glu Ser Asn Gly Gln Pro
            900                 905                 910
```

```
Glu Asn Asn Tyr Lys Thr Thr Pro Pro Val Leu Asp Ser Asp Gly Ser
        915                 920                 925

Phe Phe Leu Tyr Ser Lys Leu Thr Val Asp Lys Ser Arg Trp Gln Gln
    930                 935                 940

Gly Asn Val Phe Ser Cys Ser Val Met His Glu Ala Leu His Asn His
945                 950                 955                 960

Tyr Thr Gln Lys Ser Leu Ser Leu Ser Pro Gly Lys
                965                 970


<210> SEQ ID NO 39
<211> LENGTH: 975
<212> TYPE: PRT
<213> ORGANISM: Artificial Sequence
<220> FEATURE:
<223> OTHER INFORMATION: fusion protein

<400> SEQUENCE: 39

Met Ser Phe Arg Ser Leu Leu Ala Leu Ser Gly Leu Val Cys Thr Gly
 1               5                  10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
```

```
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Ile Ser Lys Arg Gly Gly
        515                 520                 525

Gly Gln Val Gln Leu Gln Glu Ser Gly Pro Gly Leu Val Lys Pro Ser
    530                 535                 540

Glu Thr Leu Ser Leu Thr Cys Thr Val Ser Gly Phe Ser Leu Thr Asn
545                 550                 555                 560

Tyr Gly Val His Trp Val Arg Gln Ser Pro Gly Lys Gly Leu Glu Trp
                565                 570                 575

Ile Gly Val Lys Trp Ser Gly Gly Ser Thr Glu Tyr Asn Ala Ala Phe
            580                 585                 590

Ile Ser Arg Leu Thr Ile Ser Lys Asp Thr Ser Lys Asn Gln Val Ser
        595                 600                 605

Leu Lys Leu Asn Ser Leu Thr Ala Ala Asp Thr Ala Val Tyr Tyr Cys
    610                 615                 620

Ala Arg Asn Asp Arg Tyr Ala Met Asp Tyr Trp Gly Gln Gly Thr Leu
625                 630                 635                 640

Val Thr Val Ser Ser Ala Ser Thr Lys Gly Pro Ser Val Phe Pro Leu
                645                 650                 655

Ala Pro Ser Ser Lys Ser Thr Ser Gly Gly Thr Ala Ala Leu Gly Cys
            660                 665                 670

Leu Val Lys Asp Tyr Phe Pro Glu Pro Val Thr Val Ser Trp Asn Ser
        675                 680                 685

Gly Ala Leu Thr Ser Gly Val His Thr Phe Pro Ala Val Leu Gln Ser
    690                 695                 700

Ser Gly Leu Tyr Ser Leu Ser Ser Val Val Thr Val Pro Ser Ser Ser
705                 710                 715                 720

Leu Gly Thr Gln Thr Tyr Ile Cys Asn Val Asn His Lys Pro Ser Asn
                725                 730                 735
```

```
Thr Lys Val Asp Lys Lys Val Glu Pro Lys Ser Cys Asp Lys Thr His
            740                 745                 750

Thr Cys Pro Pro Cys Pro Ala Pro Glu Leu Leu Gly Gly Pro Ser Val
        755                 760                 765

Phe Leu Phe Pro Pro Lys Pro Lys Asp Thr Leu Met Ile Ser Arg Thr
    770                 775                 780

Pro Glu Val Thr Cys Val Val Val Asp Val Ser His Glu Asp Pro Glu
785                 790                 795                 800

Val Lys Phe Asn Trp Tyr Val Asp Gly Val Glu Val His Asn Ala Lys
                805                 810                 815

Thr Lys Pro Arg Glu Glu Gln Tyr Asn Ser Thr Tyr Arg Val Val Ser
            820                 825                 830

Val Leu Thr Val Leu His Gln Asp Trp Leu Asn Gly Lys Glu Tyr Lys
        835                 840                 845

Cys Lys Val Ser Asn Lys Ala Leu Pro Ala Pro Ile Glu Lys Thr Ile
    850                 855                 860

Ser Lys Ala Lys Gly Gln Pro Arg Glu Pro Gln Val Tyr Thr Leu Pro
865                 870                 875                 880

Pro Ser Arg Asp Glu Leu Thr Lys Asn Gln Val Ser Leu Thr Cys Leu
                885                 890                 895

Val Lys Gly Phe Tyr Pro Ser Asp Ile Ala Val Glu Trp Glu Ser Asn
            900                 905                 910

Gly Gln Pro Glu Asn Asn Tyr Lys Thr Thr Pro Pro Val Leu Asp Ser
        915                 920                 925

Asp Gly Ser Phe Phe Leu Tyr Ser Lys Leu Thr Val Asp Lys Ser Arg
    930                 935                 940

Trp Gln Gln Gly Asn Val Phe Ser Cys Ser Val Met His Glu Ala Leu
945                 950                 955                 960

His Asn His Tyr Thr Gln Lys Ser Leu Ser Leu Ser Pro Gly Lys
                965                 970                 975


<210> SEQ ID NO 40
<211> LENGTH: 7
<212> TYPE: PRT
<213> ORGANISM: Artificial Sequence
<220> FEATURE:
<223> OTHER INFORMATION: fusion protein

<400> SEQUENCE: 40

Ile Ser Lys Arg Gly Gly Gly
 1               5


<210> SEQ ID NO 41
<211> LENGTH: 5
<212> TYPE: PRT
<213> ORGANISM: Artificial Sequence
<220> FEATURE:
<223> OTHER INFORMATION: synthetic peptide

<400> SEQUENCE: 41

Asp Ile Gln Met Thr
 1               5


<210> SEQ ID NO 42
<211> LENGTH: 5
<212> TYPE: PRT
<213> ORGANISM: Artificial Sequence
```

-continued

```
<220> FEATURE:
<223> OTHER INFORMATION: synthetic peptide

<400> SEQUENCE: 42

Gly Gly Gly Asp Ile
 1              5
```